United States Patent
Bouillot et al.

(10) Patent No.: US 10,273,232 B2
(45) Date of Patent: *Apr. 30, 2019

(54) 3-(6-ALKOXY-5-CHLOROBENZO[D]ISOXAZOL-3-YL)PROPANOIC ACID USEFUL AS KYNURENINE MONOOXYGENASE INHIBITORS

(71) Applicant: GlaxoSmithKline Intellectual Property Development Limited, Brentford, Middlesex (GB)

(72) Inventors: Anne Marie Jeanne Bouillot, Les Ulis (FR); Alexis Denis, Les Ulis (FR); John Liddle, Stevenage (GB); Ann Louise Walker, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,043

(22) Filed: Feb. 20, 2018

(65) Prior Publication Data

US 2018/0170921 A1    Jun. 21, 2018

Related U.S. Application Data

(63) Continuation of application No. 15/537,805, filed as application No. PCT/EP2015/080221 on Dec. 17, 2015, now Pat. No. 9,932,328.

(30) Foreign Application Priority Data

Dec. 19, 2014 (GB) .................................. 1422727.6
May 22, 2015 (GB) .................................. 1508866.9

(51) Int. Cl.
    C07D 413/12    (2006.01)
(52) U.S. Cl.
    CPC .................................. C07D 413/12 (2013.01)
(58) Field of Classification Search
    CPC .............................. C07D 413/12; A61K 31/416
    See application file for complete search history.

(56) References Cited

U.S. PATENT DOCUMENTS 9,932,328 B2 *  4/2018  Bouillot ............... C07D 413/12
2016/0318884 A1  11/2016  Bouillot et al.

FOREIGN PATENT DOCUMENTS

| WO | WO 2008/142134 A1 | 11/2008 |
| WO | WO 2010/011302 A1 | 1/2010 |
| WO | WO 2010/17132 A1 | 2/2010 |
| WO | WO 2015/091647 A1 | 6/2015 |

OTHER PUBLICATIONS

Shastri, R.A., "Synthesis and biological screening of some novel 2-(2-benzisoxazol-3-yl) ethyl)-1 Hbenzimidazoles", *Indian Journal of Chemistry*, Section B, vol. 52B, No. 1, pp. 160-163 (2013).
Search Report PCT Application PCT/EP2015/080221 filed Dec. 17, 2015.

* cited by examiner

*Primary Examiner* — Alexander R Pagano
(74) *Attorney, Agent, or Firm* — Grace C. Hsu; Fang Qian

(57) ABSTRACT

The present invention relates to a compound of formula (I)

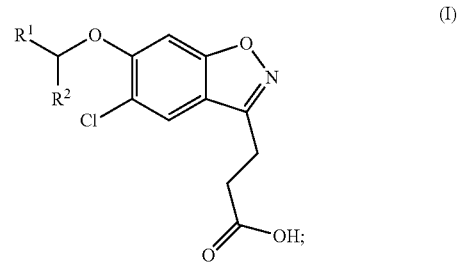

or pharmaceutically acceptable salts thereof, which are Kynurenine monooxygenase (KMO) inhibitors, which are useful in the treatment of various disorders, which may include, but are not limited to, for diseases such as, for example: acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

24 Claims, No Drawings

3-(6-ALKOXY-5-CHLOROBENZO[D]ISOXAZOL-3-YL)PROPANOIC ACID USEFUL AS KYNURENINE MONOOXYGENASE INHIBITORS

FIELD OF THE INVENTION

The present invention relates to 5-chlorobenzo[d]isoxazole compounds, processes for their preparation, pharmaceutical compositions comprising 5-chlorobenzo[d]isoxazole compounds and to their use in the treatment of various conditions or disorders such as acute pancreatitis and other conditions or disorders mediated by KMO.

BACKGROUND OF THE INVENTION

Kynurenine monooxygenase (KMO) is a flavin adenine dinucleotide (FAD) dependent monooxygenase located on the outer mitochondrial membrane. KMO is known to oxidise L-kynurenine (KYN) to 3-hydroxykynurenine (3HK) as part of the major route of catabolism of tryptophan. 3HK is then converted to 3-hydroxyanthranilic acid and quinolinic acid by kynureninase (KYNU) and 3-hydroxyanthranilate 3,4-dioxygenase (3-HAAO).

KMO is highly expressed in tissues including the liver, placenta, kidney [Alberati-Giani, FEBS Lett. 410:407-412 (1997)], endothelial cells and monocytes and at a lower level in microglia and macrophages in the brain.

Increased levels of 3HK and quinolinic acid and reduced levels of kynurenic acid (KYNA), which is formed from kynurenine by an alternative pathway, have been implicated in a number of diseases including Huntington's Disease, Parkinson's Disease, Alzheimer's Disease, amyotrophic lateral sclerosis (ALS) [Amaral, Outeiro et Al. Journal of Molecular Medicine 2013: 91(6): 705-713] and acute pancreatitis [Mole, McFerran et al. British Journal of Surgery 2008: 95: 855-867]. In the CNS 3-HK and quinolinic acid have been shown to be neurotoxic and KYNA to have neuroprotective effects. Inhibition of KMO oxidative activity would therefore be expected to result in reduced levels of 3-HK and quinolinic acid and increased levels of KYNA and to potentially show benefit in these diseases.

There is a large body of evidence showing that tryptophan metabolism is also altered in a range of acute injury settings. For instance, increased kynurenine levels have been associated with the development of sepsis following trauma [Pellegrin, 2005, Logters, 2009], while increased levels of both kynurenine and 3-HK correlate with the development of organ failure in acute pancreatitis [Mole, McFerran et al. British Journal of Surgery 2008: 95: 855-867]. This dysregulation of tryptophan metabolism is in part accounted for by the induction of indolamine 2,3 dioxygenase (IDO, the enzyme that converts tryptophan to N-formyl kynurenine) as part of the inflammatory cascade, but the development of organ dysfunction appears dependent on the downstream metabolites [Mole, McFerran et al. British Journal of Surgery 2008: 95: 855-867].

Acute pancreatitis (AP) results from local injury to the organ driven by factors such as excessive alcohol consumption or gallstones. The arising abdominal pain is extremely severe, and patients will invariably present to an emergency department rapidly following onset of an attack, with elevation of serum amylase used as a diagnostic measure. In the majority of cases, the disease is self-limiting, and the pain is resolved within 24-36 hours. However for the remaining 20-30% of patients a systemic inflammatory response occurs, resulting in rapid progression to multiple organ dysfunction (MOD). This leads to a prolonged stay in an intensive care unit (ICU), averaging 17 days, with a mortality rate of over 30%. Despite this high unmet need and the seriousness of the disease, there are no effective treatments available, with current standard of care being purely supportive.

WO2013016488, WO2011091153, WO2010017132, WO2010017179, WO2010011302, WO2008022286 and WO2008022281 describe inhibitors of KMO for targeting neurodegenerative disorders or diseases. EP1475385, EP1424333 describe inhibitors of KMO for targeting degenerative and inflammatory conditions. There remains a need for KMO inhibitors for use in the treatment various conditions or disorders mediated by KMO such as acute pancreatitis and other conditions associated with systemic inflammatory response syndrome (SIRS). WO2015091647 discloses 5-chlorobenzo[d]oxazol-2(3H)-one derivatives as inhibitors of KMO.

A class of compounds has now been found which are inhibitors of KMO. Inhibitors of KMO may be useful in the treatment of various conditions or disorders such as, for example, acute pancreatitis and acute conditions associated with systemic inflammatory response syndrome (SIRS).

SUMMARY OF THE INVENTION

The invention is directed to compounds of formula (I):

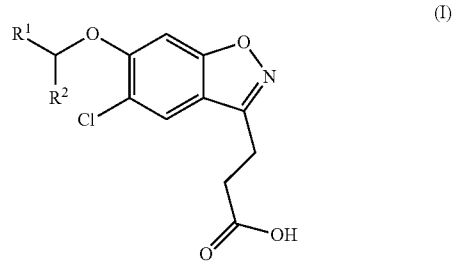

wherein $R^1$ and $R^2$ are as defined below;
or a salt thereof.

Certain compounds have been shown to be KMO inhibitors. Compounds which inhibit KMO may be useful in the treatment of various disorders, for example acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel disease, severe acute hepatic disease, severe acute hepatic encephalopathy or acute renal failure.

Accordingly, the invention is further directed to methods of treatment of a condition or disorder mediated by KMO, which methods comprise administering to a patient in need thereof a therapeutically effective amount of a compound of formula (I) or a pharmaceutically acceptable salt thereof.

The invention is further directed to a pharmaceutical composition comprising a therapeutically effective amount of a compound of formula (I) or a pharmaceutically acceptable salt thereof and a pharmaceutically acceptable excipient.

The invention is further directed to a compound of formula (I) or a pharmaceutically acceptable salt thereof for use in therapy.

The invention is further directed to the use of a compound of formula (I) or a pharmaceutically acceptable salt thereof in the manufacture of a medicament for the treatment of a disorder or condition mediated by KMO.

DETAILED DESCRIPTION OF THE INVENTION

In a first aspect, there are provided compounds of formula (I):

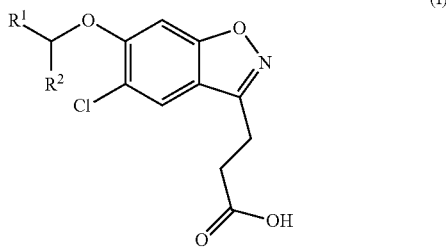

wherein:
$R^1$ is unsubstituted heteroaryl or heteroaryl substituted by methyl, ethyl, halo or =O; and
$R^2$ is H, methyl or ethyl.
or a salt thereof.

In one embodiment, $R^1$ is a 5-membered heteroaryl comprising one nitrogen atom or one oxygen atom and further comprising a nitrogen atom, or a 6-membered heteroaryl comprising one, two or three nitrogen atoms, wherein said heteroaryl is unsubstituted or substituted by methyl, ethyl, halo or =O.

In one embodiment, $R^1$ is selected from the group consisting of oxazolyl, pyrazolyl, pyridyl, pyridazinyl, and pyrimidinyl; wherein the oxazolyl, pyrazolyl, pyridyl, pyridazinyl, and pyrimidinyl may be unsubstituted or substituted by methyl, ethyl, halo or =O.

In one embodiment, $R^1$ is selected from the group consisting of unsubstituted oxazolyl, and pyridyl, pyridazinyl, and pyrimidinyl; wherein the pyridyl, pyridazinyl, and pyrimidinyl may be unsubstituted or substituted by methyl, halo or =O.

In one embodiment, $R^1$ is selected from the group consisting of unsubstituted oxazolyl, pyridyl, pyridazinyl, and pyrimidinyl; wherein the pyridyl and pyrimidinyl may be unsubstituted or substituted by methyl, halo or =O and the pyridazinyl may be unsubstituted or substituted by methyl or =O.

In one embodiment, $R^1$ is selected from the group consisting of oxazolyl, pyridyl, pyridazinyl, and pyrimidinyl; wherein the oxazolyl, pyridyl pyridazinyl and pyrimidinyl may be unsubstituted or substituted by methyl, halo or =O.

In one embodiment, $R^1$ is selected from the group consisting of 2-oxazolyl, 3-oxazolyl, 3, pyrazolyl, 2-pyridyl, 3-pyridazinyl, and 2-pyrimidinyl; wherein the 2-oxazolyl, 3-oxazolyl, 2-pyridyl, 3-pyridazinyl, and 2-pyrimidinyl may be unsubstituted or substituted by methyl, halo or =O, and the 3-pyrazolyl may be unsubstituted or substituted by ethyl.

In one embodiment, $R^1$ is selected from the group consisting of 2-oxazolyl, 3-pyrazolyl, 2-pyridyl, 3-pyridazinyl, and 2-pyrimidinyl; wherein the 2-oxazolyl, 2-pyridyl, 3-pyridazinyl, and 2-pyrimidinyl may be unsubstituted or substituted by methyl, halo or =O.

In one embodiment, $R^1$ is selected from the group consisting of 2-oxazolyl, 5-oxazolyl, 3-pyrazolyl, 2-pyridyl, 3-pyridazinyl, and 2-pyrimidinyl; wherein the 2-oxazolyl may be unsubstituted or substituted by methyl or ethyl, 5-oxazolyl may be unsubstituted or substituted by ethyl, 3-pyrazolyl may be unsubstituted or substituted by ethyl, 2-pyridyl may be unsubstituted or substituted by methyl, ethyl, halo or =O, the 3-pyridazinyl may be unsubstituted or substituted by methyl, and the 2-pyrimidinyl may be unsubstituted or substituted by methyl or halo.

In one embodiment, $R^1$ is selected from the group consisting of 2-oxazolyl, 2-pyridyl, 3-pyridazinyl, and 2-pyrimidinyl; wherein the 2-pyridyl may be unsubstituted or substituted by methyl, halo or =O and the 3-pyridazinyl may be unsubstituted or substituted by methyl.

In one embodiment, $R^1$ is selected from the group consisting of 2-oxazolyl, 2-pyridyl, 3-pyridazinyl, and 2-pyrimidinyl; wherein the 2-pyridyl may be unsubstituted or substituted by methyl, or halo and the 3-pyridazinyl may be unsubstituted or substituted by methyl.

In one embodiment, $R^1$ is selected from the group consisting of 2-oxazolyl, 2-pyridyl, 3-pyridazinyl, and 2-pyrimidinyl; wherein the 2-pyridyl may be unsubstituted or substituted by methyl, chloro or fluoro and the 3-pyridazinyl may be unsubstituted or substituted by methyl.

In one embodiment, $R^1$ is selected from the group consisting of 2-oxazolyl, 2-pyridyl, 5-methyl-2-pyridyl, 5-chloro-2-pyridyl, 5-fluoro-2-pyridyl, 3-pyridazinyl, 6-methyl-3-pyridazinyl 5-ethyl-2-pyridyl, 6-ethyl-2-pyridyl, 5-chloro-2-pyrimidinyl, 5-methyl-2-pyrimidinyl, 2-methyl-1,3-oxazol-5-yl, 4-ethyl-1,3-oxazol-2-yl, 1-ethyl-1H-pyrazol-3-yl, 5-chloro-2-pyrimidinyl and 2-pyrimidinyl.

In one embodiment, $R^1$ is selected from the group consisting of 2-oxazolyl, 2-pyridyl, 5-methyl-2-pyridyl, 5-chloro-2-pyridyl, 5-fluoro-2-pyridyl, 3-pyridazinyl, 6-methyl-3-pyridazinyl and 2-pyrimidinyl.

In one embodiment, $R^1$ is unsubstituted or substituted pyridyl.

In one embodiment, $R^1$ is 2-pyridyl.
In one embodiment, $R^1$ is unsubstituted or substituted pyridazinyl.
In one embodiment, $R^1$ is substituted pyridazinyl.
In one embodiment, $R^1$ is methylpyridazinyl.
In one embodiment, $R^1$ is 6-methylpyridazin-3-yl.
In one embodiment, $R^2$ is H.
In one embodiment, $R^2$ is methyl.
In one embodiment, $R^1$ is 2-pyridyl and $R^2$ is methyl.
In one embodiment, $R^1$ is 6-methylpyridazin-3-yl and $R^2$ is methyl.

In one embodiment, the compound of formula (I) is selected from the list consisting of:
3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl) propanoic acid;
3-(5-chloro-6-(1-(5-methylpyridin-2-yl)ethoxy)benzo[d] isoxazol-3-yl)propanoic acid;
3-(5-chloro-6-((5-fluoropyridin-2-yl)methoxy)benzo[d] isoxazol-3-yl)propanoic acid;
3-(5-chloro-6-((5-chloropyridin-2-yl)methoxy)benzo[d] isoxazol-3-yl)propanoic acid;
3-(5-chloro-6-((5-methylpyridin-2-yl)methoxy)benzo[d] isoxazol-3-yl)propanoic acid;
3-(5-chloro-6-(1-(oxazol-2-yl)ethoxy)benzo[d]isoxazol-3-yl)propanoic acid;

3-(5-chloro-6-(1-(5-fluoropyridin-2-yl)ethoxy)benzo[d]
isoxazol-3-yl)propanoic acid;
3-(5-chloro-6-(pyridazin-3-ylmethoxy)benzo[d]isoxazol-3-
yl)propanoic acid;
3-(5-chloro-6-(1-(pyrimidin-2-yl)ethoxy)benzo[d]isoxazol-
3-yl)propanoic acid;
3-(5-chloro-6-(1-(5-chloropyridin-2-yl)propoxy)benzo[d]
isoxazol-3-yl)propanoic acid;
3-(5-chloro-6-((6-methylpyridazin-3-yl)methoxy)benzo[d]
isoxazol-3-yl)propanoic acid;
3-(5-chloro-6-(1-(5-chloropyridin-2-yl)ethoxy)benzo[d]
isoxazol-3-yl)propanoic acid;
3-(5-chloro-6-(1-(6-methylpyridazin-3-yl)ethoxy)benzo[d]
isoxazol-3-yl)propanoic acid;
3-(5-chloro-6-(1-(pyridazin-3-yl)ethoxy)benzo[d]isoxazol-
3-yl)propanoic acid;
3-(5-chloro-6-(1-(5-methylpyridin-2-yl)propoxy)benzo[d]
isoxazol-3-yl)propanoic acid;
3-(5-chloro-6-(1-(pyridin-2-yl)propoxy)benzo[d]isoxazol-
3-yl)propanoic acid;
or a salt thereof.

In one embodiment, the compound of formula (I) is selected from the list consisting of:
3-{5-chloro-6-[1-(5-ethylpyridin-2-yl)ethoxy]-1,2-benzoxazol-3-yl}propanoic acid;
3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
3-{5-chloro-6-[1-(2-methyl-1,3-oxazol-5-yl)ethoxy]-1,2-benzoxazol-3-yl}propanoic acid;
3-{5-chloro-6-[1-(5-chloropyrimidin-2-yl)ethoxy]-1,2-benzoxazol-3-yl}propanoic acid;
3-{5-chloro-6-[1-(5-methylpyrimidin-2-yl)ethoxy]-1,2-benzoxazol-3-yl}propanoic acid;
3-{5-chloro-6-[1-(4-ethyl-1,3-oxazol-2-yl)ethoxy]-1,2-benzoxazol-3-yl}propanoic acid;
3-{5-chloro-6-[1-(pyrimidin-2-yl)propoxy]-1,2-benzoxazol-3-yl}propanoic acid
3-{5-chloro-6-[1-(pyridazin-3-yl)propoxy]-1,2-benzoxazol-3-yl}propanoic acid;
3-{5-chloro-6-[1-(6-methylpyridazin-3-yl)propoxy]-1,2-benzoxazol-3-yl}propanoic acid;
3-{5-chloro-6-[1-(5-methylpyrimidin-2-yl)propoxy]-1,2-benzoxazol-3-yl}propanoic acid;
3-{5-chloro-6-[1-(5-chloropyrimidin-2-yl)propoxy]-1,2-benzoxazol-3-yl}propanoic acid; and
3-(5-chloro-6-(1-(1-ethyl-1H-pyrazol-3-yl)ethoxy)benzo[d]isoxazol-3-yl)propanoic acid;
or a salt thereof In one embodiment, the compound of formula (I) is selected from the list consisting of:
3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl)propanoic acid;
3-(5-chloro-6-(1-(5-methylpyridin-2-yl)ethoxy)benzo[d]isoxazol-3-yl)propanoic acid;
3-(5-chloro-6-((5-fluoropyridin-2-yl)methoxy)benzo[d]isoxazol-3-yl)propanoic acid;
3-(5-chloro-6-((5-chloropyridin-2-yl)methoxy)benzo[d]isoxazol-3-yl)propanoic acid;
3-(5-chloro-6-((5-methylpyridin-2-yl)methoxy)benzo[d]isoxazol-3-yl)propanoic acid;
3-(5-chloro-6-(1-(oxazol-2-yl)ethoxy)benzo[d]isoxazol-3-yl)propanoic acid;
3-(5-chloro-6-(1-(5-fluoropyridin-2-yl)ethoxy)benzo[d]isoxazol-3-yl)propanoic acid;
3-(5-chloro-6-(pyridazin-3-ylmethoxy)benzo[d]isoxazol-3-yl)propanoic acid;
3-(5-chloro-6-(1-(pyrimidin-2-yl)ethoxy)benzo[d]isoxazol-3-yl)propanoic acid;
3-(5-chloro-6-(1-(5-chloropyridin-2-yl)propoxy)benzo[d]isoxazol-3-yl)propanoic acid;
3-(5-chloro-6-((6-methylpyridazin-3-yl)methoxy)benzo[d]isoxazol-3-yl)propanoic acid;
3-(5-chloro-6-(1-(5-chloropyridin-2-yl)ethoxy)benzo[d]isoxazol-3-yl)propanoic acid;
3-(5-chloro-6-(1-(6-methylpyridazin-3-yl)ethoxy)benzo[d]isoxazol-3-yl)propanoic acid;
3-(5-chloro-6-(1-(pyridazin-3-yl)ethoxy)benzo[d]isoxazol-3-yl)propanoic acid;
3-(5-chloro-6-(1-(5-methylpyridin-2-yl)propoxy)benzo[d]isoxazol-3-yl)propanoic acid;
3-(5-chloro-6-(1-(pyridin-2-yl)propoxy)benzo[d]isoxazol-3-yl)propanoic acid;
3-{5-chloro-6-[1-(5-ethylpyridin-2-yl)ethoxy]-1,2-benzoxazol-3-yl}propanoic acid;
3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
3-{5-chloro-6-[1-(2-methyl-1,3-oxazol-5-yl)ethoxy]-1,2-benzoxazol-3-yl}propanoic acid;
3-{5-chloro-6-[1-(5-chloropyrimidin-2-yl)ethoxy]-1,2-benzoxazol-3-yl}propanoic acid;
3-{5-chloro-6-[1-(5-methylpyrimidin-2-yl)ethoxy]-1,2-benzoxazol-3-yl}propanoic acid;
3-{5-chloro-6-[1-(4-ethyl-1,3-oxazol-2-yl)ethoxy]-1,2-benzoxazol-3-yl}propanoic acid;
3-{5-chloro-6-[1-(pyrimidin-2-yl)propoxy]-1,2-benzoxazol-3-yl}propanoic acid
3-{5-chloro-6-[1-(pyridazin-3-yl)propoxy]-1,2-benzoxazol-3-yl}propanoic acid;
3-{5-chloro-6-[1-(6-methylpyridazin-3-yl)propoxy]-1,2-benzoxazol-3-yl}propanoic acid;
3-{5-chloro-6-[1-(5-methylpyrimidin-2-yl)propoxy]-1,2-benzoxazol-3-yl}propanoic acid;
3-{5-chloro-6-[1-(5-chloropyrimidin-2-yl)propoxy]-1,2-benzoxazol-3-yl}propanoic acid; and
3-(5-chloro-6-(1-(1-ethyl-1H-pyrazol-3-yl)ethoxy)benzo[d]isoxazol-3-yl)propanoic acid;
3-{5-chloro-6-[1-(3-fluoropyridin-2-yl)ethoxy]-1,2-benzoxazol-3-yl}propanoic acid;
or a salt thereof In one embodiment, the compound of formula (I) is selected from the list consisting of:
(R)-3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl) propanoic acid;
(R)-3-(5-chloro-6-(1-(5-methylpyridin-2-yl)ethoxy)benzo[d]isoxazol-3-yl)propanoic acid;
(S)-3-(5-chloro-6-(1-(5-methylpyridin-2-yl)ethoxy)benzo[d]isoxazol-3-yl)propanoic acid;
3-(5-chloro-6-(1-(pyridin-2-yl)ethoxy)benzo[d]isoxazol-3-yl)propanoic acid (racemic);
3-(5-chloro-6-((5-fluoropyridin-2-yl)methoxy)benzo[d]isoxazol-3-yl)propanoic acid;

diol 3-(5-chloro-6-((5-chloropyridin-2-yl)methoxy)benzo[d]isoxazol-3-yl)propanoic acid;
3-(5-chloro-6-((5-methylpyridin-2-yl)methoxy)benzo[d]isoxazol-3-yl)propanoic acid;
(R)-3-(5-chloro-6-(1-(oxazol-2-yl)ethoxy)benzo[d]isoxazol-3-yl)propanoic acid;
(S)-3-(5-chloro-6-(1-(oxazol-2-yl)ethoxy)benzo[d]isoxazol-3-yl)propanoic acid;
(R)-3-(5-chloro-6-(1-(5-fluoropyridin-2-yl)ethoxy)benzo[d]isoxazol-3-yl)propanoic acid;
(S)-3-(5-chloro-6-(1-(5-fluoropyridin-2-yl)ethoxy)benzo[d]isoxazol-3-yl)propanoic acid;
3-(5-chloro-6-(pyridazin-3-ylmethoxy)benzo[d]isoxazol-3-yl)propanoic acid;
(R)-3-(5-chloro-6-(1-(pyrimidin-2-yl)ethoxy)benzo[d]isoxazol-3-yl)propanoic acid;
(S)-3-(5-chloro-6-(1-(pyrimidin-2-yl)ethoxy)benzo[d]isoxazol-3-yl)propanoic acid;
(R)-3-(5-chloro-6-(1-(5-chloropyridin-2-yl)ethoxy)benzo[d]isoxazol-3-yl)propanoic acid;
3-(5-chloro-6-((6-methylpyridazin-3-yl)methoxy)benzo[d]isoxazol-3-yl)propanoic acid;
(S)-3-(5-chloro-6-(1-(5-chloropyridin-2-yl)ethoxy)benzo[d]isoxazol-3-yl)propanoic acid;
(R)-3-(5-chloro-6-(1-(6-methylpyridazin-3-yl)ethoxy)benzo[d]isoxazol-3-yl)propanoic acid;
(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;
(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid;
or a salt thereof.

In one embodiment, the compound of formula (I) is selected from the list consisting of:
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid;
(S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid;
and
(S)-3-(5-chloro-6-(1-(1-ethyl-1H-pyrazol-3-yl)ethoxy)benzo[d]isoxazol-3-yl)propanoic acid;
or a salt thereof.

In one embodiment, the compound of formula (I) is selected from the list consisting of:
(R)-3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl)propanoic acid;
(R)-3-(5-chloro-6-(1-(5-methylpyridin-2-yl)ethoxy)benzo[d]isoxazol-3-yl)propanoic acid;
(S)-3-(5-chloro-6-(1-(5-methylpyridin-2-yl)ethoxy)benzo[d]isoxazol-3-yl)propanoic acid;
3-(5-chloro-6-(1-(pyridin-2-yl)ethoxy)benzo[d]isoxazol-3-yl)propanoic acid (racemic);
3-(5-chloro-6-((5-fluoropyridin-2-yl)methoxy)benzo[d]isoxazol-3-yl)propanoic acid;
diol 3-(5-chloro-6-((5-chloropyridin-2-yl)methoxy)benzo[d]isoxazol-3-yl)propanoic acid;
3-(5-chloro-6-((5-methylpyridin-2-yl)methoxy)benzo[d]isoxazol-3-yl)propanoic acid;
(R)-3-(5-chloro-6-(1-(oxazol-2-yl)ethoxy)benzo[d]isoxazol-3-yl)propanoic acid;
(S)-3-(5-chloro-6-(1-(oxazol-2-yl)ethoxy)benzo[d]isoxazol-3-yl)propanoic acid;
(R)-3-(5-chloro-6-(1-(5-fluoropyridin-2-yl)ethoxy)benzo[d]isoxazol-3-yl)propanoic acid;
(S)-3-(5-chloro-6-(1-(5-fluoropyridin-2-yl)ethoxy)benzo[d]isoxazol-3-yl)propanoic acid;
3-(5-chloro-6-(pyridazin-3-ylmethoxy)benzo[d]isoxazol-3-yl)propanoic acid;
(R)-3-(5-chloro-6-(1-(pyrimidin-2-yl)ethoxy)benzo[d]isoxazol-3-yl)propanoic acid;
(S)-3-(5-chloro-6-(1-(pyrimidin-2-yl)ethoxy)benzo[d]isoxazol-3-yl)propanoic acid;

(R)-3-(5-chloro-6-(1-(5-chloropyridin-2-yl)ethoxy)benzo[d]isoxazol-3-yl)propanoic acid;
3-(5-chloro-6-((6-methylpyridazin-3-yl)methoxy)benzo[d]isoxazol-3-yl)propanoic acid;
(S)-3-(5-chloro-6-(1-(5-chloropyridin-2-yl)ethoxy)benzo[d]isoxazol-3-yl)propanoic acid;
(R)-3-(5-chloro-6-(1-(6-methylpyridazin-3-yl)ethoxy)benzo[d]isoxazol-3-yl)propanoic acid;
(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;
(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid;
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid;
(S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid;
(S)-3-(5-chloro-6-(1-(1-ethyl-1H-pyrazol-3-yl)ethoxy)benzo[d]isoxazol-3-yl)propanoic acid;
and
3-{5-chloro-6-[(1R)-1-(3-fluoropyridin-2-yl)ethoxy]-1,2-benzoxazol-3-yl}propanoic acid;
or a salt thereof In one embodiment, the compound of formula (I) is selected from the list consisting of:
(R)-3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl)propanoic acid;
(R)-3-(5-chloro-6-(1-(5-methylpyridin-2-yl)ethoxy)benzo[d]isoxazol-3-yl)propanoic acid;
(S)-3-(5-chloro-6-(1-(5-methylpyridin-2-yl)ethoxy)benzo[d]isoxazol-3-yl)propanoic acid;
3-(5-chloro-6-(1-(pyridin-2-yl)ethoxy)benzo[d]isoxazol-3-yl)propanoic acid (racemic);
3-(5-chloro-6-((5-fluoropyridin-2-yl)methoxy)benzo[d]isoxazol-3-yl)propanoic acid;
diol 3-(5-chloro-6-((5-chloropyridin-2-yl)methoxy)benzo[d]isoxazol-3-yl)propanoic acid;
3-(5-chloro-6-((5-methylpyridin-2-yl)methoxy)benzo[d]isoxazol-3-yl)propanoic acid;
(R)-3-(5-chloro-6-(1-(oxazol-2-yl)ethoxy)benzo[d]isoxazol-3-yl)propanoic acid;
(S)-3-(5-chloro-6-(1-(oxazol-2-yl)ethoxy)benzo[d]isoxazol-3-yl)propanoic acid;
(R)-3-(5-chloro-6-(1-(5-fluoropyridin-2-yl)ethoxy)benzo[d]isoxazol-3-yl)propanoic acid;
(S)-3-(5-chloro-6-(1-(5-fluoropyridin-2-yl)ethoxy)benzo[d]isoxazol-3-yl)propanoic acid;
3-(5-chloro-6-(pyridazin-3-ylmethoxy)benzo[d]isoxazol-3-yl)propanoic acid;
(R)-3-(5-chloro-6-(1-(pyrimidin-2-yl)ethoxy)benzo[d]isoxazol-3-yl)propanoic acid;
(S)-3-(5-chloro-6-(1-(pyrimidin-2-yl)ethoxy)benzo[d]isoxazol-3-yl)propanoic acid;
(R)-3-(5-chloro-6-(1-(5-chloropyridin-2-yl)ethoxy)benzo[d]isoxazol-3-yl)propanoic acid;
3-(5-chloro-6-((6-methylpyridazin-3-yl)methoxy)benzo[d]isoxazol-3-yl)propanoic acid;
(S)-3-(5-chloro-6-(1-(5-chloropyridin-2-yl)ethoxy)benzo[d]isoxazol-3-yl)propanoic acid;
(R)-3-(5-chloro-6-(1-(6-methylpyridazin-3-yl)ethoxy)benzo[d]isoxazol-3-yl)propanoic acid;
(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;

(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid;
or a pharmaceutically acceptable salt thereof.

In one embodiment, the compound of formula (I) is selected from the list consisting of:
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid;
(S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid; and
(S)-3-(5-chloro-6-(1-(1-ethyl-1H-pyrazol-3-yl)ethoxy)benzo[d]isoxazol-3-yl)propanoic acid;
or a pharmaceutically acceptable salt thereof.

In one embodiment, the compound of formula (I) is selected from the list consisting of:
(R)-3-(5-chloro-6-(1-(pyridin-2-yl)ethoxy)benzo[d]isoxazol-3-yl)propanoic acid;
3-(5-chloro-6-(pyridin-2-ylmethoxy)benzo[d]isoxazol-3-yl)propanoic acid;
(R)-3-(5-chloro-6-(1-(5-methylpyridin-2-yl)ethoxy)benzo[d]isoxazol-3-yl)propanoic acid;
(S)-3-(5-chloro-6-(1-(5-methylpyridin-2-yl)ethoxy)benzo[d]isoxazol-3-yl)propanoic acid;
3-(5-chloro-6-(1-(pyridin-2-yl)ethoxy)benzo[d]isoxazol-3-yl)propanoic acid (racemic);
3-(5-chloro-6-((5-fluoropyridin-2-yl)methoxy)benzo[d]isoxazol-3-yl)propanoic acid;
diol 3-(5-chloro-6-((5-chloropyridin-2-yl)methoxy)benzo[d]isoxazol-3-yl)propanoic acid;
3-(5-chloro-6-((5-methylpyridin-2-yl)methoxy)benzo[d]isoxazol-3-yl)propanoic acid;
(R)-3-(5-chloro-6-(1-(oxazol-2-yl)ethoxy)benzo[d]isoxazol-3-yl)propanoic acid;
(S)-3-(5-chloro-6-(1-(oxazol-2-yl)ethoxy)benzo[d]isoxazol-3-yl)propanoic acid;
(R)-3-(5-chloro-6-(1-(5-fluoropyridin-2-yl)ethoxy)benzo[d]isoxazol-3-yl)propanoic acid;
(S)-3-(5-chloro-6-(1-(5-fluoropyridin-2-yl)ethoxy)benzo[d]isoxazol-3-yl)propanoic acid;
3-(5-chloro-6-(pyridazin-3-ylmethoxy)benzo[d]isoxazol-3-yl)propanoic acid;
(R)-3-(5-chloro-6-(1-(pyrimidin-2-yl)ethoxy)benzo[d]isoxazol-3-yl)propanoic acid;
(S)-3-(5-chloro-6-(1-(pyrimidin-2-yl)ethoxy)benzo[d]isoxazol-3-yl)propanoic acid;
(R)-3-(5-chloro-6-(1-(5-chloropyridin-2-yl)ethoxy)benzo[d]isoxazol-3-yl)propanoic acid;
3-(5-chloro-6-((6-methylpyridazin-3-yl)methoxy)benzo[d]isoxazol-3-yl)propanoic acid;
(S)-3-(5-chloro-6-(1-(5-chloropyridin-2-yl)ethoxy)benzo[d]isoxazol-3-yl)propanoic acid;
(R)-3-(5-chloro-6-(1-(6-methylpyridazin-3-yl)ethoxy)benzo[d]isoxazol-3-yl)propanoic acid;
(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;
(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid;
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;

3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid;
(S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid;
(S)-3-(5-chloro-6-(1-(1-ethyl-1H-pyrazol-3-yl)ethoxy)benzo[d]isoxazol-3-yl)propanoic acid;
and
3-{5-chloro-6-[(1R)-1-(3-fluoropyridin-2-yl)ethoxy]-1,2-benzoxazol-3-yl}propanoic acid;
or a pharmaceutically acceptable salt thereof.

In one embodiment, the compound of formula (I) is selected from the list consisting of:
(R)-3-(5-chloro-6-(1-(pyridin-2-yl)ethoxy)benzo[d]isoxazol-3-yl)propanoic acid;
(R)-3-(5-chloro-6-(1-(pyridin-2-yl)ethoxy)benzo[d]isoxazol-3-yl) propanoic acid, tris(hydroxymethyl)aminomethane) salt;
(R)-3-(5-chloro-6-(1-(pyridin-2-yl)ethoxy)benzo[d]isoxazol-3-yl)propanoic acid compound with sulfuric acid (1:1);
sodium (R)-3-(5-chloro-6-(1-(pyridin-2-yl)ethoxy)benzo[d]isoxazol-3-yl)propanoate;
(R)-3-(5-chloro-6-(1-(pyridin-2-yl)ethoxy)benzo[d]isoxazol-3-yl)propanoic acid compound with (S)-2-amino-5-guanidinopentanoic acid (1:1);
(R)-3-(5-chloro-6-(1-(pyridin-2-yl)ethoxy)benzo[d]isoxazol-3-yl)propanoic acid compound with (S)-2,6-diaminohexanoic acid (1:1);
(R)-3-(5-chloro-6-(1-(pyridin-2-yl)ethoxy)benzo[d]isoxazol-3-yl)propanoic acid hydrochloride;
(2R,3R,4R,5S)-6-(methylamino)hexane-1,2,3,4,5-pentanol (R)-3-(5-chloro-6-(1-(pyridin-2-yl)ethoxy)benzo[d]isoxazol-3-yl)propanoate;
(R)-3-(5-chloro-6-(1-(pyridin-2-yl)ethoxy)benzo[d]isoxazol-3-yl)propanoic acid compound with methanesulfonic acid (1:1);
N-benzyl-2-phenylethanamine (R)-3-(5-chloro-6-(1-(pyridin-2-yl)ethoxy)benzo[d]isoxazol-3-yl)propanoate;
$N^1,N^2$-dibenzylethane-1,2-diamine (R)-3-(5-chloro-6-(1-(pyridin-2-yl)ethoxy)benzo[d]isoxazol-3-yl)propanoate (1:2);
$N^1$-(2-aminoethyl)ethane-1,2-diamine (R)-3-(5-chloro-6-(1-(pyridin-2-yl)ethoxy)benzo[d]isoxazol-3-yl)propanoate (1:3);
(R)-3-(5-chloro-6-(1-(pyridin-2-yl)ethoxy)benzo[d]isoxazol-3-yl)propanoic acid compound with 4-methylbenzenesulfonic acid (1:1);
2-amino-2-(hydroxymethyl)propane-1,3-diol 3-(5-chloro-6-(pyridin-2-ylmethoxy)benzo[d]isoxazol-3-yl)propanoate;
2-amino-2-(hydroxymethyl)propane-1,3-diol (R)-3-(5-chloro-6-(1-(5-methylpyridin-2-yl)ethoxy)benzo[d]isoxazol-3-yl)propanoate;
2-amino-2-(hydroxymethyl)propane-1,3-diol (S)-3-(5-chloro-6-(1-(5-methylpyridin-2-yl)ethoxy)benzo[d]isoxazol-3-yl)propanoate;
3-(5-chloro-6-(1-(pyridin-2-yl)ethoxy)benzo[d]isoxazol-3-yl)propanoic acid (racemic);
2-amino-2-(hydroxymethyl)propane-1,3-diol 3-(5-chloro-6-((5-fluoropyridin-2-yl)methoxy)benzo[d]isoxazol-3-yl)propanoate;
2-amino-2-(hydroxymethyl)propane-1,3-diol 3-(5-chloro-6-((5-chloropyridin-2-yl)methoxy)benzo[d]isoxazol-3-yl)propanoate;
2-amino-2-(hydroxymethyl)propane-1,3-diol 3-(5-chloro-6-((5-methylpyridin-2-yl)methoxy)benzo[d]isoxazol-3-yl)propanoate;
2-amino-2-(hydroxymethyl)propane-1,3-diol (R)-3-(5-chloro-6-(1-(oxazol-2-yl)ethoxy)benzo[d]isoxazol-3-yl)propanoate;
2-amino-2-(hydroxymethyl)propane-1,3-diol (S)-3-(5-chloro-6-(1-(oxazol-2-yl)ethoxy)benzo[d]isoxazol-3-yl)propanoate;
2-amino-2-(hydroxymethyl)propane-1,3-diol (R)-3-(5-chloro-6-(1-(5-fluoropyridin-2-yl)ethoxy)benzo[d]isoxazol-3-yl)propanoate;
2-amino-2-(hydroxymethyl)propane-1,3-diol (S)-3-(5-chloro-6-(1-(5-fluoropyridin-2-yl)ethoxy)benzo[d]isoxazol-3-yl)propanoate;
3-(5-chloro-6-(pyridazin-3-ylmethoxy)benzo[d]isoxazol-3-yl)propanoic acid;
2-amino-2-(hydroxymethyl)propane-1,3-diol (R)-3-(5-chloro-6-(1-(pyrimidin-2-yl)ethoxy)benzo[d]isoxazol-3-yl)propanoate;
2-amino-2-(hydroxymethyl)propane-1,3-diol (S)-3-(5-chloro-6-(1-(pyrimidin-2-yl)ethoxy)benzo[d]isoxazol-3-yl)propanoate;
2-amino-2-(hydroxymethyl)propane-1,3-diol (R)-3-(5-chloro-6-(1-(5-chloropyridin-2-yl)ethoxy)benzo[d]isoxazol-3-yl)propanoate;
3-(5-chloro-6-((6-methylpyridazin-3-yl)methoxy)benzo[d]isoxazol-3-yl)propanoic acid;
2-amino-2-(hydroxymethyl)propane-1,3-diol (S)-3-(5-chloro-6-(1-(5-chloropyridin-2-yl)ethoxy)benzo[d]isoxazol-3-yl)propanoate;
(R)-3-(5-chloro-6-(1-(6-methylpyridazin-3-yl)ethoxy)benzo[d]isoxazol-3-yl)propanoic acid;

(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;
(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid.

In one embodiment, the compound of formula (I) is selected from the list consisting of:
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid;
(S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid;
and
(S)-3-(5-chloro-6-(1-(1-ethyl-1H-pyrazol-3-yl)ethoxy)benzo[d]isoxazol-3-yl)propanoic acid.

In one embodiment, the compound of formula (I) is selected from the list consisting of:
(R)-3-(5-chloro-6-(1-(pyridin-2-yl)ethoxy)benzo[d]isoxazol-3-yl)propanoic acid;
(R)-3-(5-chloro-6-(1-(pyridin-2-yl)ethoxy)benzo[d]isoxazol-3-yl) propanoic acid, tris(hydroxymethyl)aminomethane) salt;
(R)-3-(5-chloro-6-(1-(pyridin-2-yl)ethoxy)benzo[d]isoxazol-3-yl)propanoic acid compound with sulfuric acid (1:1);
sodium (R)-3-(5-chloro-6-(1-(pyridin-2-yl)ethoxy)benzo[d]isoxazol-3-yl)propanoate;
(R)-3-(5-chloro-6-(1-(pyridin-2-yl)ethoxy)benzo[d]isoxazol-3-yl)propanoic acid compound with (S)-2-amino-5-guanidinopentanoic acid (1:1);
(R)-3-(5-chloro-6-(1-(pyridin-2-yl)ethoxy)benzo[d]isoxazol-3-yl)propanoic acid compound with (S)-2,6-diaminohexanoic acid (1:1);
(R)-3-(5-chloro-6-(1-(pyridin-2-yl)ethoxy)benzo[d]isoxazol-3-yl)propanoic acid hydrochloride;
(2R,3R,4R,5S)-6-(methylamino)hexane-1,2,3,4,5-pentanol (R)-3-(5-chloro-6-(1-(pyridin-2-yl)ethoxy)benzo[d]isoxazol-3-yl)propanoate;
(R)-3-(5-chloro-6-(1-(pyridin-2-yl)ethoxy)benzo[d]isoxazol-3-yl)propanoic acid compound with methanesulfonic acid (1:1);
N-benzyl-2-phenylethanamine (R)-3-(5-chloro-6-(1-(pyridin-2-yl)ethoxy)benzo[d]isoxazol-3-yl)propanoate;
$N^1,N^2$-dibenzylethane-1,2-diamine (R)-3-(5-chloro-6-(1-(pyridin-2-yl)ethoxy)benzo[d]isoxazol-3-yl)propanoate (1:2);
$N^1$-(2-aminoethyl)ethane-1,2-diamine (R)-3-(5-chloro-6-(1-(pyridin-2-yl)ethoxy)benzo[d]isoxazol-3-yl)propanoate (1:3);
(R)-3-(5-chloro-6-(1-(pyridin-2-yl)ethoxy)benzo[d]isoxazol-3-yl)propanoic acid compound with 4-methylbenzenesulfonic acid (1:1);
2-amino-2-(hydroxymethyl)propane-1,3-diol 3-(5-chloro-6-(pyridin-2-ylmethoxy)benzo[d]isoxazol-3-yl)propanoate;
2-amino-2-(hydroxymethyl)propane-1,3-diol (R)-3-(5-chloro-6-(1-(5-methylpyridin-2-yl)ethoxy)benzo[d]isoxazol-3-yl)propanoate;
2-amino-2-(hydroxymethyl)propane-1,3-diol (S)-3-(5-chloro-6-(1-(5-methylpyridin-2-yl)ethoxy)benzo[d]isoxazol-3-yl)propanoate;
3-(5-chloro-6-(1-(pyridin-2-yl)ethoxy)benzo[d]isoxazol-3-yl)propanoic acid (racemic);
2-amino-2-(hydroxymethyl)propane-1,3-diol 3-(5-chloro-6-((5-fluoropyridin-2-yl)methoxy)benzo[d]isoxazol-3-yl)propanoate;
2-amino-2-(hydroxymethyl)propane-1,3-diol 3-(5-chloro-6-((5-chloropyridin-2-yl)methoxy)benzo[d]isoxazol-3-yl)propanoate;
2-amino-2-(hydroxymethyl)propane-1,3-diol 3-(5-chloro-6-((5-methylpyridin-2-yl)methoxy)benzo[d]isoxazol-3-yl)propanoate;

2-amino-2-(hydroxymethyl)propane-1,3-diol (R)-3-(5-chloro-6-(1-(oxazol-2-yl)ethoxy)benzo[d]isoxazol-3-yl)propanoate;
2-amino-2-(hydroxymethyl)propane-1,3-diol (S)-3-(5-chloro-6-(1-(oxazol-2-yl)ethoxy)benzo[d]isoxazol-3-yl)propanoate;
2-amino-2-(hydroxymethyl)propane-1,3-diol (R)-3-(5-chloro-6-(1-(5-fluoropyridin-2-yl)ethoxy)benzo[d]isoxazol-3-yl)propanoate;
2-amino-2-(hydroxymethyl)propane-1,3-diol (S)-3-(5-chloro-6-(1-(5-fluoropyridin-2-yl)ethoxy)benzo[d]isoxazol-3-yl)propanoate;
3-(5-chloro-6-(pyridazin-3-ylmethoxy)benzo[d]isoxazol-3-yl)propanoic acid;
2-amino-2-(hydroxymethyl)propane-1,3-diol (R)-3-(5-chloro-6-(1-(pyrimidin-2-yl)ethoxy)benzo[d]isoxazol-3-yl)propanoate;
2-amino-2-(hydroxymethyl)propane-1,3-diol (S)-3-(5-chloro-6-(1-(pyrimidin-2-yl)ethoxy)benzo[d]isoxazol-3-yl)propanoate;
2-amino-2-(hydroxymethyl)propane-1,3-diol (R)-3-(5-chloro-6-(1-(5-chloropyridin-2-yl)ethoxy)benzo[d]isoxazol-3-yl)propanoate;
3-(5-chloro-6-((6-methylpyridazin-3-yl)methoxy)benzo[d]isoxazol-3-yl)propanoic acid;
2-amino-2-(hydroxymethyl)propane-1,3-diol (S)-3-(5-chloro-6-(1-(5-chloropyridin-2-yl)ethoxy)benzo[d]isoxazol-3-yl)propanoate;
(R)-3-(5-chloro-6-(1-(6-methylpyridazin-3-yl)ethoxy)benzo[d]isoxazol-3-yl)propanoic acid;
(S)-3-(5-chloro-6-(1-(6-methylpyridazin-3-yl)ethoxy)benzo[d]isoxazol-3-yl)propanoic acid;
(R)-3-(5-chloro-6-(1-(pyridazin-3-yl)ethoxy)benzo[d]isoxazol-3-yl)propanoic acid;
(S)-3-(5-chloro-6-(1-(pyridazin-3-yl)ethoxy)benzo[d]isoxazol-3-yl)propanoic acid;
(R)-3-(5-chloro-6-(1-(5-methylpyridin-2-yl)propoxy)benzo[d]isoxazol-3-yl)propanoic acid;
(S)-3-(5-chloro-6-(1-(5-methylpyridin-2-yl)propoxy)benzo[d]isoxazol-3-yl)propanoic acid;
(R)-3-(5-chloro-6-(1-(pyridin-2-yl)propoxy)benzo[d]isoxazol-3-yl)propanoic acid;
(S)-3-(5-chloro-6-(1-(pyridin-2-yl)propoxy)benzo[d]isoxazol-3-yl)propanoic acid;
(R)-3-(5-chloro-6-(1-(5-chloropyridin-2-yl)propoxy)benzo[d]isoxazol-3-yl)propanoic acid; and
(S)-3-(5-chloro-6-(1-(5-chloropyridin-2-yl)propoxy)benzo[d]isoxazol-3-yl)propanoic acid.
(R)-3-{5-chloro-6-[1-(5-ethylpyridin-2-yl)ethoxy]-1,2-benzoxazol-3-yl}propanoic acid;
(S)-3-{5-chloro-6-[1-(5-ethylpyridin-2-yl)ethoxy]-1,2-benzoxazol-3-yl}propanoic acid;
(R)-3-{5-chloro-6-[1-(6-ethylpyridin-2-yl)ethoxy]-1,2-benzoxazol-3-yl}propanoic acid;
(S)-3-{5-chloro-6-[1-(6-ethylpyridin-2-yl)ethoxy]-1,2-benzoxazol-3-yl}propanoic acid;
3-{5-chloro-6-[(5-chloropyrimidin-2-yl)methoxy]-1,2-benzoxazol-3-yl}propanoic acid;
3-{5-chloro-6-[(5-methylpyrimidin-2-yl)methoxy]-1,2-benzoxazol-3-yl}propanoic acid;
(R)-3-{5-chloro-6-[1-(2-methyl-1,3-oxazol-5-yl)ethoxy]-1,2-benzoxazol-3-yl}propanoic acid;
(S)-3-{5-chloro-6-[1-(2-methyl-1,3-oxazol-5-yl)ethoxy]-1,2-benzoxazol-3-yl}propanoic acid;
(R)-3-{5-chloro-6-[1-(5-chloropyrimidin-2-yl)ethoxy]-1,2-benzoxazol-3-yl}propanoic acid;
(S)-3-{5-chloro-6-[1-(5-chloropyrimidin-2-yl)ethoxy]-1,2-benzoxazol-3-yl}propanoic acid;
(R)-3-{5-chloro-6-[1-(5-methylpyrimidin-2-yl)ethoxy]-1,2-benzoxazol-3-yl}propanoic acid;
(S)-3-{5-chloro-6-[1-(5-methylpyrimidin-2-yl)ethoxy]-1,2-benzoxazol-3-yl}propanoic acid;
(R)-3-{5-chloro-6-[1-(4-ethyl-1,3-oxazol-2-yl)ethoxy]-1,2-benzoxazol-3-yl}propanoic acid;
(S)-3-{5-chloro-6-[1-(4-ethyl-1,3-oxazol-2-yl)ethoxy]-1,2-benzoxazol-3-yl}propanoic acid;
(R)-3-{5-chloro-6-[1-(pyrimidin-2-yl)propoxy]-1,2-benzoxazol-3-yl}propanoic acid;
(S)-3-{5-chloro-6-[1-(pyrimidin-2-yl)propoxy]-1,2-benzoxazol-3-yl}propanoic acid;
(R)-3-{5-chloro-6-[1-(pyridazin-3-yl)propoxy]-1,2-benzoxazol-3-yl}propanoic acid;
(S)-3-{5-chloro-6-[1-(pyridazin-3-yl)propoxy]-1,2-benzoxazol-3-yl}propanoic acid;
(R)-3-{5-chloro-6-[1-(6-methylpyridazin-3-yl)propoxy]-1,2-benzoxazol-3-yl}propanoic acid;
(S)-3-{5-chloro-6-[1-(6-methylpyridazin-3-yl)propoxy]-1,2-benzoxazol-3-yl}propanoic acid;
(R)-3-{5-chloro-6-[1-(5-methylpyrimidin-2-yl)propoxy]-1,2-benzoxazol-3-yl}propanoic acid;
(S)-3-{5-chloro-6-[1-(5-methylpyrimidin-2-yl)propoxy]-1,2-benzoxazol-3-yl}propanoic acid;
(R)-3-{5-chloro-6-[1-(5-chloropyrimidin-2-yl)propoxy]-1,2-benzoxazol-3-yl}propanoic acid; (S)-3-{5-chloro-6-[1-(5-chloropyrimidin-2-yl)propoxy]-1,2-benzoxazol-3-yl}propanoic acid;
(R)-3-(5-chloro-6-(1-(1-ethyl-1H-pyrazol-3-yl)ethoxy)benzo[d]isoxazol-3-yl)propanoic acid;
(S)-3-(5-chloro-6-(1-(1-ethyl-1H-pyrazol-3-yl)ethoxy)benzo[d]isoxazol-3-yl)propanoic acid;
and
3-{5-chloro-6-[(1R)-1-(3-fluoropyridin-2-yl)ethoxy]-1,2-benzoxazol-3-yl}propanoic acid.

In one embodiment, the compound of formula (I) is: 3-(5-chloro-6-(1-(pyridin-2-yl)ethoxy)benzo[d]isoxazol-3-yl)propanoic acid or a salt thereof.

In one embodiment, the compound of formula (I) is: 3-(5-chloro-6-(1-(pyridin-2-yl)ethoxy)benzo[d]isoxazol-3-yl)propanoic acid or a pharmaceutically acceptable salt thereof.

In one embodiment, the compound of formula (I) is: 3-(5-chloro-6-(1-(pyridin-2-yl)ethoxy)benzo[d]isoxazol-3-yl)propanoic acid.

In one embodiment, the compound of formula (I) is: 3-(5-chloro-6-(1-(pyridin-2-yl)ethoxy)benzo[d]isoxazol-3-yl)propanoic acid in the form of a pharmaceutically acceptable salt.

In one embodiment, the compound of formula (I) is: (R)-3-(5-chloro-6-(1-(pyridin-2-yl)ethoxy)benzo[d]isoxazol-3-yl)propanoic acid or a salt thereof.

In one embodiment, the compound of formula (I) is: (R)-3-(5-chloro-6-(1-(pyridin-2-yl)ethoxy)benzo[d]isoxazol-3-yl)propanoic acid or a pharmaceutically acceptable salt thereof.

In one embodiment, the compound of formula (I) is: (R)-3-(5-chloro-6-(1-(pyridin-2-yl)ethoxy)benzo[d]isoxazol-3-yl)propanoic acid.

In one embodiment, the compound of formula (I) is: (R)-3-(5-chloro-6-(1-(pyridin-2-yl)ethoxy)benzo[d]isoxazol-3-yl)propanoic acid in the form of a pharmaceutically acceptable salt.

In one embodiment, the compound of formula (I) is 3-(5-chloro-6-(1-(6-methylpyridazin-3-yl)ethoxy)benzo[d]isoxazol-3-yl)propanoic acid or a salt thereof.

In one embodiment, the compound of formula (I) is 3-(5-chloro-6-(1-(6-methylpyridazin-3-yl)ethoxy)benzo[d]isoxazol-3-yl)propanoic acid or a pharmaceutically acceptable salt thereof.

In one embodiment, the compound of formula (I) is 3-(5-chloro-6-(1-(6-methylpyridazin-3-yl)ethoxy)benzo[d]isoxazol-3-yl)propanoic acid.

In one embodiment, the compound of formula (I) is 3-(5-chloro-6-(1-(6-methylpyridazin-3-yl)ethoxy)benzo[d]isoxazol-3-yl)propanoic acid in the form of a pharmaceutically acceptable salt.

In one embodiment, the compound of formula (I) is (R)-3-(5-chloro-6-(1-(6-methylpyridazin-3-yl)ethoxy)benzo[d]isoxazol-3-yl)propanoic acid or a salt thereof.

In one embodiment, the compound of formula (I) is (R)-3-(5-chloro-6-(1-(6-methylpyridazin-3-yl)ethoxy)benzo[d]isoxazol-3-yl)propanoic acid or a pharmaceutically acceptable salt thereof.

In one embodiment, the compound of formula (I) is (R)-3-(5-chloro-6-(1-(6-methylpyridazin-3-yl)ethoxy)benzo[d]isoxazol-3-yl)propanoic acid.

In one embodiment, the compound of formula (I) is (R)-3-(5-chloro-6-(1-(6-methylpyridazin-3-yl)ethoxy)benzo[d]isoxazol-3-yl)propanoic acid in the form of a pharmaceutically acceptable salt.

In one embodiment, the pharmaceutically acceptable salt is an ethanolamine salt.

Terms and Definitions

Compounds of formula (I) and salts thereof are referred to hereinafter as "Compounds of the invention".

The term "halogen" or "halo" as used herein refers to fluorine (F), chlorine (Cl), bromine (Br), or iodine (I). Examples of suitable halogens are fluorine and chlorine.

The term "heteroaryl" as used herein refers to a 5- or 6-membered aromatic ring which comprises one or more (e.g. 1, 2 or 3) heteroatoms independently selected from O, N or S. For example, when "heteroaryl" represents a 5-membered ring, the ring contains a heteroatom selected from O, N or S and may optionally contain 1 to 3 further nitrogen atoms (e.g. may further contain one, two or three nitrogen atoms). When "heteroaryl" represents a 6-membered ring, the ring may contain from 1 to 3 nitrogen atoms. Examples of such 5- or 6-membered heteroaryl rings include, but are not limited to, pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

'Enantiomeric excess' (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

'Enantiomerically enriched' refers to products whose enantiomeric excess (ee) is greater than zero. For example, 'enantiomerically enriched' refers to products whose enantiomeric excess is greater than 50% ee, greater than 75% ee, and greater than 90% ee.

'Enantiomerically pure' refers to products whose enantiomeric excess is 99% or greater.

Included within the scope of the compounds of the invention are all solvates (including hydrates), complexes, polymorphs, radiolabelled derivatives, and stereoisomers of the compounds of formula (I) and salts thereof.

Included within the scope of the compounds of the invention are all solvates (including hydrates), complexes, polymorphs, prodrugs, radiolabelled derivatives, and stereoisomers of the compounds of formula (I) and salts thereof.

Prodrugs of the compounds of the invention are included within the scope of the present invention. In one embodiment, the compounds of the invention are not prodrugs.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987 and in D. Fleishner, S. Ramon and H. Barba "Improved oral drug delivery: solubility limitations overcome by the use of prodrugs", Advanced Drug Delivery Reviews (1996) 19(2) 115-130. Prodrugs are any covalently bonded carriers that release a compound of formula (I) in vivo when such prodrug is administered to a patient. Prodrugs are generally prepared by modifying functional groups in a way such that the modification is cleaved in vivo yielding the parent compound. Prodrugs may include, for example, compounds of the invention wherein the carboxylic acid group is bonded to any group that, when administered to a patient, cleaves to form the carboxylic acid group. Thus, representative examples of prodrugs include (but are not limited to) phosphonate, carbamate, acetate, formate and benzoate derivatives of the carboxylic acid functional group of the compounds of the invention.

The compounds of the invention are capable of forming base addition salts. Such salts can be formed by reaction with the appropriate base, optionally is a suitable solvent such as an organic solvent, to give the salt which can be isolated by crystallisation and filtration.

The compounds of the invention are also capable of forming acid addition salts. Such salts can be formed by reaction with the appropriate acid, optionally in a suitable solvent such as an organic solvent, to give the salt which can be isolated by crystallisation and filtration.

It is to be understood that the references herein to compounds of formula (I) and salts thereof covers the compounds of formula (I) as free bases, free acids or as salts thereof, for example as pharmaceutically acceptable salts thereof. Thus, in one embodiment, the invention is directed to compounds of formula (I) as the free base. In another embodiment, the invention is directed to compounds of formula (I) as the free acid. In another embodiment, the invention is directed to compounds of formula (I) and salts thereof. In a further embodiment, the invention is directed to compounds of formula (I) and pharmaceutically acceptable salts thereof.

Because of their potential use in medicine, it will be appreciated that for use in medicine the salts of the compounds of the invention should be pharmaceutically acceptable. As used herein the term 'pharmaceutically acceptable salts' refers to salts that retain the desired biological activity of the subject compound and exhibit minimal undesired toxicological effect. Pharmaceutically acceptable salts will be apparent to those skilled in the art and include those described in Berge, J. Pharm. Sci., 1977, 66, 1-19.

Pharmaceutically acceptable base salts include, but are not limited to, ammonium salts, alkali metal salts such as those of sodium and potassium, alkaline earth metal salts such as those of calcium and magnesium and salts with organic bases, including salts of primary, secondary and tertiary amines, such as t-butylamine, cyclohexylamine, dimethylamine, trimethylamine, diethyltriamine, 2-amino-2-(hydroxymethyl)-1,3-propanediol (TRIS), ethanolamine and N-methyl-D-glucamine.

Pharmaceutically acceptable base addition salts include, but are not limited to, ammonium salts, alkali metal salts such as those of sodium and potassium, alkaline earth metal salts such as those of calcium and magnesium and salts with organic bases, including salts of primary, secondary and tertiary amines, such as t-butylamine, cyclohexylamine, dimethylamine, trimethylamine, diethyltriamine, 2-amino-2-(hydroxymethyl)-1,3-propanediol (TRIS), ethanolamine, choline and N-methyl-D-glucamine.

Pharmaceutically acceptable acid salts include, but are not limited to, hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, and 2,5-dihydroxybenzoate.

Pharmaceutically acceptable acid addition salts include, but are not limited to, hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, and 2,5-dihydroxybenzoate.

In one embodiment, the salt is a pharmaceutically acceptable salt.

In one embodiment, the pharmaceutically acceptable salt is an ethanolamine salt.

Certain compounds of the invention are capable of existing in sterioisomeric forms. It will be understood that the invention encompasses all geometric and optical isomers of these compounds and the mixtures thereof including racemates. The different stereoisomeric forms may be separated one from the other by methods known in the art (e.g. separation by chiral HPLC) or any given stereoisomer may be obtained by stereospecific or asymmetric synthesis. The invention also extends to any tautomeric forms and mixtures thereof.

Certain compounds of the invention may contain an asymmetric centre (also referred to as a chiral centre) and may, therefore, exist as individual enantiomers, or as mixtures thereof. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

In one aspect, there is provided a compound of formula (I) wherein $R_2$ is not H, and wherein the (R) enantiomer is present in greater than 90% enantiomeric excess ("ee").

In one embodiment, the (R) enantiomer is present in greater than 95% ee.

In one embodiment, the (R) enantiomer is present in greater than 99% ee.

The invention includes within its scope all possible stoichiometric and non-stoichiometric forms of the salts of the compounds of formula (I).

Certain compounds of the invention may exist in the form of solvates. As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. If the solvent used is water, the solvate may be referred to as a hydrate.

It will be further appreciated that certain compounds of the invention that exist in crystalline form, including the various solvates thereof, may exhibit polymorphism (i.e. the capacity to occur in different crystalline structures). These different crystalline forms are typically known as 'polymorphs'. The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds of formula (I) and salts thereof may be isotopically-labelled and as such are identical to compounds of the invention, but for one or more atoms having been replaced by an atom having an atomic mass or mass number different from the atomic mass or mass number most commonly found in nature. Examples of isotopes that can be incorporated into compounds of the invention are isotopes of hydrogen, carbon, nitrogen, fluorine, such as $^3$H, $^{11}$C, $^{14}$C and $^{18}$F. Such isotopically-labelled compounds are useful in drug and/or substrate tissue distribution assays. For example, $^{11}$C and $^{18}$F isotopes are particularly useful in PET (positron emission tomography). PET is useful in brain imaging. Isotopically labelled compounds of the invention can generally be prepared by carrying out the procedures disclosed below, by substituting a readily available isotopically labelled reagent for a non-isotopically labelled reagent.

Abbreviations conc. concentrated
DCM dichloromethane
DEAD diethylazodicarboxylate
DMF N,N-dimethylformamide
DMSO dimethylsulphoxide
ESI electrospray ionisation
h hour(s)
HEPES 4-(2-hydroxyethyl)-1-piperazineethanesulphonic acid
HOBt 1-hydroxybenzotriazole
HPLC high performance liquid chromatography
LCMS liquid chromatography-mass spectrometry
MeCN acetonitrile
min minutes
mL millilitre
Ms/mesyl methanesulphonyl
NMR nuclear magnetic resonance
R-CBS (R)-3,3-diphenyl-1-methylpyrrolidino[1,2-c]-1,3,2-oxazaborole
RT room temperature
Rt retention time
SFC supercritical fluid chromatography
THF tetrahydrofuran
TFA trifluoroacetic acid
TRIS 2-amino-2-(hydroxymethyl)-1,3-propanediol Compound Preparation Compounds of the invention (wherein $R^1$ and $R^2$ are as hereinbefore defined) may be synthesised substantially according to Reaction Scheme 1 by treatment of ethyl 3-(5-chloro-6-hydroxybenzo[d]isoxazol-3-yl)propanoate (IIIa) (a compound of formula (III) wherein R is ethyl) or methyl 3-(5-chloro-6-hydroxybenzo[d]isoxazol-3-yl)propanoate (IIIb) (a compound of formula (III) wherein R is methyl) with CH($R^1$)($R^2$)OMs of formula (IV) in the absence of coupling reagents, or with CH($R^1$)($R^2$)OH of formula (V) in the presence of coupling reagents, followed by the saponification or acid-mediated hydrolysis of the resultant ester of formula (II).

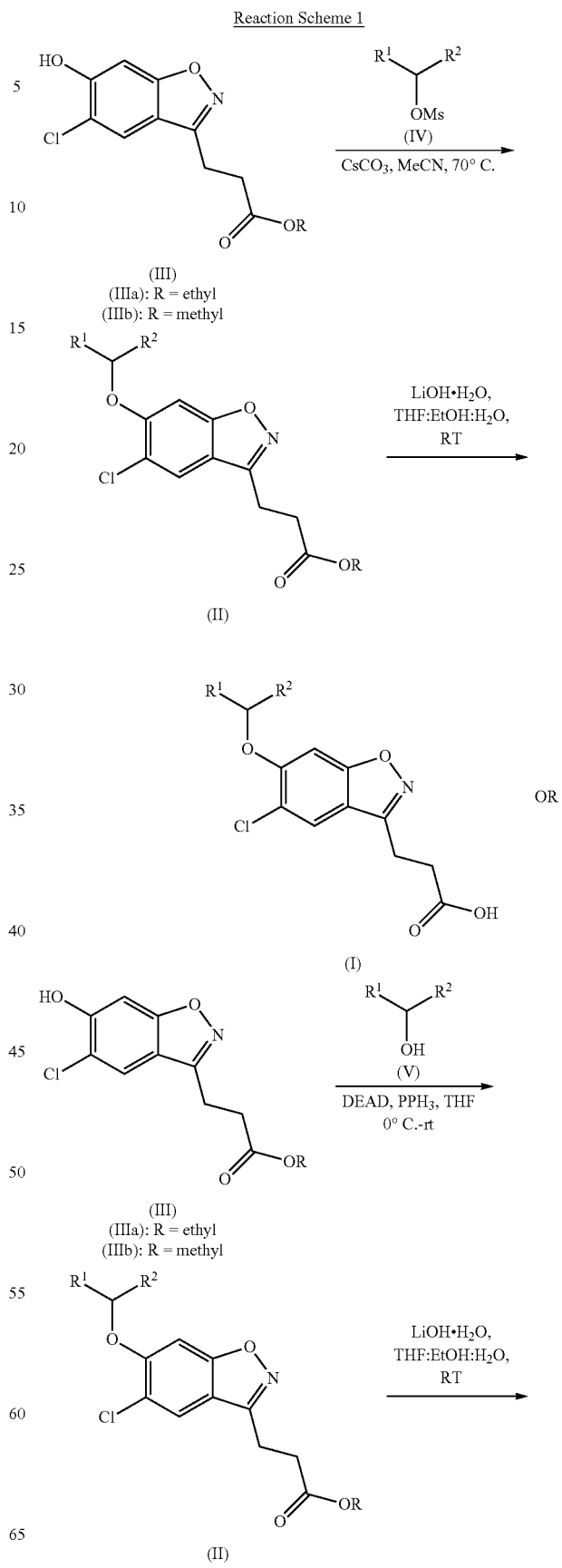

Reaction Scheme 1

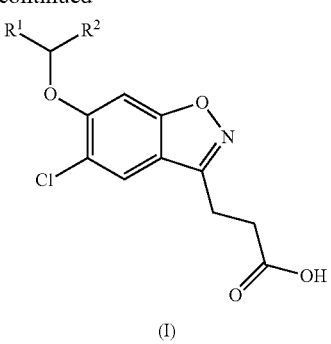
(I)
The alkyl 3-(5-chloro-6-hydroxybenzo[d]isoxazol-3-yl)propanoates of formula (III) can be synthesised substantially according to Reaction Schemes 2 and 3 starting from 4-chlororesorcinol.
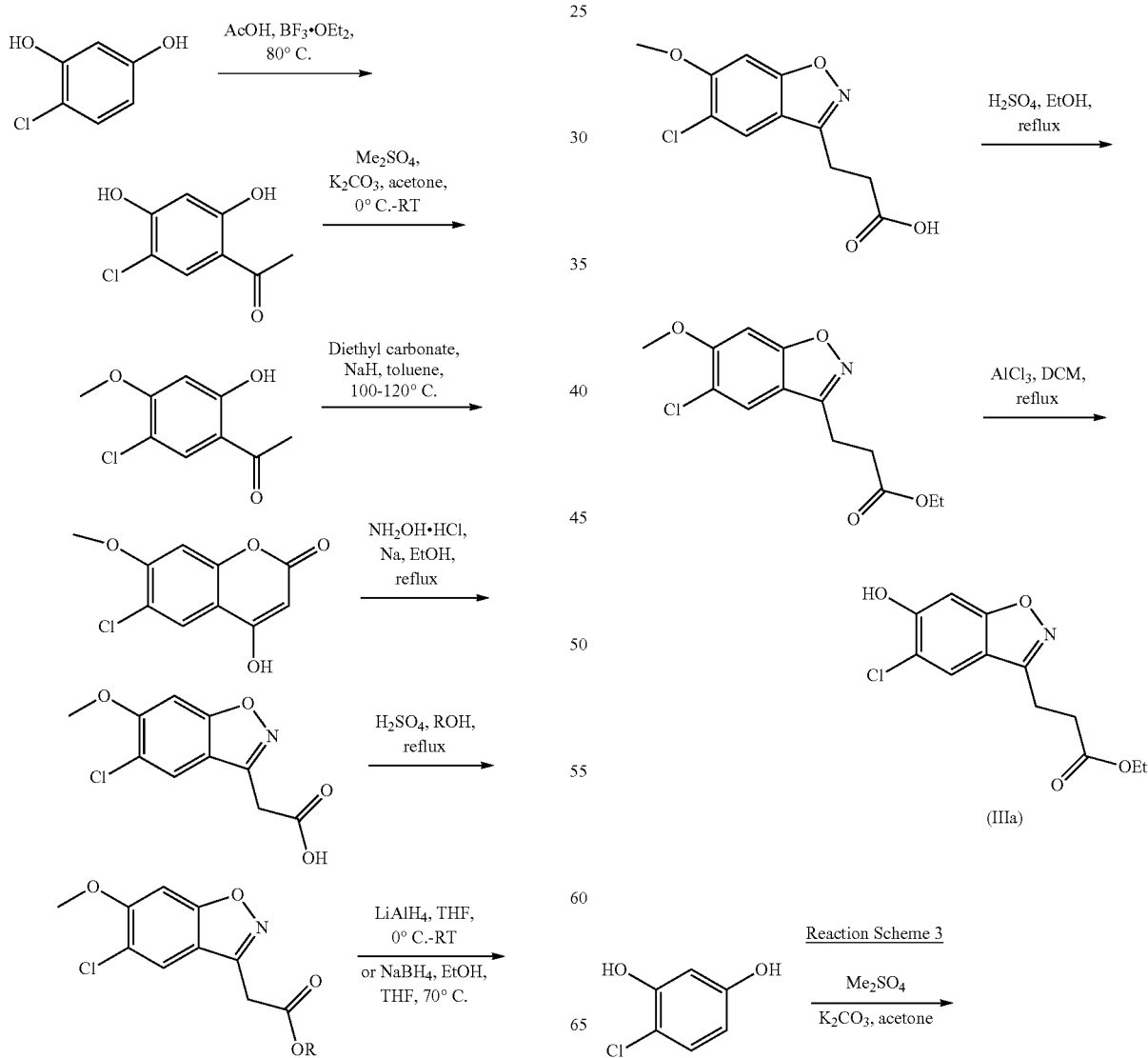
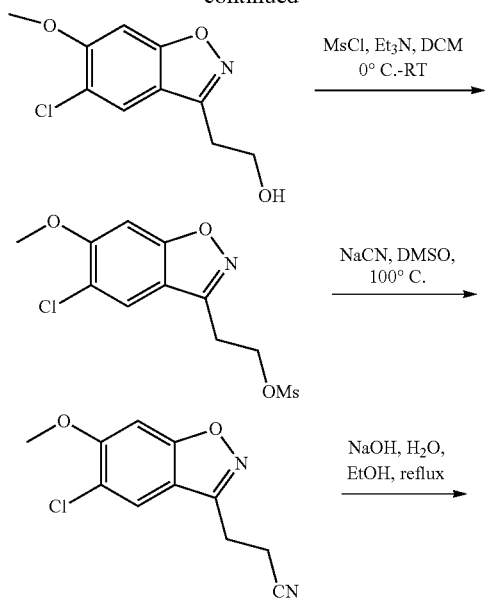

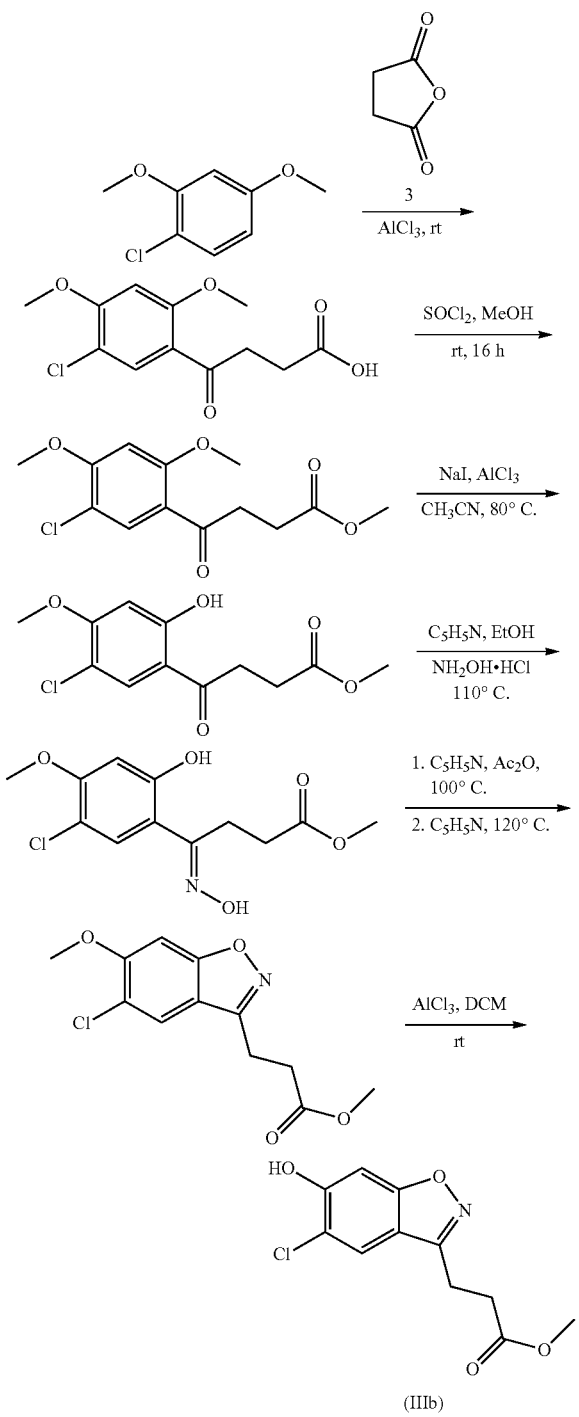

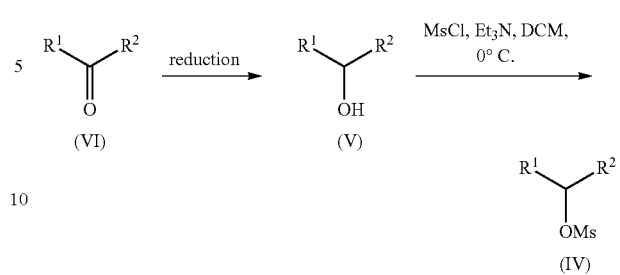

Reaction Scheme 4

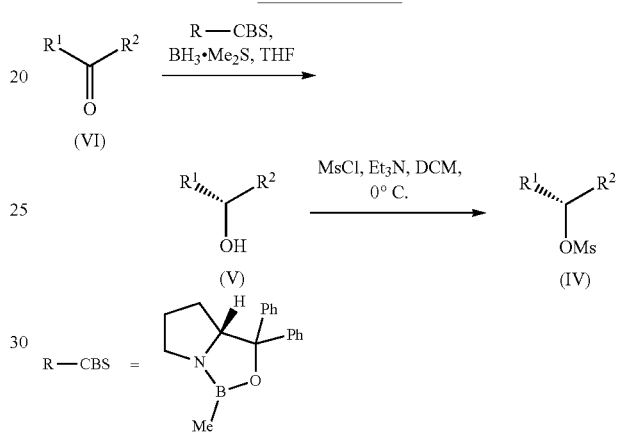

Reaction Scheme 5

Alternatively, the mesylate of formula (IV) can be synthesised substantially according to Reaction Scheme 6 from the carboxylic acid of formula (IX). Treatment of the carboxylic acid of formula (IX) with N,O-dimethylhydroxylamine in the presence of suitable coupling agents, for instance HOBT and EDCI, to afford the Weinreb amide of formula (VII), followed by treatment with the Grignard reagent of formula (VIII) affords the ketone of formula (VI). Reduction of the ketone of formula (VI) with a suitable reducing agent, for instance sodium borohydride ($NaBH_4$) affords the achiral alcohol (V), which may be optionally activated, for instance as the mesylate of formula (IV) by introduction of a suitable activating group, for instance mesylate, by treatment with an activating agent, for instance by treatment with mesyl chloride (MsCl), in a suitable solvent, for instance dichloromethane (DCM), using a suitable base, for instance triethylamine ($Et_3N$), at a suitable temperature, for instance ambient temperature.

The mesylate $CH(R^1)(R^2)OMs$ of formula (IV) can be synthesised from the racemic alcohol of formula (V), obtained from reduction of the aldehyde or ketone of formula (VI), substantially according to Reaction Scheme 4 (to produce racemic activated alcohol) or from the chiral alcohol of formula (V) obtained from chiral deduction of the ketone of formula (VI) substantially according to Reaction Scheme 5 (to produce chirally enriched activated alcohol).

Reaction Scheme 6

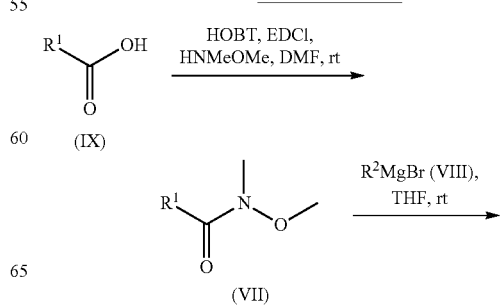

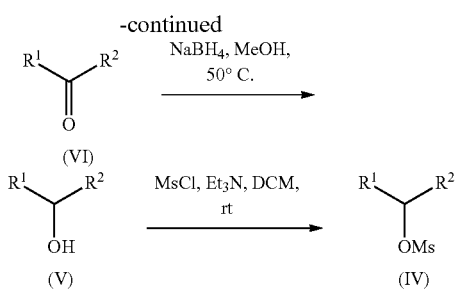

Alternatively, the mesylate of formula (IV) may be synthesised substantially according to Reaction Scheme 7, by treatment of the cyano compound of formula (X) with a Grignard reagent of formula (VIII) in a suitable solvent, for instance THF, at a suitable temperature, for instance 0° C., to afford the ketone or aldehyde of formula (VI).

Reduction of the aldehyde or ketone of formula (VI) under achiral conditions, for instance using sodium borohydride (NaBH$_4$) in a suitable solvent, for instance methanol (MeOH), affords the achiral alcohol of formula (V).

Reduction of the ketone of formula (VI) (R$_2$ is not H) under chiral conditions, for instance using R-CBS ((R)-3,3-diphenyl-1-methylpyrrolidino[1,2-c]-1,3,2-oxazaborole) and borane-dimethylsulphide in a suitable solvent, for instance THF, affords the chiral alcohol (VA).

The achiral alcohol of formula (V) or chiral alcohol of formula (VA) may be optionally activated, for instance as the corresponding mesylate of formula (IV) or formula (IVA) by introduction of a suitable activating group, for instance mesyate, by treatment with an activating agent, for instance by treatment with mesyl chloride (MsCl), in a suitable solvent, for instance dichloromethane (DCM), using a suitable base, for instance triethylamine (Et$_3$N), at a suitable temperature, for instance ambient temperature.

Wiley (1981)", can be used. For example, primary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluroroacetic acid in a suitable solvent such as dichloromethane, diethylether, 1,4-dioxane, isopropanol or mixtures thereof.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulfate, or anhydrous sodium sulfate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate, methanol, ethanol, or butanol, or aqueous mixtures thereof. It will be appreciated that specific reaction times and temperatures may typically be determined by reaction-monitoring techniques, for example thin-layer chromatography and LCMS.

General Methods

Unless stated otherwise, starting materials were commercially available. All solvents and commercial reagents were of laboratory grade and were used as received.

Reaction Scheme 7

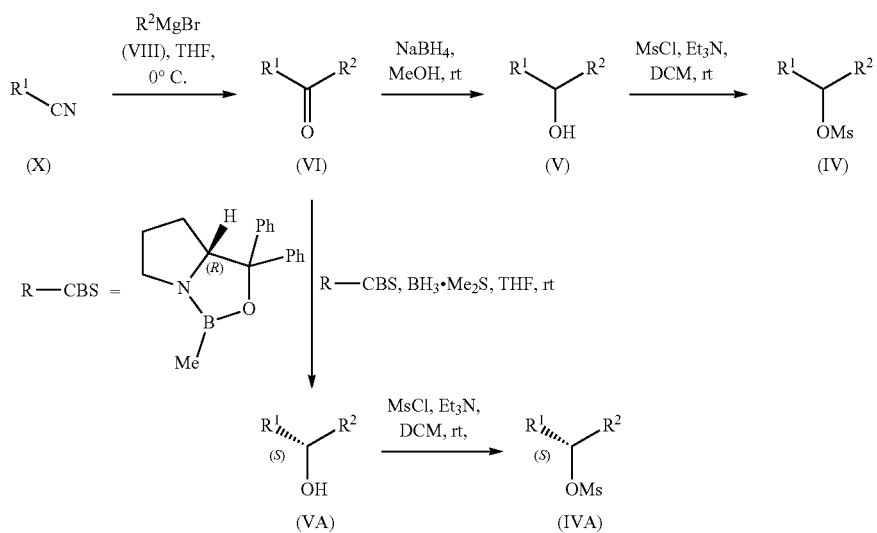

It will be appreciated by those skilled in the art that it may be necessary to protect certain reactive substituents during some of the above procedures. Standard protection and deprotection techniques, such as those described in "Greene T.W. Protective groups in organic synthesis, New York, Where diasteroisomers are represented and only the relative stereochemistry is referred to, or where an enantiomer is represented and the absolute stereochemistry is unknown, the bold or hashed solid bond symbols are used (▬/⦀⦀⦀). Alternatively, where diasteroisomers are represented and only the relative stereochemistry is referred to, or where an enantiomer is represented and the absolute stereochemistry is unknown, the use of "or1" at the chiral centre denotes that the absolute stereochemistry of the particular compound is unknown, i.e. the compound as drawn may be either the R enantiomer or the S enantiomer. Where the absolute stereochemistry is known and the compound is a single enantiomer, the bold or hashed wedge symbol ( —— ·······) are used as appropriate, without the use of "or1" at the chiral centre.

Analytical Methods
LCMS Methods

| Method | Description |
|---|---|
| A | Column: Acquity BEH C18 (50 mm × 2.1 mm, 1.7 μm)<br>Mobile Phase: A: 0.1% Formic acid in water;<br>B: 0.1% Formic acid in MeCN<br>Time (min)/% B: 0/3, 0.4/3, 3.2/98, 3.8/98, 4.2/3, 4.5/3<br>Column Temp: 35° C.<br>Flow Rate: 0.6 mL/min |
| B | Column: Acquity BEH C18 (50 mm × 2.1 mm, 1.7 μm)<br>Mobile Phase: A: 0.1% Formic acid in water;<br>B: 0.1% Formic acid in MeCN<br>Time (min)/% B: 0/3, 1.5/100, 1.9/100, 2/3.<br>Column Temp: 40° C.<br>Flow Rate: 1.0 mL/min |
| C | Column: X Bridge C18 (50 mm × 4.6 mm, 2.5 μm)<br>Mobile Phase: C: MeCN; D: 5 mM Ammonium Acetate in water<br>Time (min)/% C: 0/5, 0.5/5, 1/15, 3.3/98, 5.2/98, 5.5/5, 6/5.<br>Column Temp: 35° C.<br>Flow Rate: 1.3 mL/min |
| D | Column: X Bridge C18 (50 mm × 4.6 mm, 2.5 μm)<br>Mobile Phase: A: 5 mM Ammonium bicarbonate in water (pH ~10); B: MeCN<br>Time (min)/% B: 0/5, 0.5/5, 1/15, 3.3/98, 5.2/98, 5.5/5, 6/5.<br>Column Temp: 35° C.<br>Flow Rate: 1.3 mL/min |
| E | Column: Acquity BEH C18 (100 mm × 2.1 mm, 1.7 μm)<br>Mobile Phase: A: 0.1% TFA in water; B: 0.1% TFA in MeCN<br>Time (min)/% B: 0/2, 8.5/99, 9.5/99, 9.6/2, 10.5/2, 10.01/3.<br>Column Temp: 50° C.<br>Flow Rate: 0.5 mL/min |

LCMS Method I
Agilent 1200-6110,
Signal table: Signal A: 214 nm, Signal B: 254 nm;
Column Temperature: 40° C.
Column: HALO C18 4.6*50 mm, 2.7 μm

| Solvents | Gradient | Polarity |
|---|---|---|
| Solvent A: H$_2$O<br>(0.1% formic acid)<br>Solvent B: CH$_3$CN<br>(0.1% formic acid) | 0.00 min: A: 95.0% B: 5.0%<br>1.00 min: A: 5.0% B: 95.0%<br>2.00 min: A: 5.0% B: 95.0%<br>2.01 min: A: 95.0% B: 5.0%<br>2.50 min: A: 95.0% B: 5.0% | Positive |

HPLC Method

| Method | Description |
|---|---|
| F | Column: XBridge C18 (150 mm × 4.6 mm, 3.5 μm)<br>Mobile Phase: A: 10 mM Ammonium Acetate in water; B: 100% MeCN<br>Time (min)/% B: 0/5, 1.5/5, 3/15, 7/55, 10/95, 14/95, 17/5, 20/5.<br>Column Temp: 35° C.<br>Flow Rate: 1.0 mL/min<br>Diluent: 70:30 (MeCN:H$_2$O) |

Chiral SFC Method

| Method | Description |
|---|---|
| G | Column: CHIRALPAK IA (250 mm × 4.6 mm, 5 μm)<br>Eluent: A: CO$_2$ = 60%; B: Methanol = 40%;<br>Back pressure: 100 bar;<br>Temp: 26° C.<br>Flow Rate: 4 g/min |
| H | Column: CHIRALPAK AD-H (250 mm × 4.6 mm, 5 μm)<br>Eluent: A: CO$_2$ = 60%; B: 0.5% DEA in methanol = 40%;<br>Back pressure: 100 bar;<br>Temp: 26° C.<br>Flow Rate: 5 g/min |

Chiral SFC Data

| Example no. | Chiral Purity (%) | Retention Time (min) | Enantiomeric excess (% ee) | Chiral SFC Method |
|---|---|---|---|---|
| 1i | 99.99 | 1.82 | 99.99 | G |
| 3 | 99.35 | 1.64 | 100 | H |
| 4 | 99.49 | 16.61 | 99.31 | H |
| 9 | 99.82 | 1.73 | 99.64 | H |
| 8 | 99.90 | 12.81 | 99.81 | H |
| 11 | 99.95 | 1.48 | 99.90 | H |
| 12 | 99.50 | 2.97 | 99.00 | H |
| 14 | 99.02 | 4.32 | 98.66 | H |
| 15 | 98.44 | 2.18 | 97.81 | H |

The names of the intermediates and examples have been obtained using the compound naming programme within "ChemBioDraw Ultra v12", or alternatively using "ACD Name Pro 6.02".

Intermediates

Intermediate 1:
1-(5-chloro-2,4-dihydroxyphenyl)ethanone

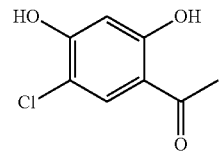

To a stirred solution of 4-chlororesorcinol (30.0 g, 208.3 mmol) in boron trifluoride diethyl ether complex (150 mL) was added glacial acetic acid (20 mL) drop wise at 0 CC. The reaction mixture was heated to 80° C. and maintained for 2 days. After complete consumption of the starting material, the reaction mixture was cooled, poured into 10% aqueous sodium acetate solution and stirred for 1 h. The solid precipitated was filtered, dried under vacuum for 1 h, washed with diethyl ether and dried under vacuum to afford 1-(5-chloro-2,4-dihydroxyphenyl)ethanone (18.0 g, 47%) as an off-white solid.

$^1$H NMR (400 MHz, DMSO-d$_6$): δ12.32 (s, 1H), 11.39 (s, 1H), 7.88 (s, 1H), 6.47 (s, 1H), 2.55 (s, 3H); LCMS (ESI): m/z 185/187 [M−H]$^-$; Rt=1.83 min; method A.

Intermediate 1a (Intermediate 1 alternative preparation): 1-(5-chloro-2,4-dihydroxyphenyl)ethanone

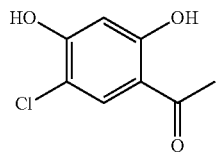

To a stirred solution of 4-chlororesorcinol (1.0 Kg, 6.92 mol) in boron trifluoride diethyl ether complex (4 L) was added glacial acetic acid (411 mL). The reaction mixture was heated at 80° C. with stirring for 2 days. After complete consumption of the starting material, the reaction mixture was cooled to 0° C., poured into 10% aqueous sodium acetate solution and stirred for 12 h. The solid precipitated was isolated by filtration, washed with diethyl ether (100 mL) and dried under vacuum (~44 h) to afford 1-(5-chloro-2,4-dihydroxyphenyl)ethanone (860 g, 66%) as an off-white solid.

$^1$H NMR (400 MHz, CDCl$_3$): δ 12.46 (s, 1H), 7.70 (s, 1H), 6.60 (s, 1H), 6.00 (s, 1H), 2.56 (s, 3H); LCMS (ESI): m/z 185/187 [M−H]$^-$; Rt=2.80 min; method C.

Intermediate 2: 1-(5-chloro-2-hydroxy-4-methoxyphenyl)ethanone

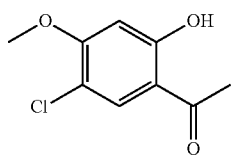

To a stirred solution of 1-(5-chloro-2,4-dihydroxyphenyl)ethanone (for example as prepared for Intermediate 1) (6.0 g, 32.2 mmol) in acetone (100 mL) was added potassium carbonate (5.11 g, 37.0 mmol) and maintained at RT for 10 min. To this, dimethyl sulfate (3.07 mL, 32.2 mmol), was added and allowed to stir at RT for 2 days. After complete consumption of the starting material, the reaction mixture was filtered and the filtrate concentrated under reduced pressure to afford the crude, which was purified by silica gel (100-200 mesh) column chromatography using 3% ethyl acetate in petroleum ether to afford 1-(5-chloro-2-hydroxy-4-methoxyphenyl)ethanone (4.20 g, 65%) as a white solid.

$^1$H NMR (400 MHz, CDCl$_3$): δ 12.65 (s, 1H), 7.69 (s, 1H), 6.48 (s, 1H), 3.93 (s, 3H), 2.56 (s, 3H); LCMS (ESI): m/z 199/201 [M−H]$^-$; Rt=1.05 min; method B.

Intermediate 2a (Intermediate 2 alternative preparation) 1-(5-chloro-2-hydroxy-4-methoxyphenyl)ethanone

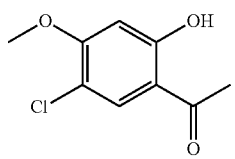

To a stirred solution of 1-(5-chloro-2,4-dihydroxyphenyl)ethanone (for example as prepared for Intermediate 1a) (860 g, 4.61 mol) in acetone (5 L) were added potassium carbonate (763 g, 5.53 mol) and dimethyl sulfate (446 mL, 4.61 mol) at 0° C. and allowed to stir at RT for 2 days. After completion of the starting material, the reaction solution was filtered and concentrated under reduced pressure. The crude product was purified by triturated with 10% DCM in hexane (1.5 L; stirred for 1 h at 10° C.). The solid obtained was filtered, washed with hexane and dried under vacuum to afford 1-(5-chloro-2-hydroxy-4-methoxyphenyl)ethanone (800 g, 86%) as an off-white solid.

$^1$H NMR (400 MHz, DMSO-d$_6$): δ 12.52 (s, 1H), 7.94 (s, 1H), 6.69 (s, 1H), 3.91 (s, 3H), 2.58 (s, 3H); LCMS (ESI): m/z 199/201[M−H]$^-$; Rt=3.62 min; method D.

Intermediate 3: 6-chloro-4-hydroxy-7-methoxy-2H-chromen-2-one

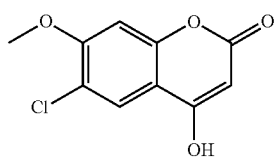

To a stirred solution of sodium hydride (60% in mineral oil; 7.4 g, 187 mmol) in toluene (300 mL) was added a solution of 1-(5-chloro-2-hydroxy-4-methoxyphenyl)ethanone (for example as prepared for Intermediate 2) (13.0 g, 65 mmol) in toluene (200 mL). After 30 min, diethyl carbonate (15.3 g, 130 mmol) was added and warmed to 120° C. for 2 days. After completion of the reaction, the reaction mixture was diluted with water and extracted with ethyl acetate. The separated aqueous layer was acidified with dilute hydrochloric acid solution to pH~2. The precipitated solid was filtered and dried under vacuum to afford 6-chloro-4-hydroxy-7-methoxy-2H-chromen-2-one (9.0 g, 61%) as a white solid.

$^1$H NMR (400 MHz, DMSO-d$_6$): δ12.56 (s, 1H), 7.76 (s, 1H), 7.20 (s, 1H), 5.49 (s, 1H), 3.95 (s, 3H); LCMS (ESI): m/z 227/229 [M$^+$]; Rt=0.85 min; method B.

Intermediate 3a (Intermediate 3 alternative preparation): 6-chloro-4-hydroxy-7-methoxy-2H-chromen-2-one

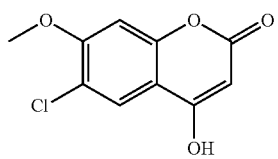

To a stirred solution of sodium hydride (60% in mineral oil; 246.5 g, 6.16 mol) in toluene (1 L) was added a solution of 1-(5-chloro-2-hydroxy-4-methoxyphenyl)ethanone (for example as prepared for Intermediate 2a) (300 g, 1.49 mol) in toluene (1 L) under inert atmosphere. After 30 min at 10° C., diethyl carbonate (292 mL, 2.41 mol) was added at 10° C. The reaction mixture was heated and stirred at 100° C. for 24 h. After completion of the reaction, the solution was allowed to cool to RT, diluted with ice-cold water and acidified with 6N aqueous hydrochloric acid (to pH~2). The solid precipitate was filtered and dried under vacuum to afford 6-chloro-4-hydroxy-7-methoxy-2H-chromen-2-one (300 g, 88%) as a white solid.

$^1$H NMR (400 MHz, DMSO-d$_6$): δ 12.60 (bs, 1H; D$_2$O exchangeable), 7.76 (s, 1H), 7.19 (s, 1H), 5.50 (s, 1H), 3.95 (s, 3H); LCMS (ESI): m/z 227/279 [M$^+$]; Rt=1.93 min; method A.

Intermediate 4: 2-(5-chloro-6-methoxybenzo[d]isoxazol-3-yl)acetic acid

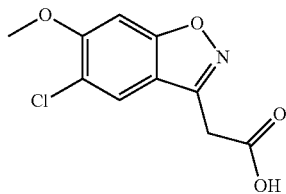 [SMILES: COc1cc2onc(CC(=O)O)c2cc1Cl]

To a freshly prepared solution of sodium ethoxide in ethanol (3.05 g of sodium metal dissolved in ethanol (200 mL)) was added hydroxylamine hydrochloride (9.1 g, 131.1 mmol) and 6-chloro-4-hydroxy-7-methoxy-2H-chromen-2-one (for example as prepared for Intermediate 3) (3.0 g, 13.2 mmol) under inert atmosphere. The reaction was stirred and heated at reflux (95° C.) for 6 days. After complete conversion of the starting material, the reaction mixture was concentrated under reduced pressure. The obtained residue was diluted with water, washed with ethyl acetate and then acidified with dilute hydrochloric acid solution (up to pH~1). A solid precipitated was filtered and dried under vacuum to afford 2-(5-chloro-6-methoxybenzo[d]isoxazol-3-yl)acetic acid (2.0 g, 62%) as an off-white solid. $^1$H NMR (400 MHz, DMSO-d$_6$): δ 12.91 (s, 1H), 7.97 (s, 1H), 7.55 (s, 1H), 4.05 (s, 2H), 3.97 (s, 3H); LCMS (ESI): m/z 242/244 [M$^+$]; Rt=1.82 min; method A.

Intermediate 4a (Intermediate 4 alternative preparation): 2-(5-chloro-6-methoxybenzo[d]isoxazol-3-yl)acetic acid

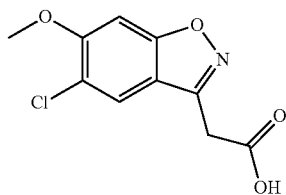 [SMILES: COc1cc2onc(CC(=O)O)c2cc1Cl]

To a stirred solution of hydroxylamine hydrochloride (143 g, 2.20 mol) in ethanol (1.5 L) was added sodium ethoxide (150 g, 2.20 mol) at 0-10° C. under inert atmosphere. To this, 6-chloro-4-hydroxy-7-methoxy-2H-chromen-2-one (for example as prepared for Intermediate 3a) (100 g, 441.3 mmol) was added at same temperature. The reaction mixture was heated at ~80° C. and stirred for 16 h. After complete conversion of the starting material, the reaction mixture was concentrated under reduced pressure. The obtained residue was diluted with water. The resultant solution was acidified with 2N hydrochloric acid (up to pH~2) and stirred for 1 h. The solid precipitate was filtered and dried under vacuum (~4 h) to afford 2-(5-chloro-6-methoxybenzo[d]isoxazol-3-yl)acetic acid (60 g, 56%) as an off-white solid.

$^1$H NMR (400 MHz, DMSO-d$_6$): δ 12.85 (s, 1H; D$_2$O exchangeable), 7.95 (s, 1H), 7.53 (s, 1H), 4.04 (s, 2H), 3.97 (s, 3H); LCMS (ESI): m/z 242/244 [M+H$^+$]; Rt=2.24 min; method C.

Intermediate 5: methyl 2-(5-chloro-6-methoxybenzo[d]isoxazol-3-yl)acetate

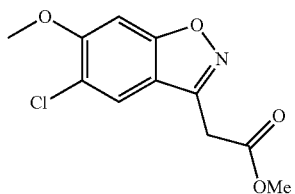 [SMILES: COC(=O)Cc1noc2cc(OC)c(Cl)cc12]

To a stirred solution of 2-(5-chloro-6-methoxybenzo[d]isoxazol-3-yl)acetic acid ((for example as prepared for Intermediate 4) (2.0 g, 8.2 mmol) in methanol (100 mL) was added a solution of conc. sulphuric acid (2 mL) in methanol (100 mL) at RT and heated to reflux and then maintained for 4 h. After complete consumption of the starting material, the reaction mixture was concentrated under reduced pressure. The obtained residue was neutralized with saturated aqueous NaHCO$_3$ solution and extracted with ethyl acetate. The combined organic extracts were dried over anhydrous sodium sulfate and concentrated under reduced pressure to afford methyl 2-(5-chloro-6-methoxybenzo[d]isoxazol-3-yl)acetate (2.0 g, 95%) as a brown solid.

$^1$H NMR (400 MHz, CDCl$_3$): δ 7.69 (s, 1H), 7.07 (s, 1H), 3.99 (m, 5H), 3.77 (s, 3H); LCMS (ESI): m/z 256/258 [M$^+$]; Rt=2.15 min; method A.

Intermediate 6: 2-(5-chloro-6-methoxybenzo[d]isoxazol-3-yl)ethanol

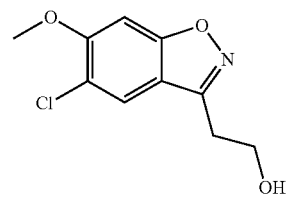

To a stirred solution of lithium aluminium hydride (15.6 mL, 1 M in THF solution) was added a solution of methyl 2-(5-chloro-6-methoxybenzo[d]isoxazol-3-yl)acetate ((for example as prepared for Intermediate 5) (2.0 g, 7.8 mmol) in THF (100 mL) at 0° C. The reaction was allowed to warm to RT and stirred for 4 h. After complete consumption of the starting material, the reaction mixture was quenched with ethyl acetate followed by aqueous sodium sulfate solution over a period of 30 min. The resultant heterogeneous mixture was filtered through a Celite™ pad. The organic layer was separated, dried over anhydrous sodium sulfate and evaporated under reduced pressure. The crude product was purified by silica gel (100-200 mesh) column chromatography using 25% ethyl acetate in petroleum ether to afford 2-(5-chloro-6-methoxybenzo[d]isoxazol-3-yl)ethanol (0.8 g, 44%) as an off-white solid.

¹H NMR (400 MHz, DMSO-d₆): δ 8.01 (s, 1H), 7.49 (s, 1H), 4.86 (t, J=5.3 Hz, 1H; D₂O exchangeable), 3.96 (s, 3H), 3.80 (td, J=6.4, 5.3 Hz, 2H), 3.06 (t, J=6.4 Hz, 2H); LCMS (ESI): m/z 228/230 [M+H⁺]; 94.1%; Rt=2.94 min; method C.

Intermediate 6a (Intermediate 6 alternative preparation): 2-(5-chloro-6-methoxybenzo[d]isoxazol-3-yl)ethanol

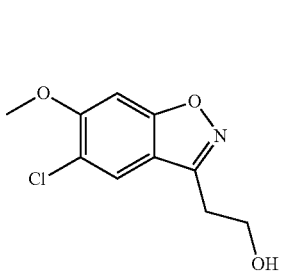

To a stirred solution of ethyl 2-(5-chloro-6-methoxybenzo[d]isoxazol-3-yl)acetate (for example as prepared for Intermediate 14) (60 g, 223 mmol) in ethanol (1.3 L) and THF (300 mL) was added sodium borohydride (16.87 g, 446 mmol) at 0° C. under inert atmosphere. The reaction was heated at 60-70° C. for 4 h. After complete consumption of the starting material, the volatiles were removed under reduced pressure to obtain the residue. The residue was diluted with ice-cold water and extracted with ethyl acetate (3×500 mL). The combined organic extracts were washed with brine, dried over anhydrous sodium sulfate and concentrated under reduced pressure to afford the crude product, which was purified by trituration with pentane and hexane to afford 2-(5-chloro-6-methoxybenzo[d]isoxazol-3-yl)ethanol (44.3 g, 88%) as a brown solid.

¹H NMR (400 MHz, DMSO-d₆): δ 8.01 (s, 1H), 7.49 (s, 1H), 4.85 (t, J=5.3 Hz, 1H; D₂O exchangeable), 3.96 (s, 3H), 3.80 (td, J=6.3, 5.1 Hz, 2H), 3.06 (t, J=6.3 Hz, 2H); LCMS (ESI): m/z 228/230 [M+H⁺]; Rt=3.31 min; method D.

Intermediate 7: 2-(5-chloro-6-methoxybenzo[d]isoxazol-3-yl)ethyl methanesulfonate

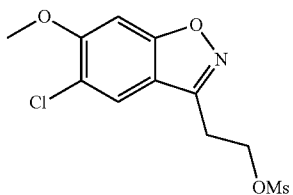 [SMILES: COc1cc2onc(CCOS(C)(=O)=O)c2cc1Cl]

To a stirred solution of 2-(5-chloro-6-methoxybenzo[d]isoxazol-3-yl)ethanol (for example as prepared for Intermediate 6) (0.8 g, 3.5 mmol) in DCM (60 mL) was added mesyl chloride (0.32 mL, 4.2 mmol) and triethylamine (1.82 mL, 14.0 mmol) at 0° C. The reaction was allowed to warm to RT and stirred for 16 h. After completion, the reaction mixture was diluted with water. The organic layer was separated, dried over anhydrous sodium sulfate and evaporated under reduced pressure to afford 2-(5-chloro-6-methoxybenzo[d]isoxazol-3-yl)ethyl methanesulfonate (1.0 g, crude) as an off-white solid, which was directly taken for next reaction without purification.

¹H NMR (400 MHz, DMSO-d₆): δ 8.11 (s, 1H), 7.54 (s, 1H), 4.61 (t, J=6.0 Hz, 2H), 3.96 (s, 3H), 3.40 (t, J=6.0 Hz, 2H), 3.16 (s, 3H).

Intermediate 7a (Intermediate 7 alternative preparation): 2-(5-chloro-6-methoxybenzo[d]isoxazol-3-yl)ethyl methanesulfonate

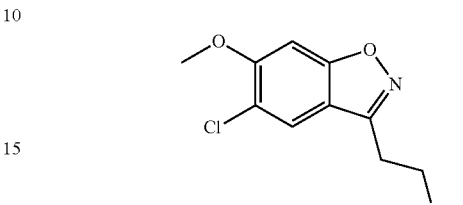

To a stirred solution of 2-(5-chloro-6-methoxybenzo[d]isoxazol-3-yl)ethanol (for example as prepared for Intermediate 6a) (44.3 g, 195.1 mmol) in DCM (520 mL) was added triethylamine (78.8 g, 780.6 mmol) and mesyl chloride (44.4 g, 390.3 mmol) at 0° C. The reaction was stirred for 16 h. After completion of the reaction, the reaction mixture was diluted with water and extracted with ethyl acetate. The combined organic extracts were dried over anhydrous sodium sulfate and evaporated under reduced pressure to afford the crude product, which was purified by trituration with hexane to afford 2-(5-chloro-6-methoxybenzo[d]isoxazol-3-yl)ethyl methanesulfonate (54 g, 90%) as a brown solid.

¹H NMR (400 MHz, DMSO-d₆): δ 8.09 (s, 1H), 7.53 (s, 1H), 4.61 (t, J=6.3 Hz, 2H), 3.97 (s, 3H), 3.41 (t, J=6.3 Hz, 2H), 3.16 (s, 3H); LCMS (ESI): m/z 306/308 [M+H⁺]; Rt=3.27 min; method C.

Intermediate 8: 3-(5-chloro-6-methoxybenzo[d]isoxazol-3-yl)propanenitrile

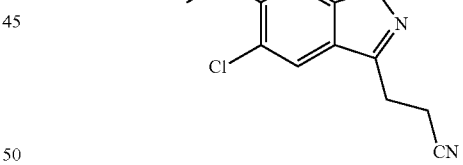

To a stirred solution of 2-(5-chloro-6-methoxybenzo[d]isoxazol-3-yl)ethyl methanesulfonate (for example as prepared for Intermediate 7) (1.0 g, 3.27 mmol) in DMSO (100 mL) was added sodium cyanide (1.6 g, 32.7 mmol) at RT. The reaction was heated to 100° C. and stirred for 2 h. After consumption of the starting material, the reaction mixture was cooled and poured into ice-cold water (100 mL). The resultant solution was extracted with ethyl acetate. The combined organic extracts were dried over anhydrous sodium sulfate and evaporated under reduced pressure. The crude product was washed with diethyl ether to afford 3-(5-chloro-6-methoxybenzo[d]isoxazol-3-yl)propanenitrile (498 mg, 64%) as an off-white solid.

LCMS (ESI): m/z 237/239 [M+H⁺]; Rt=3.29 min; method C.

Intermediate 8a (Intermediate 8 alternative preparation) 3-(5-chloro-6-methoxybenzo[d]isoxazol-3-yl)propanenitrile

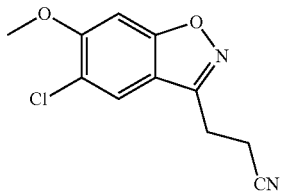 [SMILES: COc1cc2onc(CCC#N)c2cc1Cl]

To a stirred solution of 2-(5-chloro-6-methoxybenzo[d]isoxazol-3-yl)ethyl methanesulfonate (for example as prepared for Intermediate 7a) (220 g, 721.3 mmol) in DMSO (1.5 L) was added NaCN (176.7 g, 3.606 mol) at RT. The reaction was heated at 80° C. and for 4 h. After consumption of the starting material, the reaction mixture was diluted with ice-cold water and the resultant solution extracted with ethyl acetate. The combined organic extracts were dried over anhydrous sodium sulfate and evaporated under reduced pressure. The crude product was washed with n-pentane to afford 3-(5-chloro-6-methoxybenzo[d]isoxazol-3-yl)propanenitrile (154 g, 90%) as an off-white solid.

$^1$H NMR (400 MHz, DMSO-d$_6$): δ 8.11 (s, 1H), 7.54 (s, 1H), 3.97 (s, 3H), 3.30 (t, J=7.2 Hz, 2H), 3.03 (t, J=7.2 Hz, 2H); LCMS (ESI): m/z 237[M+H$^+$]; Rt=3.49 min; method D.

Intermediate 9: 3-(5-chloro-6-methoxybenzo[d]isoxazol-3-yl)propanoic acid

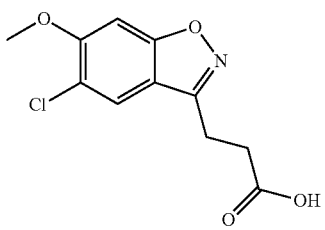 [SMILES: COc1cc2onc(CCC(=O)O)c2cc1Cl]

To a stirred solution of 3-(5-chloro-6-methoxybenzo[d]isoxazol-3-yl)propanenitrile (for example as prepared for Intermediate 8) (600 mg, crude) in ethanol (10 mL) and water (2 mL) was added sodium hydroxide (508 mg, 12.7 mmol). The reaction mixture was stirred at reflux for 16 h. After completion of the reaction, the reaction mixture was concentrated under reduced pressure. The residue obtained was diluted with water and washed with ethyl acetate. The aqueous layer was acidified with diluted hydrochloric acid (up to pH~2) and extracted with ethyl acetate. The combined organic extracts were washed with brine, dried over anhydrous sodium sulfate and concentrated under reduced pressure to afford 3-(5-chloro-6-methoxybenzo[d]isoxazol-3-yl)propanoic acid (500 mg, 77%) as an off-white solid.

$^1$H NMR (400 MHz, DMSO-d$_6$): δ 12.24 (bs, 1H; D$_2$O exchangeable), 8.05 (s, 1H), 7.50 (s, 1H), 3.96 (s, 3H), 3.15 (t, J=7.3 Hz, 2H), 2.76 (t, J=7.3 Hz, 2H); LCMS (ESI): m/z 256/258 [M+H$^+$]; Rt=1.92 min; method A.

Intermediate 9a (Intermediate 9 alternative preparation): 3-(5-chloro-6-methoxybenzo[d]isoxazol-3-yl)propanoic acid

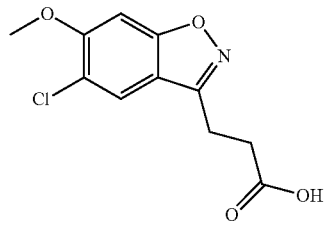 [SMILES: COc1cc2onc(CCC(=O)O)c2cc1Cl]

To a stirred solution of 3-(5-chloro-6-methoxybenzo[d]isoxazol-3-yl)propanenitrile (for example as prepared for Intermediate 8a) (154 g, 652.5 mmol) in ethanol (1.4 L) was added a solution of NaOH (130.5 g, 3.262 mol) in water (840 mL) at 0° C. The reaction mixture was heated at 80° C. for 16 h. After completion of the reaction, the mixture was evaporated under reduced pressure. The residue obtained was diluted with ice-cold water and acidified with diluted hydrochloric acid (up to pH~2). The resultant solution was extracted with ethyl acetate, the combined organic extracts were dried over anhydrous sodium sulfate and concentrated under reduced pressure to afford a solid. This was triturated with petroleum ether to afford 3-(5-chloro-6-methoxybenzo[d]isoxazol-3-yl)propanoic acid (160 g, 96%) as a brown solid.

$^1$H NMR (400 MHz, DMSO-d$_6$): δ12.25 (s, 1H; D$_2$O exchangeable), 8.05 (s, 1H), 7.50 (s, 1H), 3.96 (s, 3H), 3.15 (t, J=7.3 Hz, 2H), 2.76 (t, J=7.3 Hz, 2H); LCMS (ESI): m/z 256/258 [M+H$^+$]; Rt=1.93 min; method A.

Intermediate 10: ethyl 3-(5-chloro-6-methoxybenzo[d]isoxazol-3-yl)propanoate

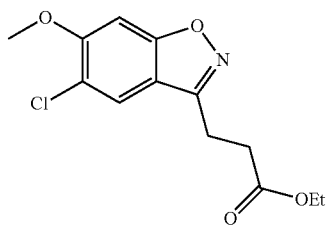 [SMILES: CCOC(=O)CCc1noc2cc(OC)c(Cl)cc12]

To a stirred solution of 3-(5-chloro-6-methoxybenzo[d]isoxazol-3-yl)propanoic acid (for example as prepared for Intermediate 9) (400 mg, 1.56 mmol) in ethanol (20 mL) was added conc. sulphuric acid (2-3 drops) and heated at reflux for 4 h. After completion of the reaction, the reaction mixture was concentrated under reduced pressure. The obtained residue was neutralized with saturated sodium hydrogen carbonate solution and extracted with ethyl acetate. The combined organic extracts were washed with brine, dried over anhydrous sodium sulfate and concentrated under reduced pressure to afford ethyl 3-(5-chloro-6-methoxybenzo[d]isoxazol-3-yl)propanoate (435 mg, 98%) as an off-white solid.

$^1$H NMR (400 MHz, CDCl$_3$): δ 7.66 (s, 1H), 7.05 (s, 1H), 4.17 (q, J=7.1 Hz, 2H), 3.99 (s, 3H), 3.23 (t, J=7.9 Hz, 2H), 2.88 (t, J=7.9 Hz, 2H), 1.26 (t, J=7.1 Hz, 3H); LCMS (ESI): m/z 284/286 [M+H⁺]; Rt=2.43 min; method A.

Intermediate 10a (Intermediate 10 alternative preparation): ethyl 3-(5-chloro-6-methoxybenzo[d]isoxazol-3-yl)propanoate

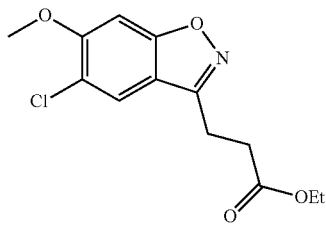 [SMILES: CCOC(=O)CCc1noc2cc(OC)c(Cl)cc12]

To a stirred solution of 3-(5-chloro-6-methoxybenzo[d]isoxazol-3-yl)propanoic acid (for example as prepared for Intermediate 9a) (160 g, 627.4 mmol) in ethanol (1.6 L) was added conc. sulphuric acid (160 mL) drop-wise at 10° C. The reaction mixture was heated at reflux for 4 h. After completion of the reaction, the mixture was concentrated under reduced pressure. The obtained residue was neutralized with saturated sodium hydrogen carbonate solution. The solid precipitate was isolated by filtration and washed with petroleum ether to afford ethyl 3-(5-chloro-6-methoxybenzo[d]isoxazol-3-yl)propanoate (150 g, 84%) as a brown solid.

$^1$H NMR (400 MHz, DMSO-$d_6$): δ8.06 (s, 1H), 7.49 (s, 1H), 4.06 (q, J=7.1 Hz, 2H), 3.96 (s, 3H), 3.19 (t, J=7.3 Hz, 2H), 2.84 (t, J=7.3 Hz, 2H), 1.15 (t, J=7.1 Hz, 3H); LCMS (ESI): m/z 284/286 [M+H⁺]; Rt=2.41 min; method A.

Intermediate 11: ethyl 3-(5-chloro-6-hydroxybenzo[d]isoxazol-3-yl)propanoate

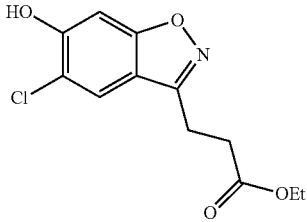 [SMILES: CCOC(=O)CCc1noc2cc(O)c(Cl)cc12]

To a stirred solution of ethyl 3-(5-chloro-6-methoxybenzo[d]isoxazol-3-yl)propanoate (for example as prepared for Intermediate 10) (415 mg, 1.46 mmol) in DCM (20 mL) was added anhydrous aluminium chloride (975 mg, 7.33 mmol) portion-wise at 0° C. The reaction mixture was heated to reflux temperature and maintained for 16 h. After completion of the reaction, the reaction mixture was diluted with water (20 mL). The organic layer was separated, washed with brine, dried over anhydrous sodium sulfate and concentrated under reduced pressure. The crude product was purified by silica gel (100-200 mesh) column chromatography using 20% ethyl acetate in hexane as eluent to afford ethyl 3-(5-chloro-6-hydroxybenzo[d]isoxazol-3-yl)propanoate (338 mg, 86%) as an off-white solid.

$^1$H NMR (400 MHz, DMSO-$d_6$): δ11.12 (s, 1H), 7.97 (s, 1H), 7.12 (s, 1H), 4.06 (q, J=7.1 Hz, 2H), 3.16 (t, J=7.3 Hz, 2H), 2.82 (t, J=7.3 Hz, 2H), 1.15 (t, J=7.1 Hz, 3H); LCMS (ESI): m/z 270/272 [M+H⁺]; Rt=2.14 min; method A.

Intermediate 11a (Intermediate 11 alternative preparation): ethyl 3-(5-chloro-6-hydroxybenzo[d]isoxazol-3-yl)propanoate

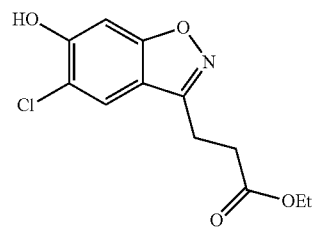

To a stirred solution of ethyl 3-(5-chloro-6-methoxybenzo[d]isoxazol-3-yl)propanoate (for example as prepared for Intermediate 10a) (150 g, 528.7 mmol) in DCM (2.5 L) was added aluminium chloride (351.5 g, 2643 mmol) portion-wise at 0° C. The reaction mixture was heated at reflux for 16 h. After completion of the reaction, the mixture was diluted with water. The organic layer was separated, washed with brine, dried over anhydrous sodium sulfate and concentrated under reduced pressure. The crude solid was washed with petroleum ether to afford ethyl 3-(5-chloro-6-hydroxybenzo[d]isoxazol-3-yl)propanoate (90 g, 63%) as a brown solid.

$^1$H NMR (400 MHz, DMSO-$d_6$): δ 11.11 (s, 1H; $D_2O$ exchangeable), 7.97 (s, 1H), 7.12 (s, 1H), 4.06 (q, J=7.1 Hz, 2H), 3.16 (t, J=7.3 Hz, 2H), 2.82 (t, J=7.3 Hz, 2H), 1.15 (t, J=7.1 Hz, 3H); LCMS (ESI): m/z 270/272 [M⁺]; Rt=2.40 min; method A.

Intermediate 12: (S)-1-(pyridin-2-yl)ethyl methanesulfonate

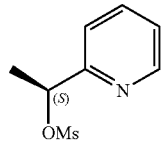

To a stirred solution of (S)-1-(pyridin-2-yl)ethanol (150 mg, 1.21 mmol) in DCM (10 mL) was added triethylamine (0.25 mL, 1.82 mmol) and mesyl chloride (0.11 mL, 1.46 mmol) at 0° C. The reaction was stirred at 0° C. for 30 min. After completion of the reaction, the reaction mixture was diluted with water and the organic layer was separated. The organic phase was dried over anhydrous sodium sulfate and evaporated under reduced pressure to afford (S)-1-(pyridin-2-yl)ethyl methanesulfonate (215 mg) as a thick liquid, which was directly taken for next reaction without purification.

Intermediate 12a (Intermediate 12 alternative preparation): (S)-1-(pyridin-2-yl)ethyl methanesulfonate

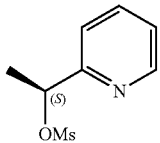

To a stirred solution of (S)-1-(pyridin-2-yl)ethanol (35 g, 284.2 mmol) in DCM (700 mL) were added triethylamine (42.79 g, 423.6 mmol) and mesyl chloride (36.2 g, 317.8 mmol) at 0° C. The reaction was stirred at RT for 2 h. After completion of the reaction, the reaction solution was washed with brine and the organic phase evaporated under reduced pressure to afford (S)-1-(pyridin-2-yl)ethyl methanesulfonate (57 g, 99%) as a pink liquid, which was directly taken for the next reaction without purification.

Intermediate 13: (R)-ethyl 3-(5-chloro-6-(1-(pyridin-2-yl)ethoxy)benzo[d]isoxazol-3-yl)propanoate

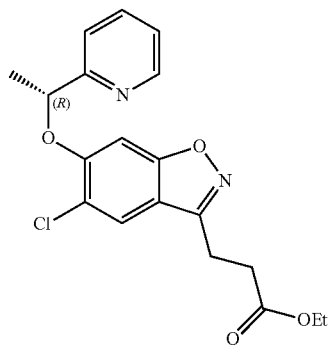

To a stirred solution of ethyl 3-(5-chloro-6-hydroxybenzo[d]isoxazol-3-yl)propanoate (for example as prepared for Intermediate 11) (150 mg, 0.55 mmol) in DMF (6 mL) were added potassium carbonate (115 mg, 0.83 mmol) and a solution of (S)-1-(pyridin-2-yl)ethyl methanesulfonate (for example as prepared for Intermediate 12) (168 mg, 0.83 mmol) in DMF (6 mL) at RT. The reaction mixture was heated at 60° C. for 12 h. After completion of the reaction, the reaction mixture was diluted with water and extracted with ethyl acetate (2×25 mL). The combined organic extracts were washed with brine, dried over anhydrous sodium sulfate and evaporated under reduced pressure to afford the crude. The crude product was purified by silica gel (100-200 mesh) column chromatography using 20% ethyl acetate in hexane as eluent to afford (R)-ethyl 3-(5-chloro-6-(1-(pyridin-2-yl)ethoxy)benzo[d]isoxazol-3-yl)propanoate (180 mg, 86%) as an oil.

$^1$H NMR (400 MHz, DMSO-$d_6$): δ 8.59 (m, 1H), 8.08 (s, 1H), 7.83 (td, J=7.7, 1.8 Hz, 1H), 7.51 (dt, J=7.7, 1.1 Hz, 1H), 7.38 (s, 1H), 7.33 (ddd, J=7.7, 4.8, 1.1 Hz, 1H), 5.77 (q, J=6.3 Hz, 1H), 4.06 (q, J=7.1 Hz, 2H), 3.16 (t, J=7.3 Hz, 2H), 2.83 (t, J=7.3 Hz, 2H), 1.68 (d, J=6.3 Hz, 3H), 1.15 (t, J=7.1 Hz, 3H); LCMS (ESI): m/z 375/377 [M+H$^+$]; Rt=2.50 min; method A.

Intermediate 13a (Intermediate 13 alternative preparation): (R)-ethyl 3-(5-chloro-6-(1-(pyridin-2-yl)ethoxy)benzo[d]isoxazol-3-yl)propanoate

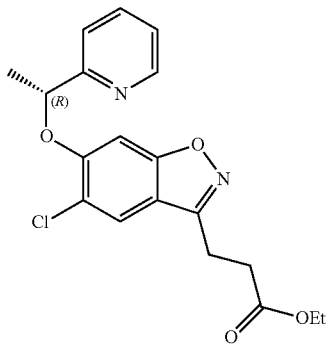

To a stirred solution of ethyl 3-(5-chloro-6-hydroxybenzo[d]isoxazol-3-yl)propanoate (for example as prepared for Intermediate 11a) (48 g, 177.9 mmol) in DMF (800 mL) were added potassium carbonate (61 g, 442 mmol) and (S)-1-(pyridin-2-yl)ethyl methanesulfonate (for example as prepared for Intermediate 12a) (57 g, 283.5 mmol) at 0-10° C. The reaction mixture was heated at 75-80° C. for 16 h. After completion of the reaction, the reaction mixture was diluted with saturated ammonium chloride solution and extracted with ethyl acetate. The combined organic extracts were evaporated under reduced pressure. The crude product was purified by silica gel (100-200 mesh) column chromatography eluting with 13% ethyl acetate in petroleum ether to afford (R)-ethyl 3-(5-chloro-6-(1-(pyridin-2-yl)ethoxy)benzo[d]isoxazol-3-yl)propanoate (54 g, 81%) as a pale yellow semi-solid.

$^1$H NMR (400 MHz, DMSO-$d_6$): δ 8.58 (m, 1H), 8.08 (s, 1H), 7.82 (td, J=7.7, 1.8 Hz, 1H), 7.51 (dt, J=7.9, 1.1 Hz, 1H), 7.37 (s, 1H), 7.32 (ddd, J=7.7, 4.9, 1.1 Hz, 1H), 5.76 (q, J=6.4 Hz, 1H), 4.04 (q, J=7.1 Hz, 2H), 3.16 (t, J=7.3 Hz, 2H), 2.81 (t, J=7.3 Hz, 2H), 1.68 (d, J=6.4 Hz, 3H), 1.14 (t, J=7.1 Hz, 3H); LCMS (ESI): m/z 375/377 [M+H$^+$]; Rt=2.51 min; method A.

Intermediate 14: ethyl 2-(5-chloro-6-methoxybenzo[d]isoxazol-3-yl)acetate

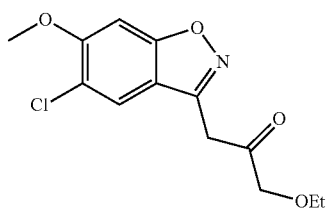 [SMILES: CCOCC(=O)Cc1noc2cc(OC)c(Cl)cc12]

To a stirred solution of 2-(5-chloro-6-methoxybenzo[d]isoxazol-3-yl)acetic acid (for example as prepared for Intermediate 4a) (60 g, 248.3 mmol) in ethanol (750 mL) was added conc. sulphuric acid (60 mL) drop-wise at 10° C. The reaction mixture was heated to reflux and maintained for 2 h. After complete consumption of the starting material, the reaction was concentrated under reduced pressure. The residue was neutralized with saturated aqueous sodium hydrogen carbonate solution and extracted with ethyl acetate. The combined organic extracts were dried over anhydrous sodium sulfate and concentrated under reduced pressure to afford ethyl 2-(5-chloro-6-methoxybenzo[d]isoxazol-3-yl)acetate (60 g, 90%) as a brown solid.

$^1$H NMR (400 MHz, CDCl$_3$): δ 7.69 (s, 1H), 7.05 (s, 1H), 4.21 (q, J=7.1 Hz, 2H), 3.97 (s, 3H), 3.94 (s, 2H), 1.26 (t, J=7.1 Hz, 3H); LCMS (ESI): m/z 270/272 [M+H$^+$]; Rt=2.37 min; method A.

Intermediate 15: 1-Chloro-2,4-dimethoxybenzene

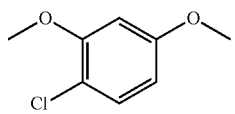

To 4-chlororesorcinol (100 g, 691.8 mmol) in acetone (1000 mL), was added potassium carbonate (286.4 g, 2075.3 mmol) and the reaction mixture stirred at room temperature for 30 min. Dimethyl sulphate (500 mL) was added; the mixture was heated to 60° C. and stirred for 16 h. The mixture was filtered and the filtrate concentrated to afford 1-chloro-2,4-dimethoxybenzene as a yellow oil (124 g, crude).

$^1$H NMR (300 MHz, CDCl$_3$) δ7.23 (s, 1H), 6.51 (d, J=2.7 Hz, 1H), 6.43 (dd, J=8.7, 2.7 Hz, 1H), 3.88 (s, 3H), 3.80 (s, 3H)].

Intermediate 16: 4-(5-Chloro-2,4-dimethoxyphenyl)-4-oxobutanoic acid

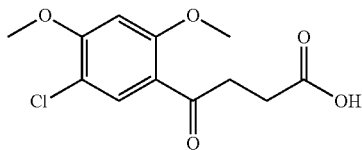 [SMILES: COc1cc(OC)c(C(=O)CCC(=O)O)cc1Cl]

To 1-chloro-2,4-dimethoxybenzene (for example as prepared for Intermediate 15, 124 g, 691.8 mmol) in DCM (1000 mL), was added succinic anhydride (76.2 g, 760.98 mmol) at 0° C. Aluminium chloride (120 g, 899.34 mmol) was added also at 0° C., the reaction mixture was warmed to room temperature and stirred for 30 min. The mixture was poured into ice-water (1000 mL), filtered and dried to afford 4-(5-chloro-2,4-dimethoxyphenyl)-4-oxobutanoic acid as a white solid (127 g).

LCMS (Method I): Rt=1.40 min, [M+H]$^+$ 273.

Intermediate 17: Methyl 4-(5-chloro-2,4-dimethoxyphenyl)-4-oxobutanoate

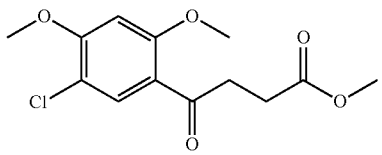

To 4-(5-chloro-2,4-dimethoxyphenyl)-4-oxobutanoic acid (for example as prepared for Intermediate 16, 127 g, 465.7 mmol) in MeOH (500 mL), was added thionyl chloride (66.5 g, 558.8 mmol) at 0° C. The reaction mixture was warmed to room temperature and stirred for 16 h. The solvent was removed, water (500 mL) was to the residue and the mixture extracted with DCM (500 mL×3). The combined organic phases were dried over sodium sulphate and purified by silica gel column chromatography [silica, 200-300 mesh, 1000 g, eluted with petroleum ether/ethyl acetate 4:1 to DCM/MeOH 100:1] to afford methyl 4-(5-chloro-2,4-dimethoxyphenyl)-4-oxobutanoate as a pink solid (120.4 g).

LCMS (Method I): Rt=1.54 min, [M+H]$^+$ 287.

Intermediate 18: Methyl 4-(5-chloro-2-hydroxy-4-methoxyphenyl)-4-oxobutanoate

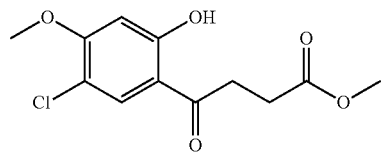

To methyl 4-(5-chloro-2,4-dimethoxyphenyl)-4-oxobutanoate (for example as prepared for Intermediate 17, 120.4 g, 420 mmol) in MeCN (800 mL), was added sodium iodide (93.9 g, 630 mmol) and aluminium chloride (56 g, 420 mmol). After the addition the mixture was poured into ice-water (1000 mL) and extracted with ethyl acetate (600 mL×4). The combined organic phases were concentrated and purified with silica gel column chromatography [silica, 200-300 mesh, 500 g, eluted with petroleum ether/ethyl acetate 5:1 to DCM/MeOH 100:1] to afford methyl 4-(5-chloro-2-hydroxy-4-methoxyphenyl)-4-oxobutanoate as a yellow solid (95.3 g).

LCMS (Method I): Rt=1.57 min, [M+H]$^+$ 273.

Intermediate 19: Methyl 4-(5-chloro-2-hydroxy-4-methoxyphenyl)-4-(hydroxyimino)butanoate

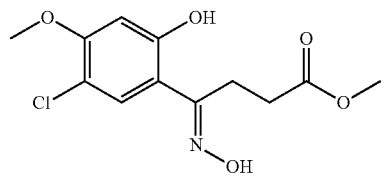

To methyl 4-(5-chloro-2-hydroxy-4-methoxyphenyl)-4-oxobutanoate (for example as prepared for Intermediate 18, 95.3 g, 272.68 mmol) in pyridine/MeOH (1:1, 500 mL), was added hydroxylamine hydrochloride (72.6 g, 1044.6 mmol) and the reaction mixture was stirred at 100° C. for 16 h. The solvent was removed, water (500 mL) was added to the residue and the mixture extracted with DCM (500 mL×3). The solvent was removed from the combined organic phases and the residue purified with silica gel column chromatography [silica, 200-300 mesh, 500 g, eluted with DCM:MeOH 100:1] to afford methyl 4-(5-chloro-2-hydroxy-4-methoxyphenyl)-4-(hydroxyimino)butanoate as a yellow solid (50 g).

LCMS (Method I): Rt=1.48 min, [M+H]$^+$ 288.

Intermediate 20: Methyl 3-(5-chloro-6-methoxy-benzo[d]isoxazol-3-yl)propanoate

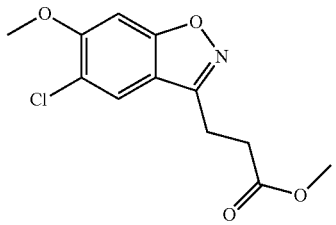

Methyl 4-(5-chloro-2-hydroxy-4-methoxyphenyl)-4-(hydroxyimino)butanoate (for example as prepared for Intermediate 19, 53.4 g, 185.6 mmol) was added to pyridine/acetic anhydride (1:1, 500 mL) and the reaction mixture was stirred at 110° C. for 16 h, and then at 120° C. for 16 h. The solvent was removed and the residue was purified with silica gel column chromatography [silica, 200-300 mesh, 500 g, eluted with petroleum ether/ethyl acetate 5:1 to DCM/MeOH 100:1] to afford 2 batches of methyl 3-(5-chloro-6-methoxybenzo[d]isoxazol-3-yl)propanoate (purple solid, 20 g) and (white solid, 9 g).

LCMS (Method I): Rt=1.53 min, [M+H]+ 270 for both batches.

Intermediate 21: Methyl 3-(5-chloro-6-hydroxy-benzo[d]isoxazol-3-yl)propanoate

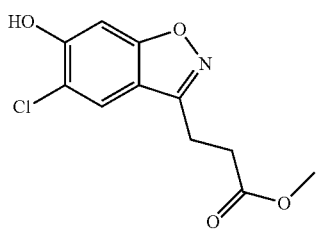 [SMILES: COC(=O)CCc1noc2cc(O)c(Cl)cc12]

To methyl 3-(5-chloro-6-methoxybenzo[d]isoxazol-3-yl)propanoate (for example as prepared for Intermediate 20, 29 g, 107.53 mmol) in DCM (500 mL), was added aluminium chloride (72 g, 537.7 mmol) at room temperature and the reaction mixture was stirred at room temperature for 16 h. The mixture was poured into ice/water (500 mL), extracted with DCM (400 mL×3) and dried over sodium sulphate. The solvent was removed and the residue purified with silica gel column chromatography [silica, 200-300 mesh, 200 g, eluted with DCM/petroleum ether 1:1 to DCM/ethyl acetate 100:3] to afford 3-(5-chloro-6-hydroxybenzo[d]isoxazol-3-yl)propanoate as a yellow solid (22 g).

LCMS (Method I): Rt=1.39 min, [M+H]+ 256.

Intermediate 22: (R)-Methyl 3-(5-chloro-6-(1-(pyridin-2-yl)ethoxy)benzo[d]isoxazol-3-yl)propanoate

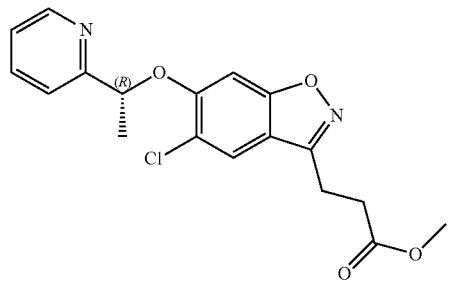

To methyl 3-(5-chloro-6-hydroxybenzo[d]isoxazol-3-yl)propanoate (for example as prepared for Intermediate 21, 21.5 g, 84.1 mmol) in THF (300 mL), was added (S)-1-(pyridin-2-yl)ethanol (10.3 g, 84.1 mmol), triphenylphosphine (26.5 g, 100.92 mmol), diethyl azodicarboxylate (17.6 g, 100.92 mmol), and the reaction mixture was stirred at room temperature for 16 h. The solvent was removed and the residue purified by silica gel column chromatography [silica: 200-300 mesh, 300 g, eluted with petroleum ether/ethyl acetate 7:1] to afford (R)-methyl 3-(5-chloro-6-(1-(pyridin-2-yl)ethoxy)benzo[d]isoxazol-3-yl)propanoate as a pale yellow oil (28 g).

LCMS (Method I): Rt=1.61 min, [M+H]+361.

Intermediate 23: 6-Methyl-2-tosyl-2,3-dihydro-pyridazine-3-carbonitrile

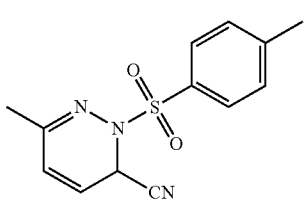

A solution of 3-methylpyridazine (47 g, 500 mmol) in DCM (500 mL), was added trimethylsilyl cyanide (90 g, 900 mmol) and aluminium chloride (0.4 g) and the mixture stirred at room temperature for 30 min. p-Toluenesulfonyl chloride (163.8 g, 900 mmol) in DCM was added drop-wise at room temperature and the reaction mixture stirred at room temperature for 16 h. The solvent was evaporated and the residual solid washed with ethanol (300 mL) to afford 6-methyl-2-tosyl-2,3-dihydropyridazine-3-carbonitrile as a white solid (115 g).

$^1$H NMR (300 MHz, CDCl$_3$) δ 7.95 (d, J=8.4 Hz, 2H), 7.37 (d, J=8.0 Hz, 2H), 6.23 (dd, J=9.2, 6.7 Hz, 1H), 6.14-6.06 (m, 1H), 5.70 (d, J=6.7 Hz, 1H), 2.46 (s, 3H), 2.15 (s, 3H).

Intermediate 23a (Intermediate 23 alternative preparation): 6-methyl-2-tosyl-2,3-dihydropyridazine-3-carbonitrile

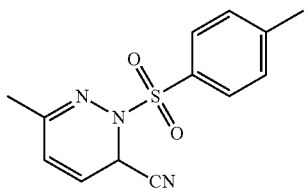

To a solution of 3-methylpyridazine (289 g, 3.07 mol) in DCM (4 L), was added trimethylsilyl cyanide (368 g, 3.68 mol) and aluminium chloride (2.5 g, 18.8 mmol) and the reaction mixture was stirred at room temperature for 30 min. p-Toluenesulfonyl chloride (670 g, 3.68 mol) was added in portions at room temperature and the reaction stirred at room temperature for 3 h. The solvent was evaporated and the solid was washed with ethanol (2 L) to give 6-methyl-2-tosyl-2,3-dihydropyridazine-3-carbonitrile as a white solid (688 g).

$^1$H NMR (300 MHz, CDCl$_3$) δ 7.95 (d, J=8.3 Hz, 2H), 7.37 (d, J=8.1 Hz, 2H), 6.23 (dd, J=9.2, 6.7 Hz, 1H), 6.10 (d, J=9.2 Hz, 1H), 5.70 (d, J=6.7 Hz, 1H), 2.46 (s, 3H), 2.14 (s, 3H); LCMS(A): Rt=1.47 min, MH$^+$276.

Intermediate 24: 6-Methylpyridazine-3-carbonitrile

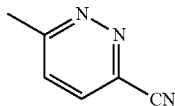

A solution of 6-methyl-2-tosyl-2,3-dihydropyridazine-3-carbonitrile (for example as prepared for Intermediate 23 115 g, 0.41 mol) in THF (1 L), was added 1,8-diazabicyclo[5.4.0]undec-7-ene (75 g, 0.49 mol) drop-wise at room temperature. The reaction mixture was stirred at room temperature for 2 h, the solvent evaporated and DCM (2 L) was added. The mixture was washed with water (1 L), dried and concentrated. The residue was purified with column chromatography [silica, 200-300 mesh, 500 g, eluted with petroleum ether/ethyl acetate 1:2] to afford 6-methyl-pyridazine-3-carbonitrile as a yellow solid (37.6 g).

LCMS (Method I): Rt=0.93 min, [M+H]$^+$ 120.

Intermediate 24a (Intermediate 24 alternative preparation): 6-methylpyridazine-3-carbonitrile

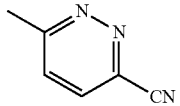

To a solution of 6-methyl-2-tosyl-2,3-dihydropyridazine-3-carbonitrile (688 g, 2.5 mol) in THF (3 L, anhydrous) was added dropwise 1,8-diazabicyclo[5.4.0]undec-7-ene (400 g, 2.63 mol) at room temperature and the reaction mixture was stirred at room temperature for 2 h. The solvent was evaporated and DCM (3 L) was added to the residue. The mixture was washed with water (2 L), dried with magnesium sulfate and the solvent evaporated. The residue was purified with column chromatography (silica, 2 Kg, eluted with petroleum ether/ethyl acetate 1:1) to give 6-methylpyridazine-3-carbonitrile as a yellow solid (228 g).

$^1$H NMR (300 MHz, CDCl$_3$) δ 7.74 (d, J=8.6 Hz, 1H), 7.52 (d, J=8.6 Hz, 1H), 2.86 (s, 3H); LCMS(Method I): Rt=1.01 min, MH$^+$120.

Intermediate 25: 1-(6-Methylpyridazin-3-yl)ethanone

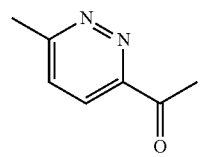

To a solution of 6-methylpyridazine-3-carbonitrile (for example as prepared for Intermediate 24, 28 g, 250 mmol) in toluene (300 mL) and diethyl ether (300 mL), was added methyl magnesium bromide (3M in ether, 208 ml, 625 mmol) drop-wise at −10° C. The reaction mixture was stirred at 0° C. for 2 h. Hydrochloric acid (2N, 400 mL) was added and stirred at 0° C. for 15 min., then the aqueous phase was basified with sodium bicarbonate. The mixture was extracted with DCM (500 mL×3), dried and evaporated. The residue was purified by flash chromatography [silica, 200-300 mesh, 500 g, eluted with petroleum ether/ethyl acetate 2:1] to afford 1-(6-methylpyridazin-3-yl)ethanone as a brown solid (20 g).

LCMS (Method I): Rt=1.08 min, [M+H]$^+$ 137.

Intermediate 25a (Intermediate 25 alternative preparation): 1-(6-methylpyridazin-3-yl)ethanone

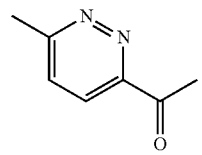

To a solution of 6-methylpyridazine-3-carbonitrile (228 g, 1.92 mol) in toluene (2 L, anhydrous) and diethyl ether (2 L, anhydrous) was added methyl magnesium bromide (3M in ether, 0.77 L, 2.3 mol) dropwise at −10° C. under nitrogen. The reaction mixture was stirred at 0° C. for 1 h and quenched by addition of hydrochloric acid (2N, 2 L). The aqueous phase was separated and adjusted to pH 7-8 with sodium bicarbonate (solid). The aqueous phase was extracted with DCM (2 L×3), dried with magnesium sulfate and evaporated. The residue was purified by column chromatography (silica: 100-200 mesh, 2 Kg, eluted with petroleum ether/ethyl acetate 1:1) to afford 1-(6-methylpyridazin-3-yl)ethanone as a brown solid (151 g, 58%).

$^1$H NMR (300 MHz, CDCl$_3$) δ 8.02 (d, J=8.6 Hz, 1H), 7.48 (d, J=8.6 Hz, 1H), 2.87 (s, 3H), 2.81 (s, 3H); LCMS (Method I): Rt=1.11 min, MH$^+$137.

A portion of this material (70 g, 515 mmol) was dissolved in hydrochloric acid (2 N, 500 mL), the reaction mixture was stirred at room temperature for 2 h, then adjusted to pH 8 with sodium bicarbonate (solid). The mixture was extracted with DCM (500 mL×3), dried with magnesium sulfate and the solvent evaporated to give 1-(6-methylpyridazin-3-yl)ethanone as a brown solid (68 g).

¹H NMR (300 MHz, CDCl₃) δ 58.00 (d, J=8.6 Hz, 1H), 7.47 (d, J=8.6 Hz, 1H), 2.87 (s, 3H), 2.80 (s, 3H); LCMS (Method I): Rt=1.11 min, MH⁺137.

Intermediate 26:
(S)-1-(6-Methylpyridazin-3-yl)ethanol

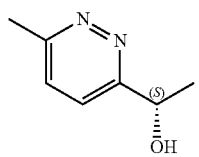

To a solution of (R)-3,3-diphenyl-1-methylpyrrolidino[1,2-c]-1,3,2-oxazaborole (R-CBS, 1 M in toluene, 10 mL, 10 mmol) in THF (50 mL) was added borane-methyl sulfide complex (2M, 5 mL, 10 mmol) and the reaction mixture was stirred at room temperature for 1 h. 1-(6-methylpyridazin-3-yl)ethanone (for example as prepared for Intermediate 25, 1.36 g, 10 mmol) was added and the reaction mixture was stirred at room temperature for 4 h under nitrogen. MeOH was added, the solvent was evaporated and the residue was purified by flash chromatography [silica: 200-300 mesh, 40 g, eluted with petroleum ether/ethyl acetate 1:1 to DCM/MeOH 10:1] to afford (S)-1-(6-methylpyridazin-3-yl)ethanol (330 mg).

LCMS (Method I): Rt=0.55 min, [M+H]⁺ 139.

Intermediate 26a (Intermediate 26 alternative preparation): (S)-1-(6-methylpyridazin-3-yl)ethanol

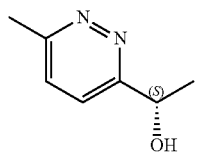

To a solution of 1-(6-methylpyridazin-3-yl)ethanone (58.7 g, 431 mmol) and RuCl₂[(R)-xylbinap][(R)-daipen] (CAS no 220114-32-9, 1.05 g, 0.862 mmol) in isopropanol (800 mL) was added potassium tert-butoxide (10.5 g, 86.2 mol) and the reaction mixture was stirred at room temperature under hydrogen atmosphere (50 psi) for 72 h. The volatiles were evaporated and the residue purified by column chromatography [silica: 100-200 mesh, 1 Kg, eluted with DCM/MeOH 20:1] to give (S)-1-(6-methylpyridazin-3-yl)ethanol as a brown solid (17 g).

¹H NMR (300 MHz, CDCl₃) δ 7.46 (d, J=8.6 Hz, 1H), 7.35 (d, J=8.6 Hz, 1H), 5.11 (q, J=6.5 Hz, 1H), 4.11 (s, 1H), 2.72 (s, 3H), 1.57 (d, J=6.6 Hz, 3H); LCMS (Method I): Rt=0.50 min, MH⁺139.

Intermediate 27: 1-(6-Methylpyridazin-3-yl)ethanol

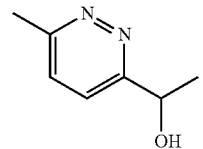

To a solution of 1-(6-methylpyridazin-3-yl)ethanone (for example as prepared for Intermediate 25, 10 g, 73.5 mmol) in MeOH (50 mL), was added sodium borohydride (5.58 g, 147 mmol) at room temperature and the reaction mixture stirred at room temperature for 2 h. The solvent was evaporated and DCM was added. The mixture was filtered and the residue washed with DCM. The combined organic phases were evaporated and the residue purified with flash chromatography [silica, 200-300 mesh, 80 g, eluted with DCM/MeOH 20:1] to afford 1-(6-methylpyridazin-3-yl)ethanol as an oil (8.2 g).

LCMS (Method I): Rt=0.55 min, [M+H]⁺ 139.

Intermediate 28: 1-(6-Methylpyridazin-3-yl)ethyl methanesulfonate

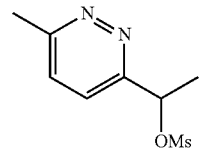

To a solution of 1-(6-methylpyridazin-3-yl)ethanol (for example as prepared for Intermediate 27, 8.2 g, 59.4 mmol) in DCM (100 mL), was added triethylamine (7.2 g, 71.3 mmol) and methanesulfonyl chloride (8.55 g, 59.4 mmol) and the reaction mixture stirred at room temperature for 2 h. The reaction was quenched with water (50 mL), extracted with DCM (50 mL×3) and the combined organic phased dried and the solvent evaporated. The residue was purified by flash chromatography [silica; 200-300 mesh, 80 g, eluted with DCM/MeOH 20:1] to afford 1-(6-methylpyridazin-3-yl)ethyl methanesulfonate as a brown oil (9.8 g).

LCMS (Method I): Rt=1.16 min, [M+H]⁺ 217.

Intermediate 29: Methyl 3-(5-chloro-6-(1-(6-methylpyridazin-3-yl)ethoxy)benzo[d]isoxazol-3-yl)propanoate

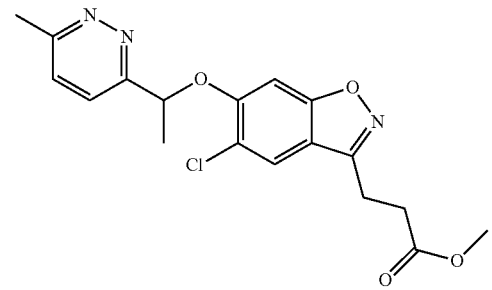

To methyl 3-(5-chloro-6-hydroxybenzo[d]isoxazol-3-yl)propanoate (for example as prepared for Intermediate 21, 7.67 g, 30 mmol) and 1-(6-methylpyridazin-3-yl)ethyl methanesulfonate (for example as prepared for Intermediate 28, 30 mmol) in MeOH (500 mL) was added potassium carbonate (8.28 g, 60 mmol) and the reaction mixture was stirred at 70° C. for 16 h. The solvent was evaporated and the residue purified by silica gel column chromatography [silica, 200-300 mesh, 150 g, eluted with DCM/ethyl acetate 10:1] to obtain methyl 3-(5-chloro-6-(1-(6-methylpyridazin-3-yl)ethoxy)benzo[d]isoxazol-3-yl)propanoate as a white solid (8.5 g).

LCMS (Method I): Rt=1.48 min, [M+H]$^+$ 376.

Intermediate 30: (R)-methyl 3-(5-chloro-6-(1-(6-methylpyridazin-3-yl)ethoxy)benzo[d]isoxazol-3-yl)propanoate

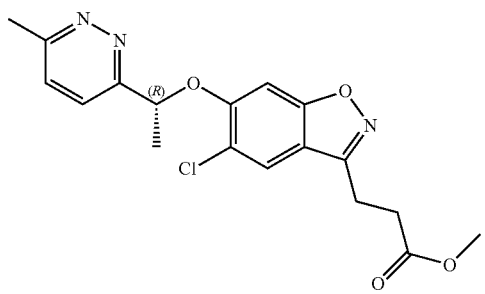

To a solution of (S)-1-(6-methylpyridazin-3-yl)ethanol (20.7 g, 150 mmol) and methyl 3-(5-chloro-6-hydroxybenzo[d]isoxazol-3-yl)propanoate (38.2 g, 150 mmol) in THF (200 mL, anhydrous) and toluene (200 mL, anhydrous) was added diethyl azodicarboxylate (31.3 g, 180 mmol) and triphenylphosphine (47.2 g, 180 mmol). The reaction mixture was stirred at room temperature for 3 hours, the volatiles evaporated and the residue purified by column chromatography (silica: 100-200 mesh, 1.5 Kg, eluted with DCM/ethyl acetate 5:1) to give (R)-methyl 3-(5-chloro-6-(1-(6-methylpyridazin-3-yl)ethoxy)benzo[d]isoxazol-3-yl)propanoate as an off-white solid (49.5 g).

$^1$H NMR (300 MHz, CDCl$_3$) δ 7.65 (s, 1H), 7.58 (d, J=8.7 Hz, 1H), 7.35 (d, J=8.6 Hz, 1H), 7.06 (s, 1H), 5.86 (d, J=6.4 Hz, 1H), 3.71 (s, 3H), 3.20 (t, J=7.3 Hz, 2H), 2.88 (t, J=7.4 Hz, 2H), 2.74 (s, 3H), 1.84 (d, J=6.5 Hz, 3H); LCMS (Method I): Rt=1.43 min, MH$^+$ 376.

EXAMPLES

Example 1: (R)-3-(5-chloro-6-(1-(pyridin-2-yl)ethoxy)benzo[d]isoxazol-3-yl)propanoic acid

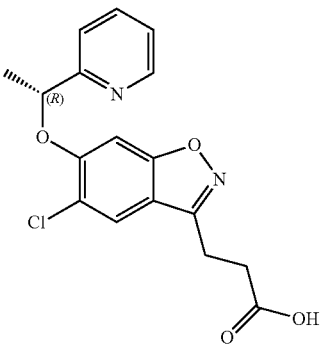

To a stirred solution of (R)-ethyl 3-(5-chloro-6-(1-(pyridin-2-yl)ethoxy)benzo[d]isoxazol-3-yl)propanoate (for example as prepared for Intermediate 13) (180 mg, 0.48 mmol) in THF:ethanol:water (5:2:2; 9 mL) was added lithium hydroxide hydrate (40 mg, 0.96 mmol) and maintained at RT for 2 h. After completion of the reaction, the reaction was concentrated under reduced pressure and acidified to pH~4 with citric acid. The resultant solution was extracted with ethyl acetate. The combined organic extracts were washed with brine, dried over anhydrous sodium sulphate and evaporated under reduced pressure to afford solid, which was triturated with petroleum ether (2×10 mL) to afford (R)-3-(5-chloro-6-(1-(pyridin-2-yl)ethoxy)benzo[d]isoxazol-3-yl)propanoic acid (75 mg, 45%) as semi-solid.

$^1$H NMR (400 MHz, DMSO-d$_6$): δ 12.24 (s, 1H; D$_2$O exchangeable), 8.58 (dd, J=4.9, 1.7 Hz, 1H), 8.07 (s, 1H), 7.82 (td, J=7.8, 1.7 Hz, 1H), 7.51 (d, J=7.8 Hz, 1H), 7.39 (s, 1H), 7.33 (dd, J=7.8, 4.9 Hz, 1H), 5.76 (q, J=6.4 Hz, 1H), 3.12 (t, J=7.3 Hz, 2H), 2.73 (t, J=7.3 Hz, 2H), 1.68 (d, J=6.4 Hz, 3H); LCMS (ESI): m/z 347/349[M+H$^+$]; Rt=1.05 min; method B.

Example 1a (Example 1 alternative preparation): (R)-3-(5-chloro-6-(1-(pyridin-2-yl)ethoxy)benzo[d]isoxazol-3-yl)propanoic acid

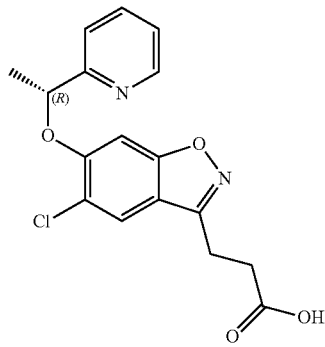

To a stirred solution of (R)-ethyl 3-(5-chloro-6-(1-(pyridin-2-yl)ethoxy)benzo[d]isoxazol-3-yl)propanoate (for example as prepared for Intermediate 13a) (53 g, 141.6 mmol) in THF:water (1:1; 1 L) was added lithium hydroxide monohydrate (23.77 g, 566.6 mmol) at 0-10° C. and allowed to stir at RT for 2 h. After completion of the reaction, the mixture was concentrated under reduced pressure and diluted with water. The resultant solution was washed with diethyl ether and acidified up to pH~2. The resultant solution was extracted with DCM. The combined organic extracts were dried over anhydrous sodium sulphate and evaporated under reduced pressure. The crude material was triturated with n-pentane to afford (R)-3-(5-chloro-6-(1-(pyridin-2-yl)ethoxy)benzo[d]isoxazol-3-yl)propanoic acid (48 g, 96%) as an off-white solid.

$^1$H NMR (400 MHz, DMSO-d$_6$): δ 12.25 (s, 1H; D$_2$O exchangeable), 8.58 (dd, J=4.9, 1.8 Hz, 1H), 8.07 (s, 1H), 7.82 (td, J=7.8, 1.8 Hz, 1H), 7.51 (d, J=7.8 Hz, 1H), 7.37 (s, 1H), 7.33 (dd, J=7.8, 4.9 Hz, 1H), 5.77 (q, J=6.4 Hz, 1H), 3.13 (t, J=7.3 Hz, 2H), 2.74 (t, J=7.3 Hz, 2H), 1.68 (d, J=6.4 Hz, 3H); LCMS (ESI): m/z 345/347 [M−H]$^−$; Rt=2.04 min; method A; Chiral HPLC: 96.2% ee; method G.

The obtained solid was purified by chiral preparative SFC to afford 99.99% enantiomerically pure (R)-3-(5-chloro-6-(1-(pyridin-2-yl)ethoxy)benzo[d]isoxazol-3-yl)propanoic acid (35 g) as a white solid.

$^1$H NMR (400 MHz, DMSO-d$_6$): δ 12.25 (s, 1H; D$_2$O exchangeable), 8.58 (dd, J=4.9, 1.8 Hz, 1H), 8.07 (s, 1H), 7.82 (td, J=7.8, 1.8 Hz, 1H), 7.51 (d, J=7.8 Hz, 1H), 7.37 (s, 1H), 7.33 (dd, J=7.8, 4.9 Hz, 1H), 5.77 (q, J=6.4 Hz, 1H), 3.13 (t, J=7.3 Hz, 2H), 2.74 (t, J=7.3 Hz, 2H), 1.68 (d, J=6.4

Hz, 3H); LCMS (ESI): m/z 347.1 [M+H⁺]; 99.6%; Rt=3.33 min; method E; Chiral HPLC: 99.99% ee; method G.

Preparative Chiral SFC Conditions:

Column/dimensions: CHIRALPAK-IA (250 mm×30 mm); eluent: $CO_2$=50.0%; % methanol=50.0%; total flow: 90 g/min; back pressure: 100 bar; UV: 235 nm; stack time: 38.0 min; instrument: Thar SFC 200.

Analytical Chiral SFC Conditions:

Column/dimensions: CHIRALPAK-IA (250 mm×4.6 mm); eluent: $CO_2$=60.0%; % methanol=40.0%; total flow: 4 g/min; back pressure: 100 bar; UV: 292 nm; stack time: 1.82 min.

Example 1 b: (R)-3-(5-chloro-6-(1-(pyridin-2-yl) ethoxy)benzo[d]isoxazol-3-yl) propanoic acid, tris (hydroxymethyl)aminomethane)

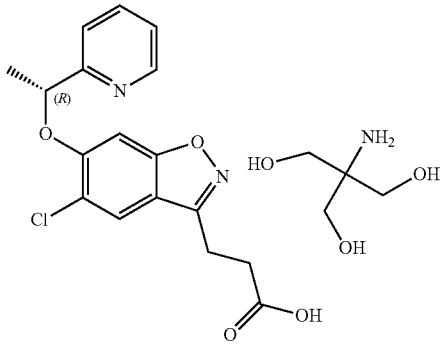

A solution of (R)-3-(5-chloro-6-(1-(pyridin-2-yl)ethoxy) benzo[d]isoxazol-3-yl)propanoic acid (for example as prepared for Example 1) (70 mg, 0.20 mmol) and tris(hydroxymethyl)aminomethane (24 mg, 0.20 mmol) in methanol (10 mL) was heated at 60° C. for 2 h. After 2 h, the reaction mixture was concentrated under reduced pressure to afford a semi-solid, which was then triturated with diethyl ether (10 mL) to afford (R)-3-(5-chloro-6-(1-(pyridin-2-yl)ethoxy)benzo[d]isoxazol-3-yl) propanoic acid, tris (hydroxymethyl)aminomethane) salt (72 mg, 76%) as an off-white solid.

¹H NMR (400 MHz, DMSO-d₆): δ 8.58 (dd, J=4.8, 1.8 Hz, 1H), 8.06 (s, 1H), 7.82 (td, J=7.8, 1.8 Hz, 1H), 7.50 (d, J=7.8 Hz, 1H), 7.36 (s, 1H), 7.32 (dd, J=7.8, 4.8 Hz, 1H), 5.76 (q, J=6.4 Hz, 1H), 4.68 (bs, 6H; D₂O exchangeable), 3.27 (s, 6H), 3.10 (t, J=7.3 Hz, 2H), 2.64 (t, J=7.3 Hz, 2H), 1.68 (d, J=6.4 Hz, 3H); LCMS (ESI): m/z 347/349 [M+H⁺]; Rt=1.99 min; method A.

Examples 1c-1 m were prepared in a manner analogous to the preparation of Example 1b.

Examples 2-28 were prepared in a manner analogous to Examples 1 or 1a.

| Example no. | Name | Structure | Molecular ion + Identity | Retention Time (min) | LCMS Method |
|---|---|---|---|---|---|
| 1c | (R)-3-(5-chloro-6-(1-(pyridin-2-yl)ethoxy)benzo[d]isoxazol-3-yl) propanoic acid compound with sulfuric acid (1:1) | 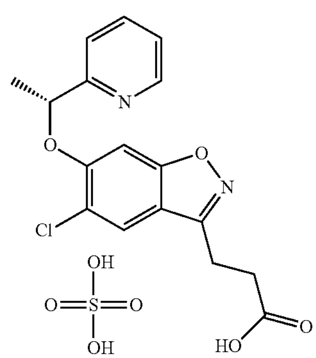 | 347 [M + H⁺] | 2.04 | A |
| 1d | sodium (R)-3-(5-chloro-6-(1-(pyridin-2-yl)ethoxy)benzo[d]isoxazol-3-yl) propanoate | 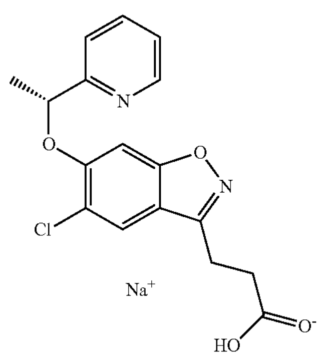 | 347 [M + H⁺] | 2.03 | A |

-continued

| Example no. | Name | Structure | Molecular ion + Identity | Retention Time (min) | LCMS Method |
|---|---|---|---|---|---|
| 1e | (R)-3-(5-chloro-6-(1-(pyridin-2-yl)ethoxy)benzo[d]isoxazol-3-yl)propanoic acid compound with (S)-2-amino-5-guanidinopentanoic acid (1:1) | 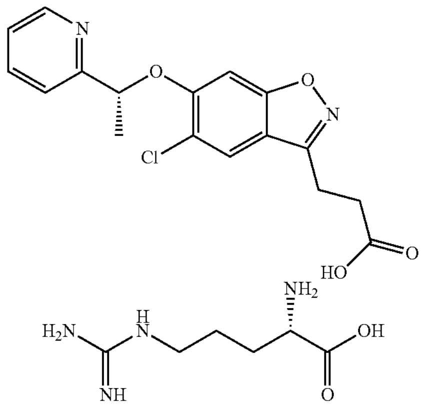 | 347 [M + H$^+$] | 2.02 | A |
| 1f | (R)-3-(5-chloro-6-(1-(pyridin-2-yl)ethoxy)benzo[d]isoxazol-3-yl)propanoic acid compound with (S)-2,6-diaminohexanoic acid (1:1) | 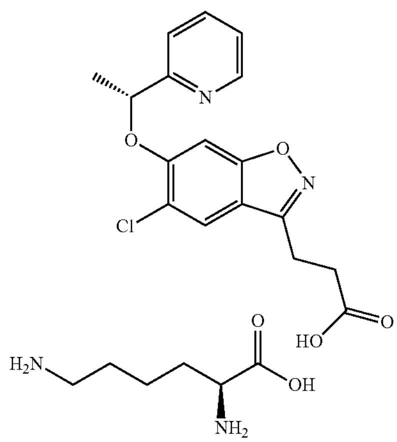 | 347 [M + H$^+$] | 2.03 | A |
| 1g | (R)-3-(5-chloro-6-(1-(pyridin-2-yl)ethoxy)benzo[d]isoxazol-3-yl)propanoic acid hydrochloride | 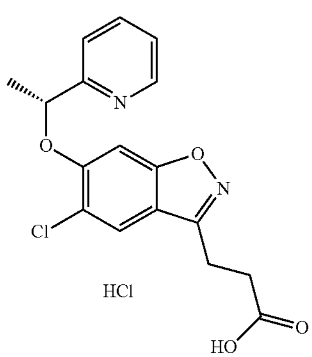 [SMILES: C[C@@H](Oc1cc2onc(CCC(=O)O)c2cc1Cl)c1ccccn1 ; Cl] | 347 [M + H$^+$] | 2.01 | A |

-continued

| Example no. | Name | Structure | Molecular ion + Identity | Retention Time (min) | LCMS Method |
|---|---|---|---|---|---|
| 1h | (2R,3R,4R,5S)-6-(methylamino)hexane-1,2,3,4,5-pentanol (R)-3-(5-chloro-6-(1-(pyridin-2-yl)ethoxy)benzo[d]isoxazol-3-yl)propanoate | 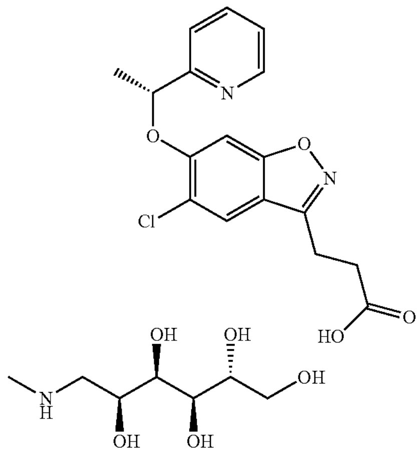 | 347 [M + H$^+$] | 2.02 | A |
| 1i | (R)-3-(5-chloro-6-(1-(pyridin-2-yl)ethoxy)benzo[d]isoxazol-3-yl)propanoic acid compound with methanesulfonic acid (1:1) | 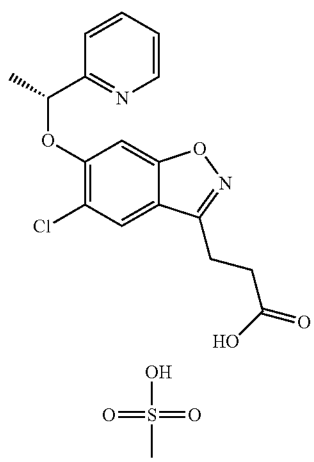 | 347 [M + H$^+$] | 2.06 | A |
| 1j | N-benzyl-2-phenylethanamine (R)-3-(5-chloro-6-(1-(pyridin-2-yl)ethoxy)benzo[d]isoxazol-3-yl)propanoate | 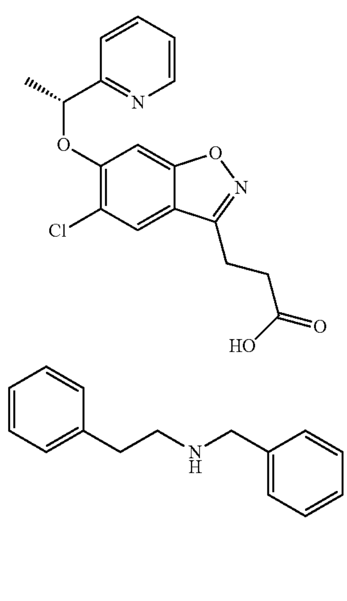 [SMILES: C[C@@H](Oc1cc2onc(CCC(=O)O)c2cc1Cl)c1ccccn1 ; c1ccc(CCNCc2ccccc2)cc1] | 347 [M + H$^+$] | 7.64* | F |

-continued

| Example no. | Name | Structure | Molecular ion + Identity | Retention Time (min) | LCMS Method |
|---|---|---|---|---|---|
| 1k | N$^1$,N$^2$-dibenzylethane-1,2-diamine (R)-3-(5-chloro-6-(1-(pyridin-2-yl)ethoxy)benzo[d]isoxazol-3-yl)propanoate (1:2) | 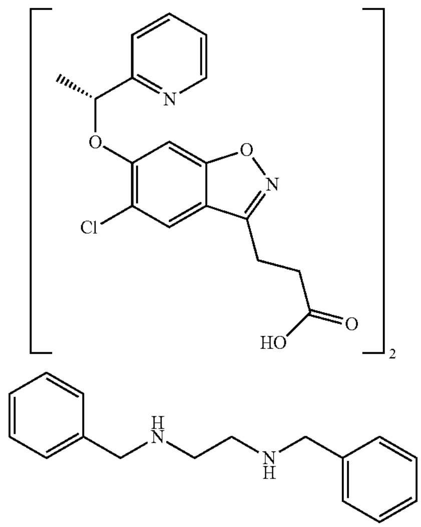 | 347 [M + H$^+$] | 7.65* | F |
| 1l | N$^1$-(2-aminoethyl)ethane-1,2-diamine (R)-3-(5-chloro-6-(1-(pyridin-2-yl)ethoxy)benzo[d]isoxazol-3-yl)propanoate (1:3) | 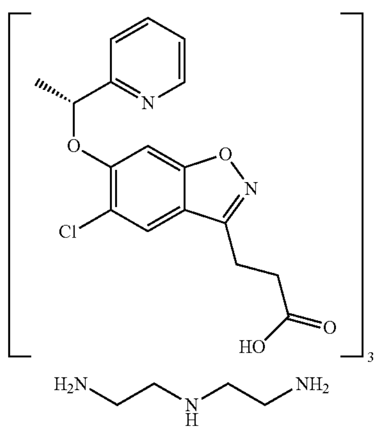 | 347 [M + H$^+$] | 2.03 | A |
| 1m | (R)-3-(5-chloro-6-(1-(pyridin-2-yl)ethoxy)benzo[d]isoxazol-3-yl)propanoic acid compound with 4-methylbenzenesulfonic acid (1:1) | 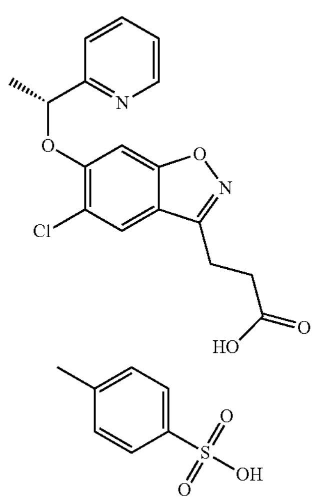 [SMILES: C[C@@H](Oc1cc2onc(CCC(=O)O)c2cc1Cl)c1ccccn1 ; Cc1ccc(S(=O)(=O)O)cc1] | 347 [M + H$^+$] | 7.72* | F |

-continued

| Example no. | Name | Structure | Molecular ion + Identity | Retention Time (min) | LCMS Method |
|---|---|---|---|---|---|
| 2 | 2-amino-2-(hydroxymethyl) propane-1,3-diol 3-(5-chloro-6-(pyridin-2-ylmethoxy) benzo[d] isoxazol-3-yl) propanoate | 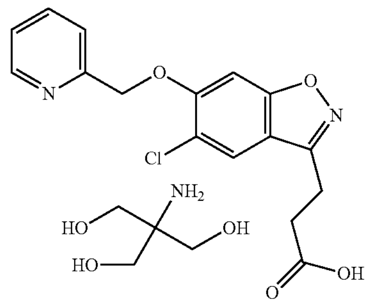 | 333 [M + H$^+$] | 1.90 | A |
| 3 | 2-amino-2-(hydroxymethyl) propane-1,3-diol 3-(5-chloro-6-(1-(5-methylpyridin-2-yl)ethoxy) benzo[d] isoxazol-3-yl) propanoate (single unidentified enantiomer) ISOMER 1 | 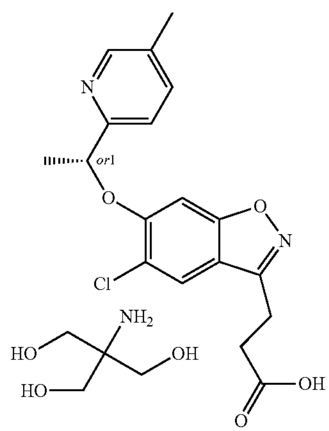 | 361 [M + H$^+$] | 2.10 | A |
| 4 | 2-amino-2-(hydroxymethyl) propane-1,3-diol 3-(5-chloro-6-(1-(5-methylpyridin-2-yl)ethoxy) benzo[d] isoxazol-3-yl) propanoate (single unidentified enantiomer) ISOMER 2 | 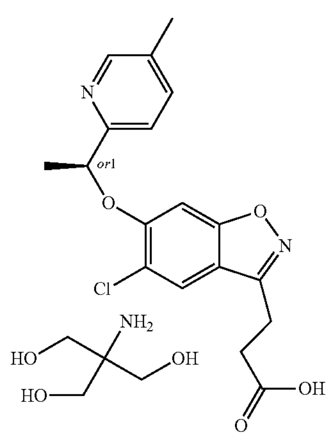 | 361 [M + H$^+$] | 2.10 | A |

-continued

| Example no. | Name | Structure | Molecular ion + Identity | Retention Time (min) | LCMS Method |
|---|---|---|---|---|---|
| 5 | 3-(5-chloro-6-(1-(pyridin-2-yl) ethoxy)benzo[d] isoxazol-3-yl) propanoic acid (racemic) | 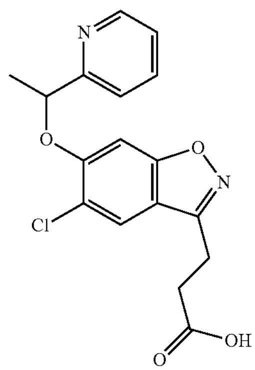 [SMILES: CC(Oc1cc2onc(CCC(=O)O)c2cc1Cl)c1ccccn1] | 347 [M + H⁺] | 2.83 | D |
| 6 | 2-amino-2-(hydroxymethyl) propane-1,3-diol 3-(5-chloro-6-((5-fluoropyridin-2-yl)methoxy) benzo[d] isoxazol-3-yl) propanoate | 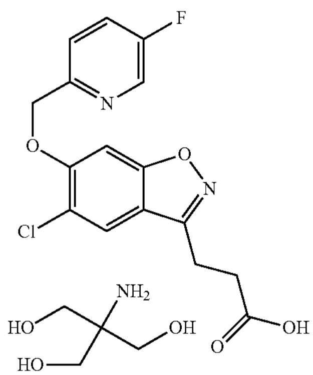 | 351 [M + H⁺] | 2.17 | A |
| 7 | 2-amino-2-(hydroxymethyl) propane-1,3-diol 3-(5-chloro-6-((5-chloropyridin-2-yl)methoxy) benzo[d] isoxazol-3-yl) propanoate | 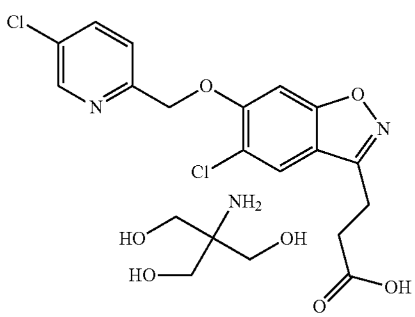 | 367 [M + H⁺] | 2.32 | A |
| 8 | 2-amino-2-(hydroxymethyl) propane-1,3-diol 3-(5-chloro-6-((5-methylpyridin-2-yl)methoxy) benzo[d] isoxazol-3-yl) propanoate | 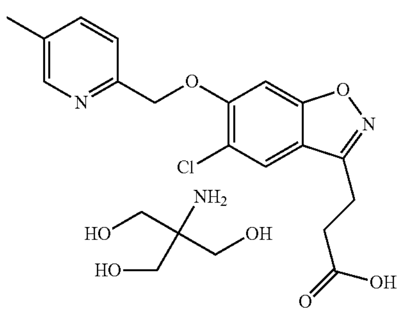 | 347 [M + H⁺] | 1.91 | A |

-continued

| Example no. | Name | Structure | Molecular ion + Identity | Retention Time (min) | LCMS Method |
|---|---|---|---|---|---|
| 9 | 2-amino-2-(hydroxymethyl)propane-1,3-diol 3-(5-chloro-6-(1-(oxazol-2-yl)ethoxy)benzo[d]isoxazol-3-yl)propanoate (single unidentified enantiomer) | 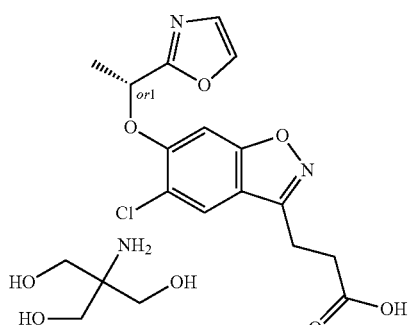<br>ISOMER 1 | 337 [M + H$^+$] | 1.94 | A |
| 10 | 2-amino-2-(hydroxymethyl)propane-1,3-diol 3-(5-chloro-6-(1-(oxazol-2-yl)ethoxy)benzo[d]isoxazol-3-yl)propanoate (single unidentified enantiomer) | 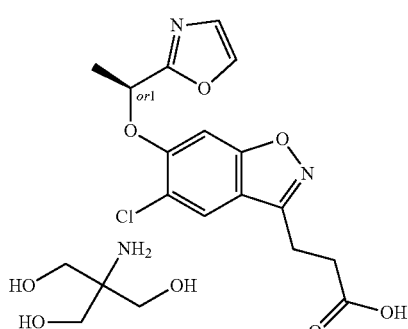<br>ISOMER 2 | 337 [M + H$^+$] | 1.94 | A |
| 11 | 2-amino-2-(hydroxymethyl)propane-1,3-diol 3-(5-chloro-6-(1-(5-fluoropyridin-2-yl)ethoxy)benzo[d]isoxazol-3-yl)propanoate (single unidentified enantiomer) | 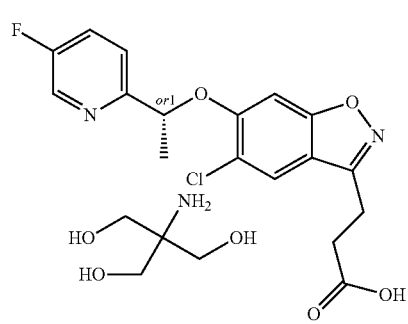 | 365 [M + H$^+$] | 2.09 | A |
| 12 | 2-amino-2-(hydroxymethyl)propane-1,3-diol 3-(5-chloro-6-(1-(5-fluoropyridin-2-yl)ethoxy)benzo[d]isoxazol-3-yl)propanoate (single unidentified enantiomer) | 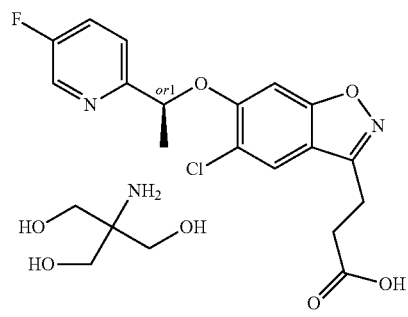 | 365 [M + H$^+$] | 2.09 | A |

| Example no. | Name | Structure | Molecular ion + Identity | Retention Time (min) | LCMS Method |
|---|---|---|---|---|---|
| 13 | 3-(5-chloro-6-(pyridazin-3-ylmethoxy)benzo[d]isoxazol-3-yl)propanoic acid | 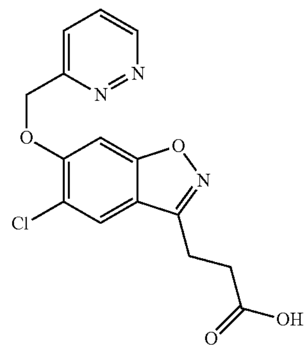 [SMILES: O=C(O)CCc1noc2cc(OCc3cccnn3)c(Cl)cc12] | 334 [M + H⁺] | 1.66 | A |
| 14 | 2-amino-2-(hydroxymethyl)propane-1,3-diol 3-(5-chloro-6-(1-pyrimidin-2-yl)ethoxy)benzo[d]isoxazol-3-yl)propanoate (single unidentified enantiomer) | ISOMER 1 | 348 [M + H⁺] | 1.86 | A |
| 15 | 2-amino-2-(hydroxymethyl)propane-1,3-diol 3-(5-chloro-6-(1-(pyrimidin-2-yl)ethoxy)benzo[d]isoxazol-3-yl)propanoate (single unidentified enantiomer) | ISOMER 2 | 348 [M + H⁺] | 1.86 | A |
| 16 | 2-amino-2-(hydroxymethyl)propane-1,3-diol 3-(5-chloro-6-(1-(5-chloropyridin-2-yl)ethoxy)benzo[d]isoxazol-3-yl)propanoate (single unidentified enantiomer) | ISOMER 1 | 381 [M + H]⁺ | 2.41 | A |

-continued

| Example no. | Name | Structure | Molecular ion + Identity | Retention Time (min) | LCMS Method |
|---|---|---|---|---|---|
| 17 | 3-(5-chloro-6-((6-methylpyridazin-3-yl)methoxy)benzo[d]isoxazol-3-yl) propanoic acid | 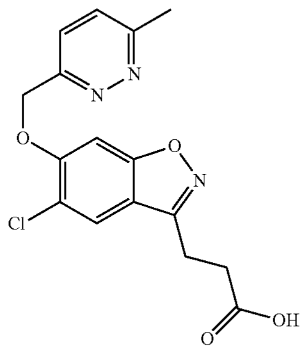 [SMILES: Cc1ccc(COc2cc3onc(CCC(=O)O)c3cc2Cl)nn1] | 348 [M + H]+ | 1.74 | A |
| 18 | 2-amino-2-(hydroxymethyl) propane-1,3-diol 3-(5-chloro-6-(1-(5-chloropyridin-2-yl)ethoxy) benzo[d]isoxazol-3-yl) propanoate (single unidentified enantiomer) | ISOMER 2 | 381 [M + H]+ | 2.41 | A |
| 19 | (S)-3-(5-chloro-6-(1-(6-methylpyridazin-3-yl)ethoxy) benzo[d]isoxazol-3-yl) propanoic acid | 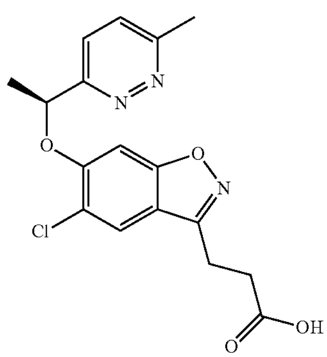 [SMILES: Cc1ccc([C@H](C)Oc2cc3onc(CCC(=O)O)c3cc2Cl)nn1] | 362 [M + H]+ | 1.84 | A |
| 20 | (R)-3-(5-chloro-6-(1-(6-methylpyridazin-3-yl)ethoxy) benzo[d]isoxazol-3-yl) propanoic acid | 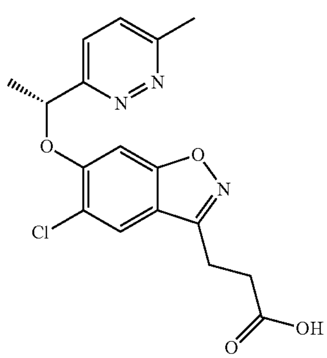 [SMILES: Cc1ccc([C@@H](C)Oc2cc3onc(CCC(=O)O)c3cc2Cl)nn1] | 362 [M + H]+ | 1.85 | A |

| Example no. | Name | Structure | Molecular ion + Identity | Retention Time (min) | LCMS Method |
|---|---|---|---|---|---|
| 21 | 3-(5-chloro-6-(1-(pyridazin-3-yl)ethoxy)benzo[d]isoxazol-3-yl)propanoic acid (single unidentified enantiomer) | 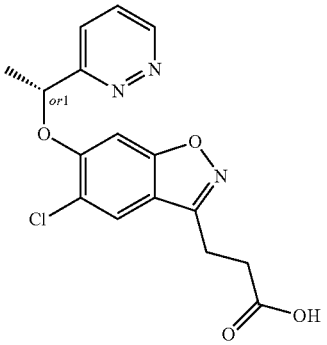<br>ISOMER 1 | 348 [M + H]⁺ | 1.80 | A |
| 22 | 3-(5-chloro-6-(1-(pyridazin-3-yl)ethoxy)benzo[d]isoxazol-3-yl)propanoic acid (single unidentified enantiomer) | 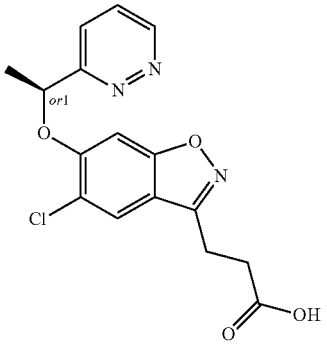<br>ISOMER 2 | 348 [M + H]⁺ | 1.80 | A |
| 23 | 3-(5-chloro-6-(1-(5-methylpyridin-2-yl)propoxy)benzo[d]isoxazol-3-yl)propanoic acid (single unidentified enantiomer) | 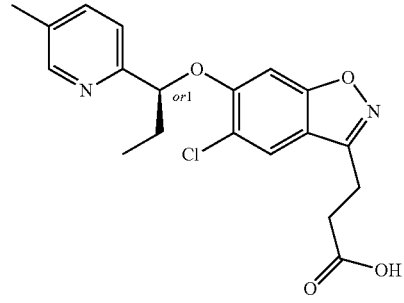<br>ISOMER 1 | 375 [M + H]⁺ | 2.30 | A |
| 24 | 3-(5-chloro-6-(1-(5-methylpyridin-2-yl)propoxy)benzo[d]isoxazol-3-yl)propanoic acid (single unidentified enantiomer) | 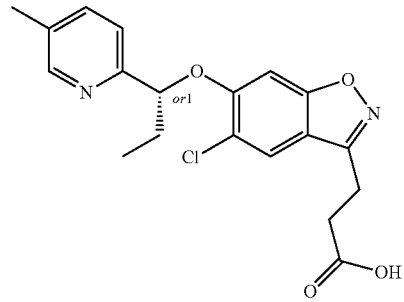<br>ISOMER 2 | 375 [M + H]⁺ | 2.29 | A |

| Example no. | Name | Structure | Molecular ion + Identity | Retention Time (min) | LCMS Method |
|---|---|---|---|---|---|
| 25 | 3-(5-chloro-6-(1-(pyridin-2-yl)propoxy) benzo[d] isoxazol-3-yl) propanoic acid (single unidentified enantiomer) | 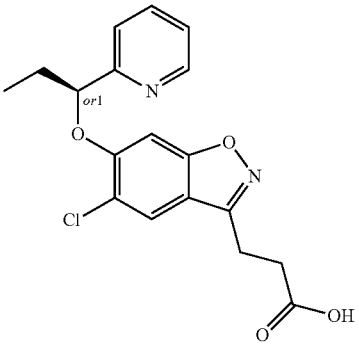 ISOMER 1 | 361 [M + H]⁺ | 2.19 | A |
| 26 | 3-(5-chloro-6-(1-(pyridin-2-yl)propoxy) benzo[d] isoxazol-3-yl) propanoic acid (single unidentified enantiomer) | 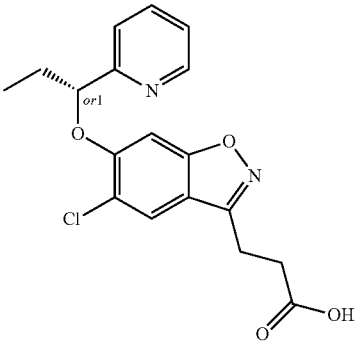 ISOMER 2 | 361 [M + H]⁺ | 2.19 | A |
| 27 | 3-(5-chloro-6-(1-(5-chloropyridin-2-yl)propoxy) benzo[d] isoxazol-3-yl) propanoic acid (single unidentified enantiomer) | 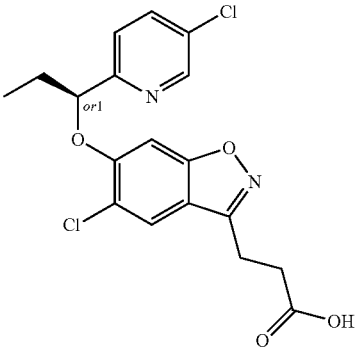 ISOMER 1 | 395 [M + H]⁺ | 2.56 | A |
| 28 | 3-(5-chloro-6-(1-(5-chloropyridin-2-yl)propoxy) benzo[d] isoxazol-3-yl) propanoic acid (single unidentified enantiomer) | 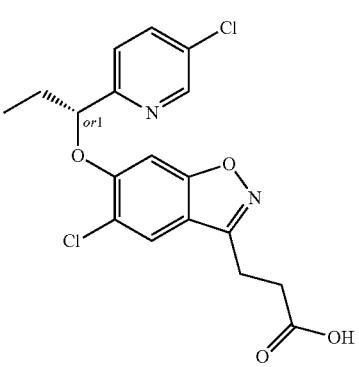 ISOMER 2 | 395 [M + H]⁺ | 2.53 | A₅ |

Also prepared were (R)-3-(5-chloro-6-(1-(pyridin-2-yl)ethoxy)benzo[d]isoxazol-3-yl)propanoic acid 2-aminoethanol salt, (R)-3-(5-chloro-6-(1-(pyridin-2-yl)ethoxy)benzo[d]isoxazol-3-yl)propanoic acid 1,2-ethanedisulphonic acid salt and bis ((R)-3-(5-chloro-6-(1-(pyridin-2-yl)ethoxy)benzo[d]isoxazol-3-yl)propanoic acid) sulphate.

Example 1 n (Example 1 alternative preparation): (R)-3-(5-Chloro-6-(1-(pyridin-2-yl)ethoxy)benzo[d]isoxazol-3-yl)propanoic acid

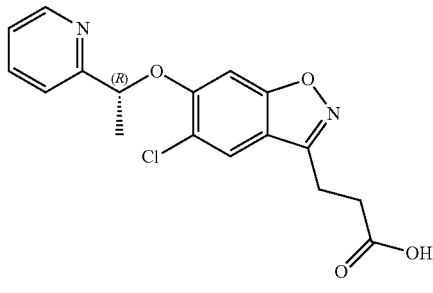

To (R)-methyl 3-(5-chloro-6-(1-(pyridin-2-yl)ethoxy)benzo[d]isoxazol-3-yl)propanoate (for example as prepared for Intermediate 22, 28 g, 77.6 mmol) in THF (500 mL), was added lithium hydroxide (1 N, 310 mL, 310 mmol) and the mixture was stirred at room temperature for 1 h. The organic solvent was removed, hydrochloric acid (1 N) was added until the mixture reached pH 6 and the mixture then extracted with ethyl acetate (300 mL×3). The combined organic phases were dried over sodium sulphate and concentrated. The residue was dissolved in THF (50 mL), hexane (300 mL) was added and the resulting solid isolated by filteration and dried to afford (R)-3-(5-chloro-6-(1-(pyridin-2-yl)ethoxy)benzo[d]isoxazol-3-yl)propanoic acid as a white solid (22.7 g).

LCMS (Method I): Rt=1.46 min, [M+H]⁺ 347.

¹H NMR (300 MHz, CD₃OD) δ 8.55 (ddd, J=4.9, 1.7, 0.9 Hz, 1H), 7.87 (s, 1H), 7.83 (td, J=7.8, 1.8 Hz, 1H), 7.56 (d, J=8.0 Hz, 1H), 7.34 (ddd, J=7.6, 4.9, 1.2 Hz, 1H), 7.07 (s, 1H), 5.62 (q, J=6.4 Hz, 1H), 3.19 (t, J=7.3 Hz, 2H), 2.82 (t, J=7.2 Hz, 2H), 1.76 (d, J=6.5 Hz, 3H); HPLC: 214 nm 100%, 254 nm 100%, chiral-HPLC: 214 nm 97.5%, 254 nm 98.4%.

Example 20a (Example 20 alternative preparation): (R)-3-(5-Chloro-6-(1-(6-methylpyridazin-3-yl)ethoxy)benzo[d]isoxazol-3-yl)propanoic acid

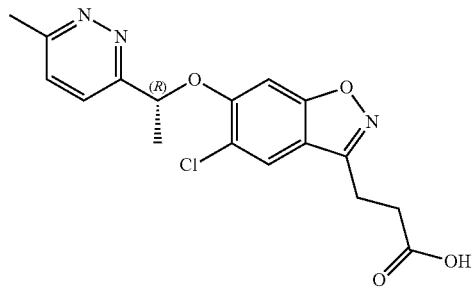

To a solution of methyl 3-(5-chloro-6-(1-(6-methylpyridazin-3-yl)ethoxy)benzo[d]isoxazol-3-yl)propanoate (for example as prepared for Intermediate 29, 8.5 g, 22.7 mmol) in THF (100 mL), was added lithium hydroxide (3N, 30 mL, 90.8 mmol) and the solution stirred at room temperature for 2 h. The solvent was evaporated, water (50 mL) was added and the pH adjusted to between pH 2-3 with hydrochloric acid (1 N). The solid was isolated by filtration and dried in air to give a white solid. This solid was purified by chiral-prep-HPLC [SFC, column:chiralpak-IC, CO₂-MeOH (formic acid)] to obtain (R)-3-(5-chloro-6-(1-(6-methylpyridazin-3-yl)ethoxy)benzo[d]isoxazol-3-yl)propanoic acid as an off-white solid (3.57 g).

LCMS (Method I): Rt=1.37 min, [M+H]⁺362. ¹H NMR (300 MHz, d₆-DMSO) δ 12.29 (s, 1H), 8.08 (s, 1H), 7.68 (d, J=8.7 Hz, 1H), 7.60 (d, J=8.8 Hz, 1H), 7.48 (s, 1H), 6.03 (dd, J=12.7, 6.3 Hz, 1H), 3.12 (t, J=7.2 Hz, 2H), 2.73 (t, J=7.2 Hz, 2H), 2.60 (s, 3H), 1.73 (d, J=6.4 Hz, 3H). HPLC: 214 nm 98.9%, 254 nm 99.5%.

Example 20b (Example 20 alternative preparation): (R)-3-(5-chloro-6-(1-(6-methylpyridazin-3-yl)ethoxy)benzo[d]isoxazol-3-yl)propanoic acid

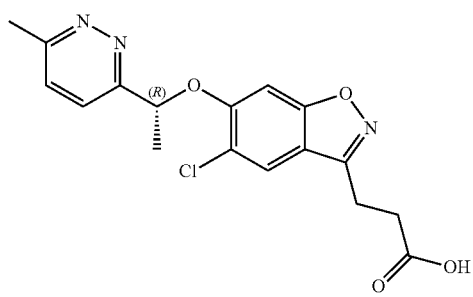

To (R)-3-(5-chloro-6-(1-(6-methylpyridazin-3-yl)ethoxy)benzo[d]isoxazol-3-yl)propanoic acid (79.5 g, 220 mmol, ee 89.5%) in MeCN (2 L), L(+)-arginine (38.3 g, 220 mmol) was added and the reaction mixture was stirred at 55° C. for 0.5 h. The mixture was cooled to room temperature, the solid was filtered and washed with MeCN (200 mL) and dried in air to give a white solid. The solid was added to hydrochloric acid (37%, 1.5 L), and stirred at room temperature for 1 h, filtered and the solid washed with water (500 mL×3) and dried in air to give (R)-3-(5-chloro-6-(1-(6-methylpyridazin-3-yl)ethoxy)benzo[d]isoxazol-3-yl)propanoic as a white solid, (68 g, ee 100%).

¹H NMR (400 MHz, d₆-DMSO) δ 12.29 (s, 1H), 8.09 (s, 1H), 7.70 (d, J=8.7 Hz, 1H), 7.61 (d, J=8.7 Hz, 1H), 7.49 (s, 1H), 6.04 (q, J=6.4 Hz, 1H), 3.13 (t, J=7.3 Hz, 2H), 2.74 (t, J=7.3 Hz, 2H), 2.61 (s, 3H), 1.74 (d, J=6.4 Hz, 3H); LCMS (Method I): Rt=1.36 min, MH⁺ 362.

Example 20c (Example 20 alternative preparation): (R)-3-(5-chloro-6-(1-(6-methylpyridazin-3-yl)ethoxy)benzo[d]isoxazol-3-yl)propanoic acid

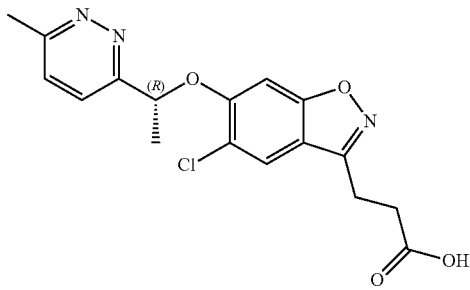

To a solution of (R)-methyl 3-(5-chloro-6-(1-(6-methylpyridazin-3-yl)ethoxy)benzo[d]isoxazol-3-yl)propanoate (87 g, 231.5 mmol) in THF (500 mL) was added lithium hydroxide (2N in water, 462 mL), the reaction mixture was stirred at room temperature for 4 hours, the organic solvent was evaporated and the residual aqueous phase washed with ethyl acetate (500 mL×3). The aqueous phase was acidified with hydrochloric acid (2N) to pH=2-3, the solid was isolated by filtration and washed with water (300 mL×3). The solid was air dried to give (R)-3-(5-chloro-6-(1-(6-methylpyridazin-3-yl)ethoxy)benzo[d]isoxazol-3-yl)propanoic as a light-yellow solid (76 g, 92%, ee 89.5%).

$^1$H NMR (300 MHz, d$_6$-DMSO) δ 12.28 (s, 1H), 8.08 (s, 1H), 7.70 (d, J=8.7 Hz, 1H), 7.61 (d, J=8.7 Hz, 1H), 7.48 (s, 1H), 6.03 (q, J=6.3 Hz, 1H), 3.13 (t, J=7.2 Hz, 2H), 2.74 (t, J=7.2 Hz, 2H), 2.61 (s, 3H), 1.74 (d, J=6.4 Hz, 3H); LCMS(Method I): Rt=1.40 min, MH$^+$362.

| Example no. | Name | Strucure | Molecular ion + Identity | Retention Time (min) | Method |
|---|---|---|---|---|---|
| 29 | 3-{5-Chloro-6-[1-(5-ethylpyridin-2-yl)ethoxy]-1,2-benzoxazol-3-yl}propanoic acid (single unidentified enantiomer) | 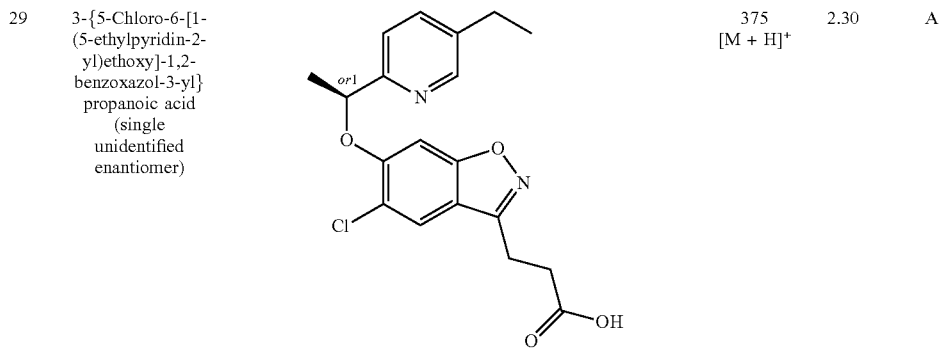 ISOMER 1 | 375 [M + H]$^+$ | 2.30 | A |
| 30 | 3-{5-Chloro-6-[1-(5-ethylpyridin-2-yl)ethoxy]-1,2-benzoxazol-3-yl}propanoic acid (single unidentified enantiomer) | 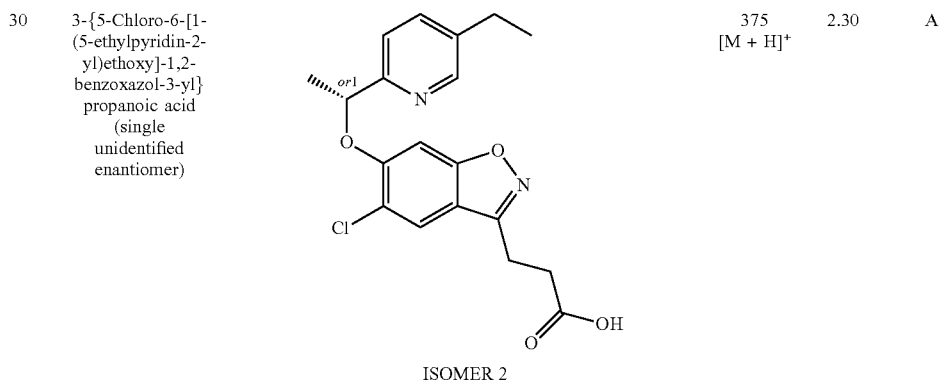 ISOMER 2 | 375 [M + H]$^+$ | 2.30 | A |

| Example no. | Name | Strucure | Molecular ion + Identity | Retention Time (min) | Method |
|---|---|---|---|---|---|
| 31 | 3-{5-Chloro-6-[1-(6-ethylpyridin-2-yl)ethoxy]-1,2-benzoxazol-3-yl} propanoic acid (single unidentified enantiomer) | ISOMER 1 | 375 [M + H]⁺ | 2.26 | A |
| 32 | 3-{5-Chloro-6-[1-(6-ethylpyridin-2-yl)ethoxy]-1,2-benzoxazol-3-yl} propanoic acid (single unidentified enantiomer) | ISOMER 2 | 375 [M + H]⁺ | 2.27 | A |
| 33 | 3-{5-Chloro-6-[(5-chloropyrimidin-2-yl)methoxy]-1,2-benzoxazol-3-yl} propanoic acid | | 368 [M + H]⁺ | 1.44 | I |
| 34 | 3-{5-Chloro-6-[(5-methylpyrimidin-2-yl)methoxy]-1,2-benzoxazol-3-yl}propanoic acid | | 348 [M + H]⁺ | 1.358 | I |

-continued

| Example no. | Name | Strucure | Molecular ion + Identity | Retention Time (min) | Method |
|---|---|---|---|---|---|
| 35 | 3-{5-Chloro-6-[1-(2-methyl-1,3-oxazol-5-yl)ethoxy]-1,2-benzoxazol-3-yl} propanoic acid (single unidentified enantiomer) | ISOMER 1 | 351 [M + H]⁺ | 1.94 | A |
| 36 | 3-{5-Chloro-6-[1-(2-methyl-1,3-oxazol-5-yl)ethoxy]-1,2-benzoxazol-3-yl} propanoic acid (single unidentified enantiomer) | ISOMER 2 | 351 [M + H]⁺ | 1.96 | A |
| 37 | 3-{5-Chloro-6-[1-(5-chloropyrimidin-2-yl)ethoxy]-1,2-benzoxazol-3-yl} propanoic acid (single unidentified enantiomer) | ISOMER 1 | 383 [M + H]⁺ | 1.519 | I |
| 38 | 3-{5-Chloro-6-[1-(5-chloropyrimidin-2-yl)ethoxy]-1,2-benzoxazol-3-yl} propanoic acid (single unidentified enantiomer) | ISOMER 2 | 383 [M + H]⁺ | 1.511 | I |

| Example no. | Name | Strucure | Molecular ion + Identity | Retention Time (min) | Method |
|---|---|---|---|---|---|
| 39 | 3-{5-Chloro-6-[1-(5-methylpyrimidin-2-yl)ethoxy]-1,2-benzoxazol-3-yl} propanoic acid (single unidentified enantiomer) | ISOMER 1 | 362 [M + H]⁺ | 1.44 | I |
| 40 | 3-{5-Chloro-6-[1-(5-methylpyrimidin-2-yl)ethoxy]-1,2-benzoxazol-3-yl} propanoic acid (single unidentified enantiomer) | ISOMER 2 | 362 [M + H]⁺ | 1.44 | I |
| 41 | 3-{5-Chloro-6-[1-(4-ethyl-1,3-oxazol-2-yl)ethoxy]-1,2-benzoxazol-3-yl} propanoic acid (single unidentified enantiomer) | ISOMER 1 | 365 [M + H]⁺ | 2.21 | A |
| 42 | 3-{5-Chloro-6-[1-(4-ethyl-1,3-oxazol-2-yl)ethoxy]-1,2-benzoxazol-3-yl} propanoic acid (single unidentified enantiomer) | ISOMER 2 | 365 [M + H]⁺ | 2.20 | A |

| Example no. | Name | Structure | Molecular ion + Identity | Retention Time (min) | Method |
|---|---|---|---|---|---|
| 43 | 3-{5-Chloro-6-[(1S)-1-(pyrimidin-2-yl)propoxy]-1,2-benzoxazol-3-yl} propanoic acid (single unidentified enantiomer) | ISOMER 1 | 362 [M + H]⁺ | 2.03 | A |
| 44 | 3-{5-Chloro-6-[1-(pyrimidin-2-yl)propoxy]-1,2-benzoxazol-3-yl} propanoic acid (single unidentified enantiomer) | ISOMER 2 | 362 [M + H]⁺ | 2.03 | A |
| 45 | 3-{5-Chloro-6-[1-(pyridazin-3-yl)propoxy]-1,2-benzoxazol-3-yl} propanoic acid (single unidentified enantiomer) | ISOMER 1 | 362 [M + H]⁺ | 1.90 | A |
| 46 | 3-{5-Chloro-6-[1-(pyridazin-3-yl)propoxy]-1,2-benzoxazol-3-yl} propanoic acid (single unidentified enantiomer) | ISOMER 2 | 362 [M + H]⁺ | 1.90 | A |

| Example no. | Name | Structure | Molecular ion + Identity | Retention Time (min) | Method |
|---|---|---|---|---|---|
| 47 | 3-{5-Chloro-6-[1-(6-methylpyridazin-3-yl)propoxy]-1,2-benzoxazol-3-yl}propanoic acid (single unidentified enantiomer) | 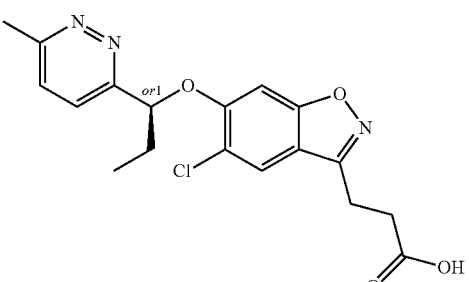 ISOMER 1 | 376 [M + H]⁺ | 1.94 | A |
| 48 | 3-{5-Chloro-6-[1-(6-methylpyridazin-3-yl)propoxy]-1,2-benzoxazol-3-yl}propanoic acid (single unidentified enantiomer) | 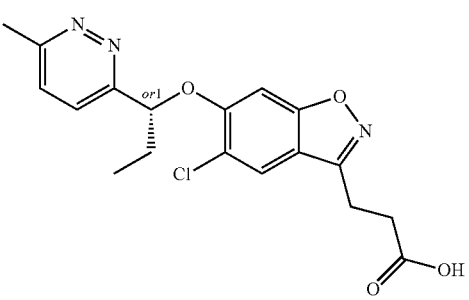 ISOMER 2 | 376 [M + H]⁺ | 1.94 | A |
| 49 | 3-{5-Chloro-6-[1-(5-methylpyrimidin-2-yl)propoxy]-1,2-benzoxazol-3-yl}propanoic acid (single unidentified enantiomer) | 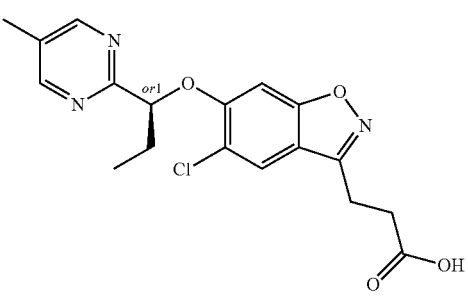 ISOMER 1 | 376 [M + H]⁺ | 2.11 | A |
| 50 | 3-{5-Chloro-6-[1-(5-methylpyrimidin-2-yl)propoxy]-1,2-benzoxazol-3-yl}propanoic acid (single unidentified enantiomer) | 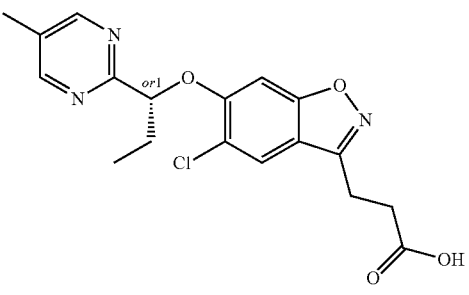 ISOMER 2 | 376 [M + H]⁺ | 2.11 | A |

| Example no. | Name | Strucure | Molecular ion + Identity | Retention Time (min) | Method |
|---|---|---|---|---|---|
| 51 | 3-{5-Chloro-6-[1-(5-chloropyrimidin-2-yl)propoxy]-1,2-benzoxazol-3-yl} propanoic acid (single unidentified enantiomer) ISOMER 1 | | 396 [M + H]+ | 2.34 | A |
| 52 | 3-{5-Chloro-6-[1-(5-chloropyrimidin-2-yl)propoxy]-1,2-benzoxazol-3-yl} propanoic acid (single unidentified enantiomer) ISOMER 2 | | 396 [M + H]+ | 2.34 | A |
| 53 | 3-(5-chloro-6-(1-(1-ethyl-1H-pyrazol-3-yl)ethoxy)benzo[d]isoxazol-3-yl) propanoic acid (single unidentified enantiomer) ISOMER 1 | | 364/366 [M + H]+ | 2.02 | A |
| 54 | 3-(5-chloro-6-(1-(1-ethyl-1H-pyrazol-3-yl)ethoxy)benzo[d]isoxazol-3-yl) propanoic acid (single unidentified enantiomer) ISOMER 2 | | 364/366 [M + H]+ | 2.02 | A |

-continued

| Example no. | Name | Structure | Molecular ion + Identity | Retention Time (min) | Method |
|---|---|---|---|---|---|
| 55 | 3-{5-chloro-6-[(1R)-1-(3-fluoropyridin-2-yl)ethoxy]-1,2-benzoxazol-3-yl} propanoic acid | | 365/367 [M + H]⁺ | 1.50 | I |

Methods of Use

Certain compounds of the invention are inhibitors of KMO. Compounds which inhibit KMO may be useful in the treatment of various conditions or disorders mediated by KMO, for example acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

Additional conditions or disorders include hyperproliferative diseases of benign or malignant behaviour, in which cells of various tissues and organs exhibit aberrant patterns of growth, proliferation, migration, signalling, senescence, and death. Generally hyperproliferative disease refers to diseases and disorders associated with the uncontrolled proliferation of cells, including but not limited to uncontrolled growth of organ and tissue cells resulting in cancers and benign tumours. Hyperproliferative disorders associated with endothelial cells can result in diseases of angiogenesis such as angiomas, endometriosis, obesity, age-related macular degeneration and various retinopathies, as well as the proliferation of ECs and smooth muscle cells that cause restenosis as a consequence of stenting in the treatment of atherosclerosis. Hyperproliferative disorders involving fibroblasts (i.e. fibrogenesis) include but are not limited to disorders of excessive scaring (i.e. fibrosis) such as age-related macular degeneration, cardiac remodelling and failure associated with myocardial infarction, excessive wound healing such as commonly occurs as a consequence of surgery or injury, keloids, and fibroid tumours and stenting.

Further such conditions or disorders include transplant rejection (suppression of T-cells) and graft vs host disease, systemic inflammatory disorders, brain inflammatory disorders including malaria and African trypanosomiasis, and pneumococcal meningitis.

Further such conditions or disorders include cirrhosis, chronic pancreatitis, liver fibrosis, lung fibrosis and ischemia-reperfusion injury.

Further such conditions or disorders include, for example, neurodegenerative diseases, psychiatric or neurological diseases or disorders, Creutzfeld-Jacob disease, trauma-induced neurodegeneration, high-pressure neurological syndrome, dystonia, olivopontocerebellar atrophy, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, dementia such as senile dementia, AIDS-induced encephalopathy, other infection related encephalopathy, viral or bacterial meningitis, infectious diseases caused by viral, bacterial and other parasites, (for example, general central nervous system (CNS) infections such as viral, bacterial or parasitic infection, for example, poliomyelitis, Lyme disease (Borrelia burgdorferi infection)) septic shock, and cancers, cancers with cerebral localization, hepatic encephalopathy, systemic lupus, analgesia and opiate withdrawal symptoms, feeding behaviour, psychiatric disorders, such as insomnia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, endogenous depression, involutional depression, reactive depression, psychotic depression, depression caused by underlying medical conditions, cyclothymic disorders, dysthymic disorders, mood disorders due to general medical condition, mood disorders not otherwise specified and substance-induced mood disorders.

Further such conditions or disorders also include, for example, acute necrotizing pancreatitis, AIDS (disease), aseptic meningitis, brain disease, for example, Gilles de la Tourette syndrome, Asperger syndrome, Rett syndrome, pervasive developmental disorders, aging-related brain disease, and developmental brain disease, burnout syndrome, carbon monoxide poisoning, cardiac arrest or insufficiency and hemorrhagic shock (global brain ischemia), cataract formation and aging of the eye, central nervous system disease, cerebrovascular disease, chronic fatigue syndrome, chronic stress, cognitive disorders, convulsive disorders, such as variants of grand mal and petit mal epilepsy and Partial Complex Epilepsy, diabetes mellitus, disease of the nervous system (e.g., dyskinesia, L-DOPA induced movement disorders, drug addiction, pain and cataract), drug dependence, drug withdrawal, feeding disorders, Guillain Barr Syndrome and other neuropathies, immune disease, immunitary disorders and therapeutic treatment aimed at modifying biological responses (for instance administrations of interferons or interleukins), inflammatory disorders of the central and/or peripheral nervous system, Injury (trauma, polytrauma), Mental and behavioral disorders, metabolic disease, pain disease, or disorder selected from a group of inflammatory pain, neurophathic pain or migraine, allodynia, hyperalgesia pain, phantom pain, neuropathic pain related to diabetic neuropathy, multiple organ failure, near drowning, necrosis, neoplasms of the brain, neoplastic disorders including lymphomas and other malignant blood disorders, nervous system disease (high-pressure neurological Syndrome, infection), nicotine addiction and other addictive disorders including alcoholism, cannabis, benzodiazepine, barbiturate, morphine and cocaine dependence, change in appetite, sleep disorders, changes in sleep pattern, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, as a neuroprotective agent, spinal cord disease, systemic lupus erythematosis, traumatic damage to the brain and spinal cord, and tremor syndromes and poor balance, brakykinesia, rigidity, tremor, change in speech, loss of facial expression, micrographia, difficulty swallowing, drooling, confusion, fear, sexual dysfunction, language impairment, impairment in decision making, violent outbursts, aggression, hallucination, apathy, impairment in abstract thinking.

Further such conditions or disorders also include, for example, cardiovascular diseases, which refer to diseases and disorders of the heart and circulatory system. These diseases are often associated with dyslipoproteinemias and/or dyslipidemias. Cardiovascular diseases include, but are not limited to, cardiomegaly, atherosclerosis, myocardial infarction, and congestive heart failure, coronary heart disease, hypertension and hypotension.

In particular, such conditions or disorders include conditions or disorders where elevated levels of tryptophan metabolites have been correlated with severity of disease and poor prognosis, including shock, trauma in patients with multiple organ failure, severe acute pancreatitis and chronic kidney disease (Logters, T. T., et al. (2009) Shock 32: 29-34, Dabrowski et al (2014) Inflammation 37: 223-234, Changsirivathanathamrong et al (2011) Critical Care Medicine 39: 2678-2683, Mole, D. J., et al. (2008) Br J Surg 95: 855-867, Zhao (2013) Renal Failure 35: 648-653, Pawlak, K. et al (2009) Blood Coagulation and Fibrinolysis 20: 590-594, Kabayashi, T. et al (2014) Biochemical and Biophysical Research Communications 445: 412-416).

The methods of treatment of the invention comprise administering a therapeutically effective amount of a compound of formula (I), or a pharmaceutically acceptable salt thereof, to a patient in need thereof. Individual embodiments of the invention include methods of treating any one of the above-mentioned disorders by administering a therapeutically effective amount of a compound of formula (I), or a pharmaceutically acceptable salt thereof, to a patient in need thereof.

As used herein, 'treat' or 'treatment' in reference to a disorder means: (1) to ameliorate or prevent the disorder or one or more of the biological manifestations of the disorder, (2) to interfere with (a): one or more points in the biological cascade that leads to or is responsible for the disorder, or (b): one or more of the biological manifestations of the disorder, (3) to alleviate one or more of the symptoms or effects associated with the disorder, or (4) to slow the progression of the disorder or one or more of the biological manifestations of the disorder.

As indicated above, 'treatment' of a disorder may include prevention or prophylaxis of the disorder. It will be appreciated that 'prevention' is not an absolute term. In medicine, 'prevention' is understood to refer to the prophylactic administration of a drug to substantially diminish the likelihood or severity of a disorder or biological manifestation thereof, or to delay the onset of such disorder or biological manifestation thereof.

As used herein, 'effective amount' in reference to a compound of formula (I), or a pharmaceutically acceptable salt thereof, or other pharmaceutically-active agent means an amount of the compound sufficient to treat the patient's condition within the scope of sound medical judgment. An effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein "patient" refers to a human (including adults and children) or other mammal. In one embodiment, "patient" refers to a human.

The invention further provides, in a further aspect, a method of treatment of a condition or disorder mediated by KMO (such as the aforementioned disorders), which method comprises administering to a patient in need thereof a therapeutically effective amount of a compound of formula (I) or a pharmaceutically acceptable salt thereof.

In one embodiment there is provided a method of treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which method comprises administering to a patient in need thereof a therapeutically effective amount of a compound of formula (I) or a pharmaceutically acceptable salt thereof.

In one embodiment there is provided a method of treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which method comprises administering to a patient in need thereof a therapeutically effective amount of a compound of formula (I) or a pharmaceutically acceptable salt thereof.

In one embodiment there is provided a method of treatment of acute pancreatitis, which method comprises administering to a patient in need thereof a therapeutically effective amount of a compound of formula (I) or a pharmaceutically acceptable salt thereof.

In one embodiment there is provided a method of treatment of acute pancreatitis, which method comprises administering to a patient in need thereof a therapeutically effective amount of (R)-3-(5-chloro-6-(1-(pyridin-2-yl)ethoxy)benzo[d]isoxazol-3-yl)propanoic acid or a pharmaceutically acceptable salt thereof.

In one embodiment there is provided a method of treatment of acute pancreatitis, which method comprises administering to a patient in need thereof a therapeutically effective amount of (R)-3-(5-chloro-6-(1-(6-methylpyridazin-3-yl)ethoxy)benzo[d]isoxazol-3-yl)propanoic acid or a pharmaceutically acceptable salt thereof.

In one embodiment there is provided a method of treatment of chronic kidney disease, which method comprises administering to a patient in need thereof a therapeutically effective amount of a compound of formula (I) or a pharmaceutically acceptable salt thereof.

In one embodiment there is provided a method of treatment of chronic kidney disease, which method comprises administering to a patient in need thereof a therapeutically effective amount of (R)-3-(5-chloro-6-(1-(pyridin-2-yl)ethoxy)benzo[d]isoxazol-3-yl)propanoic acid or a pharmaceutically acceptable salt thereof.

In one embodiment there is provided a method of treatment of chronic kidney disease, which method comprises administering to a patient in need thereof a therapeutically effective amount of (R)-3-(5-chloro-6-(1-(6-methylpyridazin-3-yl)ethoxy)benzo[d]isoxazol-3-yl)propanoic acid or a pharmaceutically acceptable salt thereof.

In a further aspect, there is provided a compound of formula (I) or a pharmaceutically acceptable salt thereof for use in therapy.

In one embodiment, there is provided a compound of formula (I) or a pharmaceutically acceptable salt thereof for use in the treatment of a condition or disorder mediated via KMO.

In one embodiment there is provided a compound of formula (I) or a pharmaceutically acceptable salt thereof for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In one embodiment there is provided a compound of formula (I) or a pharmaceutically acceptable salt thereof for use in the treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In one embodiment there is provided a compound of formula (I) or a pharmaceutically acceptable salt thereof for use in the treatment of acute pancreatitis.

In one embodiment there is provided (R)-3-(5-chloro-6-(1-(pyridin-2-yl)ethoxy)benzo[d]isoxazol-3-yl)propanoic acid or a pharmaceutically acceptable salt thereof. for use in the treatment of acute pancreatitis.

In one embodiment there is provided (R)-3-(5-chloro-6-(1-(6-methylpyridazin-3-yl)ethoxy)benzo[d]isoxazol-3-yl)propanoic acid or a pharmaceutically acceptable salt thereof. for use in the treatment of acute pancreatitis.

In one embodiment there is provided a compound of formula (I) or a pharmaceutically acceptable salt thereof for use in the treatment of chronic kidney disease.

In one embodiment there is provided (R)-3-(5-chloro-6-(1-(pyridin-2-yl)ethoxy)benzo[d]isoxazol-3-yl)propanoic acid or a pharmaceutically acceptable salt thereof. for use in the treatment of chronic kidney disease.

In one embodiment there is provided (R)-3-(5-chloro-6-(1-(6-methylpyridazin-3-yl)ethoxy)benzo[d]isoxazol-3-yl)propanoic acid or a pharmaceutically acceptable salt thereof. for use in the treatment of chronic kidney disease.

In a further aspect, there is provided the use of a compound of formula (I) or a pharmaceutically acceptable salt thereof in the manufacture of a medicament for the treatment of a condition or disorder mediated via KMO.

In one embodiment there is provided the use of a compound of formula (I) or a pharmaceutically acceptable salt thereof in the manufacture of a medicament for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In one embodiment there is provided the use of a compound of formula (I) or a pharmaceutically acceptable salt thereof in the manufacture of a medicament for use in the treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure.

In one embodiment there is provided the use of a compound of formula (I) or a pharmaceutically acceptable salt thereof in the manufacture of a medicament for use in the treatment of acute pancreatitis.

In one embodiment there is provided the use of (R)-3-(5-chloro-6-(1-(pyridin-2-yl)ethoxy)benzo[d]isoxazol-3-yl)propanoic acid or a pharmaceutically acceptable salt thereof in the manufacture of a medicament for use in the treatment of acute pancreatitis.

In one embodiment there is provided the use of (R)-3-(5-chloro-6-(1-(6-methylpyridazin-3-yl)ethoxy)benzo[d]isoxazol-3-yl)propanoic acid or a pharmaceutically acceptable salt thereof in the manufacture of a medicament for use in the treatment of acute pancreatitis.

In one embodiment there is provided the use of a compound of formula (I) or a pharmaceutically acceptable salt thereof in the manufacture of a medicament for use in the treatment of chronic kidney disease.

In one embodiment there is provided the use of (R)-3-(5-chloro-6-(1-(pyridin-2-yl)ethoxy)benzo[d]isoxazol-3-yl)propanoic acid or a pharmaceutically acceptable salt thereof in the manufacture of a medicament for use in the treatment of chronic kidney disease.

In one embodiment there is provided the use of (R)-3-(5-chloro-6-(1-(6-methylpyridazin-3-yl)ethoxy)benzo[d]isoxazol-3-yl)propanoic acid or a pharmaceutically acceptable salt thereof in the manufacture of a medicament for use in the treatment of chronic kidney disease.

A particular compound of the invention for use in the aforementioned methods of treatment is (R)-3-(5-chloro-6-(1-(pyridin-2-yl)ethoxy)benzo[d]isoxazol-3-yl)propanoic acid or a pharmaceutically acceptable salt thereof.

A particular compound of the invention for use in the aforementioned methods of treatment is (R)-3-(5-chloro-6-(1-(6-methylpyridazin-3-yl)ethoxy)benzo[d]isoxazol-3-yl)propanoic acid or a pharmaceutically acceptable salt thereof.

Compositions

The compounds of the invention will normally, but not necessarily, be formulated into pharmaceutical compositions prior to administration to a patient. Accordingly, in another aspect, there is provided a pharmaceutical composition comprising a compound of formula (I) or a pharmaceutically acceptable salt thereof and one or more pharmaceutically acceptable excipients. The pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (*Mack Publishing Company*), *The Handbook of Pharmaceutical Additives* (*Gower Publishing Limited*), *and The Handbook of Pharmaceutical Excipients* (*the American Pharmaceutical Association and the Pharmaceutical Press*).

The pharmaceutical compositions of the invention are prepared using techniques and methods known to those skilled in the art. Some of the methods commonly used in the art are described in Remington's Pharmaceutical Sciences (Mack Publishing Company).

The pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

The pharmaceutical composition of the invention may contain from 0.1% to 99% by weight of the active material, depending on the method of administration. The dose of the compound used in the treatment of the aforementioned conditions or disorders will vary in the usual way with the seriousness of the conditions or disorders, the weight of the subject, and other similar factors. However, as a general guide suitable unit doses may be 0.05 to 5000 mg, 1.0 to 500 mg or 1.0 to 200 mg and such unit doses may be administered once a day or more than once a day, for example two or three times a day. Such therapy may extend for a number of weeks, months or years.

In one embodiment injectable or infusible solutions, or reconstitutable powders, are preferred.

In one embodiment, a composition adapted for oral formulation is preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g.

sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of the invention may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The invention provides for a pharmaceutical composition for use in the treatment of acute pancreatitis, chronic kidney disease, acute kidney disease, acute kidney injury, other conditions associated with systemic inflammatory response syndrome (SIRS), Huntington's disease, Alzheimer's disease, spinocerebellar ataxias, Parkinson's disease, AIDS-dementia complex, HIV infection, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which comprises a therapeutically effective amount of a compound of formula (I) or a pharmaceutically acceptable salt thereof and a pharmaceutically acceptable excipient.

The invention provides for a pharmaceutical composition for use in the treatment of acute pancreatitis, chronic kidney disease, other conditions associated with systemic inflammatory response syndrome (SIRS), Huntington's disease, Alzheimer's disease, spinocerebellar ataxias, Parkinson's disease, AIDS-dementia complex, amylotrophic lateral sclerosis (ALS), depression, schizophrenia, sepsis, cardiovascular shock, severe trauma, acute lung injury, acute respiratory distress syndrome, acute cholecystitis, severe burns, pneumonia, extensive surgical procedures, ischemic bowel, severe acute hepatic disease, severe acute hepatic encephalopathy or acute renal failure which comprises a compound of formula (I) or a pharmaceutically acceptable salt thereof and one or more pharmaceutically acceptable excipients.

Biological Data

KMO inhibition can be determined by MS Rapidfire assay performed on the human cloned enzyme as described herein. The compounds of the Examples have demonstrated inhibitory activity at the KMO enzyme, using the MS Rapidfire functional assay described herein, or a substantially similar assay.

KMO MS Rapidfire Assay Protocol

Materials and Methods

Materials

L-Kynurenine (Kyn), 3-hydroxy-DL-kynurenine (3-HK), β-Nicotinamide adenine dinucleotide 2'-phosphate reduced tetrasodium salt hydrate (NADPH), 4-(2-hydroxyethyl)piperazine-1-ethanesulfonic acid (Hepes), DL-dithiothreitol (DTT), ethylenediaminetetraacetic acid (EDTA), CHAPS and trifluoroacetic acid (TFA) were purchased from Sigma- Aldrich Ltd. (Gillingham, Dorset, UK). HPLC-grade acetonitrile and formic acid were supplied by Fisher Scientific (Loughborough, UK).

Cloning and Expression of Human KMO

Full length human KMO was amplified by PCR from pcDNA5/FRT/V5-His-TOPO/hKMO (vector supplied by the University of Edinburgh) and cloned into pGEX6P-1 (GE Healthcare) using BamH1 and SaI1 restriction sites. DNA encoding the N-terminal glutathione-S-transferase (GST) tag, followed by a Pre-Scission protease cleavage site, and the full length KMO was amplified by PCR from pGEX6P-1-KMO and cloned into pFastbac1 (Invitrogen) using XbaI and EcoR1 restriction sites.

pFastbac1 GST-KMO was transposed into the baculovirus genome using the BAC-to-BAC technology (Invitrogen) and bacmid DNA was prepared and transfected into *Spodoptera frugiperda* (Sf9) cells using Cellfectin II (Invitrogen). Expression of a protein of the expected molecular weight (Mr 82,634) was seen by Western blot analysis using anti-GST-peroxidase conjugate.

Preparation of Membranes from Sf9 Cells Expressing Human GST-KMO

A P1 virus stock was generated from a single clone and used to infect 3×1.5 L cultures of Sf9 cells in 3 L Corning Fernbach flasks. The Sf9 cells were grown in Hyclone SFX media (Thermo Scientific) to about $3 \times 10^6$ cells/ml and were infected at a nominal multiplicity of infection of 3. Cells were harvested after 48 hours and disrupted by blending in 50 mM Hepes, pH 7.4, 1 mM EDTA buffer containing protease inhibitors. A low speed spin (400 g) was used to remove cell debris, followed by a high speed spin (75 000 g) to pellet the membranes. The membranes were purified in a discontinuous sucrose density gradient by re-suspending in 10% (w/v) sucrose and layering over 40% (w/v) sucrose, both in the above buffer. This was centrifuged at 150 000 g and the purified membranes were taken from the interface, collected by centrifugation at 100 000 g, resuspended in buffer and aliquoted for storage at −80° C. KMO activity was found to be associated with the membrane fraction only and no KMO activity was detected in membranes prepared from uninfected Sf9 cells. A batch of 104 mg of purified Sf9 KMO-membranes (as determined by the Pierce BCA protein assay using bovine serum albumin as standard) was prepared and validated in the RapidFire High-Throughput Mass Spectrometry (RF MS) assay.

RapidFire High-Throughput Mass Spectrometry Assay

Method 1

11 point, 3-fold serial dilutions of test compounds were prepared in DMSO and 100 nL of these solutions were dispensed into 384-well V-base polypropylene plates (Greiner Bio-one, Stonehouse, UK) using an Echo 555 acoustic dispenser (Labcyte, Sunnyvale, Calif.). This gave a final assay concentration range between 100 µM and 1.7 nM in 10 µL final assay volume (see below). 100 nL DMSO was dispensed into columns 6 and 18 for high and low controls, respectively, with prior inactivation of the enzyme in column 18 by pre-dispense of 30 µL of 0.5% (v/v) TFA.

Conditions for the assay of human KMO using isolated KMO-membranes were 50 mM Hepes, pH 7.5, 2 mM DTT, 1 mM EDTA, 100 µM CHAPS, 200 µM NADPH, 10 µM Kynurenine and 8 µg/ml KMO-membranes in a total reaction volume of 10 µL.

Assays were performed by initially dispensing 5 µL of a 2× Enzyme solution (16 µg/ml KMO-membranes in 50 mM Hepes, pH 7.5, 2 mM DTT, 2 mM EDTA, 200 µM CHAPS) into plates containing 100 nL compounds and incubating for 10 min at ambient temperature. Reactions were initiated by addition of 5 µL of 2× Substrate solution (400 µM NADPH, 20 µM Kynurenine in 50 mM Hepes, pH 7.5, 2 mM DTT) and incubated for 2 h at room temperature before quenching the reaction with 30 µL of 0.5% (v/v) TFA. Plates were centrifuged at 2500 rpm for 10 min before analysis. All additions were made using a Multidrop Combi dispenser (Thermo Fisher Scientific).

Quenched assay plates were transferred to a high-throughput RapidFire200 integrated autosampler/solid-phase extraction (SPE) system (Agilent Technologies, Wakefield, Mass.). Samples were aspirated from each well for 500 ms and 10 µL was loaded directly onto a RapidFire micro-scale SPE C18 (type C) cartridge, which was washed for 3 s with HPLC-grade water containing 0.1% (v/v) formic acid to remove non-organic components. Analytes were then eluted into the mass spectrometer, in a 3 s elution cycle, using 80% (v/v) acetonitrile/water containing 0.1% (v/v) formic acid, and the cartridge was then equilibrated by washing with water containing 0.1% (v/v) formic acid for 500 ms. This gave a total cycle time of 7 s, enabling analysis of a 384-well plate in approximately 45 min.

Both Kyn and 3-HK were detected using a Sciex AP14000 triple quadrupole mass spectrometer (Applied Biosystems, Concord, Ontario, Canada), equipped with an electrospray interface and operated in positive ion mode. Multiple reaction monitoring (MRM) was used to detect both Kyn and 3-HK using Q1/Q3 transitions at m/z 209.4 to 192.0 and m/z 225.3 to 208.2, respectively. The mass spectrometer used an ESI voltage of 5500 V and a source temperature of 600° C., with a dwell time of 50 ms for each transition.

Data Analysis

Individual MRM transitions were saved as text files and the extracted ion chromatograms were integrated and processed using the RapidFire® peak integration software (version 3.6).

Using the integrated peak area for 3-HK data was analysed within ActivityBase (ID Business Solutions Ltd, Surrey, UK). Dose response curves were fitted to equation (1):

$$\text{Inhibition}(\%) = \frac{(a-d)}{1 + \left(\frac{[I]}{IC_{50}}\right)^S} + d \qquad (1)$$

Where a is the uninhibited response, d is the fully inhibited response, [I] is the inhibitor concentration, $IC_{50}$ is [I] that gives 0.5×(a−d) and S is the Hill slope.

Method 2

11 point, 3-fold serial dilutions of test compounds were prepared in DMSO and 100 nL of these solutions were dispensed into 384-well V-base polypropylene plates (Greiner Bio-one, Stonehouse, UK) using an Echo 555 acoustic dispenser (Labcyte, Sunnyvale, Calif.). This gave a final assay concentration range between 10 µM and 0.17 nM in 10 µL final assay volume (see below). 100 nL DMSO was dispensed into columns 6 and 18 for high and low controls, respectively, with prior inactivation of the enzyme in column 18 by pre-dispense of 50 µL of 0.5% (v/v) TFA.

Conditions for the assay of human KMO using isolated KMO-membranes were 50 mM Hepes, pH 7.5, 2 mM DTT, 1 mM EDTA, 100 µM CHAPS, 200 µM NADPH, 10 µM Kynurenine and 4 µg/ml KMO-membranes in a total reaction volume of 10 µL.

Assays were performed by initially dispensing 5 µL of a 2× Enzyme solution (8 µg/ml KMO-membranes in 50 mM Hepes, pH 7.5, 2 mM DTT, 2 mM EDTA, 200 μM CHAPS) into plates containing 100 nL compounds and incubating for 30 min at ambient temperature. Reactions were initiated by addition of 5 μL of 2× Substrate solution (400 μM NADPH, 20 μM Kynurenine in 50 mM Hepes, pH 7.5, 2 mM DTT) and incubated for 2 h at room temperature before quenching the reaction with 50 μL of 0.5% (v/v) TFA. Plates were centrifuged at 3000 rpm for 10 min before analysis. All additions were made using a Multidrop Combi dispenser (Thermo Fisher Scientific).

Quenched assay plates were transferred to a high-throughput RapidFire200 integrated autosampler/solid-phase extraction (SPE) system (Agilent Technologies, Wakefield, Mass.). Samples were aspirated from each well for 650 ms and approximately 10 μL was loaded directly onto a Rapid-Fire micro-scale SPE C18 (type C) cartridge, which was washed for 1500 ms with HPLC-grade water containing 0.1% (v/v) formic acid to remove non-organic components. Analytes were then eluted into the mass spectrometer, in a 1500 ms elution cycle, using 80% (v/v) acetonitrile/water containing 0.1% (v/v) formic acid, and the cartridge was then equilibrated by washing with water containing 0.1% (v/v) formic acid for 500 ms. This gave a total cycle time of 7 s, enabling analysis of a 384-well plate in approximately 45 min.

Both Kyn and 3-HK were detected using a Sciex API4000 triple quadrupole mass spectrometer (Sciex, Warrington, Cheshire, UK), equipped with an electrospray interface and operated in positive ion mode. Multiple reaction monitoring (MRM) was used to detect both Kyn and 3-HK using Q1/Q3 transitions at m/z 209.2 to 192.0 and m/z 225.2 to 208.1, respectively. The mass spectrometer used an ESI voltage of 5500 V and a source temperature of 650° C., with a dwell time of 50 ms for each transition.

Data Analysis

Individual MRM transitions were saved as text files and the extracted ion chromatograms were integrated and processed using the RapidFire® peak integration software (version 4.0).

Using the integrated peak area for 3-HK data was analysed within ActivityBase (ID Business Solutions Ltd, Surrey, UK). Dose response curves were fitted to equation (1):

$$\text{Inhibition}(\%) = \frac{(a-d)}{1+\left(\frac{[I]}{IC_{50}}\right)^S} + d \quad (1)$$

Where a is the uninhibited response, d is the fully inhibited response, [I] is the inhibitor concentration, $IC_{50}$ is [I] that gives 0.5×(a−d) and S is the Hill slope.

The compounds of Examples 1-54 were tested essentially as described in at least one of the above assays. Those of skill in the art will recognise that in vitro binding assays and cell-based assays for functional activity are subject to experimental variability. Accordingly, it is to be understood that the $pIC_{50}$ values given below are exemplary only.

Exemplified compounds of the invention have median $pIC_{50}$ values of ≥5.0 in at least one of the above MS Rapidfire assays.

Certain exemplified compounds of the invention have median $pIC_{50}$ values of ≥5.5 in at least one of the above MS Rapidfire assays.

Examples 1, 1a-1m, 2, 3, 5-9, 13, 15-17, 20, 22, 23, 25 and 27 have median $pIC_{50}$ values of ≥8.0 in at least one of the above MS Rapidfire assays. Examples 29, 31, 35, 37, 39, 41, 43, 46, 47, 49 and 51 have median $pIC_{50}$ values of ≥8.0 in at least one of the above MS Rapidfire assays.

Example 1b has a median $pIC_{50}$=8.6 in at least one of the above MS Rapidfire assays. Examples 3 and 7 have a median $pIC_{50}$ value in at least one of the above MS Rapidfire assays of 8.6. Example 20 has a median $pIC_{50}$ value in at least one of the above MS Rapidfire assays of 8.7. Example 25 has a median $pIC_{50}$ value in at least one of the above MS Rapidfire assays of 8.4.

Examples 20a and 20b have median $pIC_{50}$ values at least one of the above MS Rapidfire assays of 8.7.

The invention claimed is:

1. A compound of Formula (I):

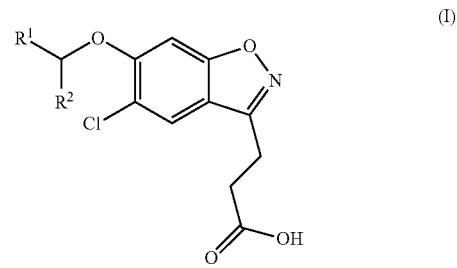

wherein:
  $R^1$ is heteroaryl either unsubstituted or substituted by methyl, ethyl, halo or =O; and
  $R^2$ is methyl; or
a pharmaceutically acceptable salt thereof.

2. The compound of Formula (1) or a pharmaceutically acceptable salt thereof according to claim 1, wherein:
  $R^1$ is selected from the group consisting of pyridyl and pyrimidinyl;
    wherein:
      the pyridyl and pyrimidinyl may be unsubstituted or substituted by methyl, ethyl, halo or =O.

3. The compound of Formula (1) or a pharmaceutically acceptable salt thereof according to claim 1, wherein $R^1$ is pyridyl.

4. The compound of Formula (1) or a pharmaceutically acceptable salt thereof according to claim 1, wherein $R^1$ is pyrimidinyl.

5. The compound of Formula (1) or a pharmaceutically acceptable salt thereof according to claim 4, wherein the pyrimidinyl is substituted with methyl.

6. A compound of Formula (I) which is:

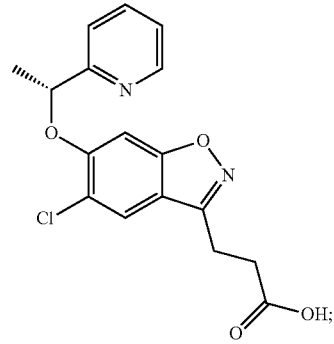 [SMILES: C[C@@H](Oc1cc2onc(CCC(=O)O)c2cc1Cl)c1ccccn1]

or a pharmaceutically acceptable salt thereof.

7. A compound of Formula (I) according to claim 6 which is:

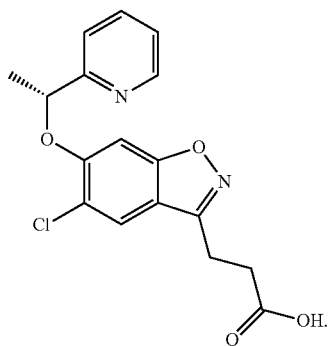 [SMILES: C[C@@H](Oc1cc2onc(CCC(=O)O)c2cc1Cl)c1ccccn1]

8. A compound of Formula (I) which is:

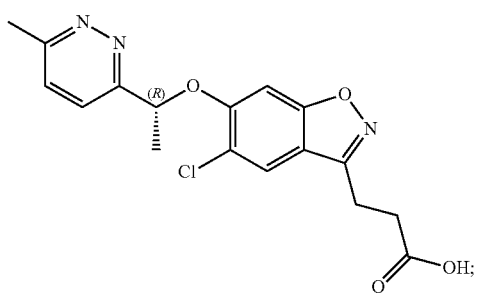

or a pharmaceutically acceptable salt thereof.

9. A pharmaceutical composition comprising:
   a) a compound of Formula (I) or pharmaceutically acceptable salt thereof as defined in claim 1; and
   b) a pharmaceutically acceptable excipient.

10. A pharmaceutical composition comprising:
    a) a compound of Formula (I) or pharmaceutically acceptable salt thereof as defined in claim 6; and
    b) a pharmaceutically acceptable excipient.

11. A pharmaceutical composition comprising:
    a) a compound of Formula (I) or pharmaceutically acceptable salt thereof as defined in claim 8; and
    b) a pharmaceutically acceptable excipient.

12. A method for treating a condition or disorder mediated by Kynurenine Monooxygenase (KMO), which comprises administering a therapeutically effect amount of a compound of Formula (I) as defined in claim 1:

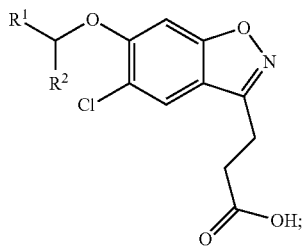

or a pharmaceutically acceptable salt thereof;
wherein;
    the condition or disorder mediated by Kynurenine Monooxygenase KMO is selected from acute pancreatitis and chronic kidney disease.

13. A method for treating a condition or disorder mediated by Kynurenine Monooxygenase (KMO), which comprises administering a therapeutically effect amount of a compound of Formula (I) as defined in claim 6:

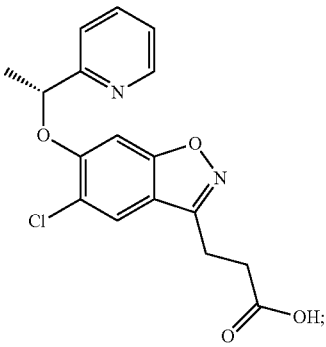 [SMILES: C[C@@H](Oc1cc2onc(CCC(=O)O)c2cc1Cl)c1ccccn1]

or a pharmaceutically acceptable salt thereof;
wherein;
    the condition or disorder mediated by Kynurenine Monooxygenase KMO is selected from acute pancreatitis and chronic kidney disease.

14. A method for treating a condition or disorder mediated by Kynurenine Monooxygenase (KMO), which comprises administering to a patient in need thereof a therapeutically effective amount of a compound of Formula (I) as defined in claim 8:

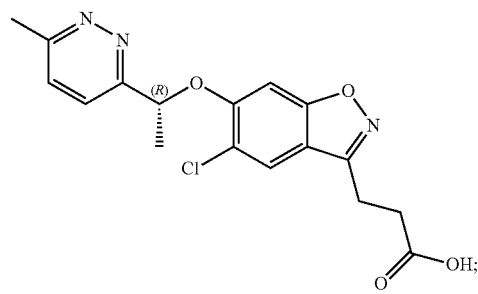

or a pharmaceutically acceptable salt thereof;
wherein:
    the condition or disorder mediated by Kynurenine Monooxygenase (KMO) is selected from acute pancreatitis and chronic kidney disease.

15. A method according to claim 14, wherein the condition or disorder mediated by Kynurenine Monooxygenase (KMO) is acute pancreatitis.

16. A method for treating a condition or disorder mediated by Kynurenine Monooxygenase (KMO), which comprises administering a pharmaceutical composition according to claim 9;
wherein;
    the condition or disorder mediated by KMO is selected from acute pancreatitis and chronic kidney disease.

17. A method for treating a condition or disorder mediated by Kynurenine monooxygenase (KMO), which comprises administering a pharmaceutical composition according to claim 10;

wherein;

the condition or disorder mediated by KMO is selected from acute pancreatitis and chronic kidney disease.

18. A method for treating a condition or disorder mediated by Kynurenine monooxygenase (KMO), which comprises administering a pharmaceutical composition according to claim 11;

wherein;

the condition or disorder mediated by KMO is selected from acute pancreatitis and chronic kidney disease.

19. A method for treating acute pancreatitis and chronic kidney disease, which comprises administering a therapeutically effect amount of a compound of Formula (I) as defined in claim 1:

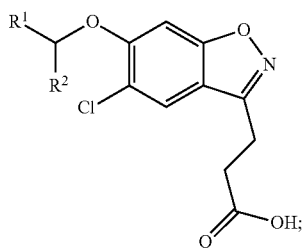

(I)

or a pharmaceutically acceptable salt thereof.

20. A method for treating acute pancreatitis and chronic kidney disease, which comprises administering to a patient in need thereof a therapeutically effective amount of a compound which is:

or a pharmaceutically acceptable salt thereof.

21. A method for treating acute pancreatitis, which comprises administering to a patient in need thereof a therapeutically effective amount of a compound which is or a pharmaceutically acceptable salt thereof.

22. A method for treating acute pancreatitis and chronic kidney disease, which comprises administering a pharmaceutical composition of claim 9 to a patient in need thereof.

23. A method for treating acute pancreatitis and chronic kidney disease which comprises administering a pharmaceutical composition of claim 10 to a patient in need thereof.

24. A method for treating acute pancreatitis and chronic kidney disease which comprises administering a pharmaceutical composition of claim 11 to a patient in need thereof.

* * * * *